(12) United States Patent
Dombrowski

(10) Patent No.: US 11,673,911 B2
(45) Date of Patent: Jun. 13, 2023

(54) STABILIZED NUCLEIC ACIDS ENCODING MESSENGER RIBONUCLEIC ACID (MRNA)

(71) Applicant: Intellia Therapeutics, Inc., Cambridge, MA (US)

(72) Inventor: Christian Dombrowski, Auburndale, MA (US)

(73) Assignee: Intellia Therapeutics, Inc., Cambridge, MA (US)

(*) Notice: Subject to any disclaimer, the term of this patent is extended or adjusted under 35 U.S.C. 154(b) by 629 days.

(21) Appl. No.: 16/791,076

(22) Filed: Feb. 14, 2020

(65) Prior Publication Data

US 2020/0172564 A1 Jun. 4, 2020

Related U.S. Application Data

(63) Continuation of application No. PCT/US2018/046772, filed on Aug. 14, 2018.

(60) Provisional application No. 62/545,883, filed on Aug. 15, 2017.

(51) Int. Cl.
| | |
|---|---|
| *C12N 15/11* | (2006.01) |
| *C07H 21/02* | (2006.01) |
| *C12N 15/63* | (2006.01) |
| *C07K 14/475* | (2006.01) |
| *C07K 14/52* | (2006.01) |
| *C12N 9/22* | (2006.01) |

(52) U.S. Cl.
CPC ............ *C07H 21/02* (2013.01); *C12N 15/11* (2013.01); *C12N 15/63* (2013.01); *C07K 14/475* (2013.01); *C07K 14/521* (2013.01); *C12N 9/22* (2013.01)

(58) Field of Classification Search
CPC ......... C12N 15/68; C12N 15/63; C12N 15/67
See application file for complete search history.

(56) References Cited

U.S. PATENT DOCUMENTS

| | | | |
|---|---|---|---|
| 2016/0243258 A1* | 8/2016 | Scharenberg | A61K 41/0047 |
| 2017/0166905 A1* | 6/2017 | Eberle | C12N 15/68 |
| 2018/0119213 A1 | 5/2018 | Kim et al. | |

FOREIGN PATENT DOCUMENTS

| | | |
|---|---|---|
| KR | 101786396 B1 | 11/2017 |
| WO | 2016115355 A1 | 7/2016 |

OTHER PUBLICATIONS

Chang, H. et al., "TAIL-seq: Genome-wide Determination of Poly(A) Tail Length and 3' End Modifications" Cell Press, vol. 53, Mar. 20, 2014 (Mar. 20, 2014) pp. 1044-1052.
International Search and Written Opinion issued for PCT/US2018/046772 dated Dec. 4, 2018.
Jalkanen, A. et al., "Determinants and implications of mRNA poly(A) tail size—Does this protein make my tail look big?" Seminars in Cell and Developmental Biology, vol. 34, Oct. 1, 2014 (Oct. 1, 2014), pp. 24-32.
Lim, J. et al., "Mixed tailing by TENT4A and TENT4B shields mRNA from rapid deadenylation" Science, vol. 361, No. 6403, Jul. 19, 2018 (Jul. 19, 2018), pp. 701-704.
Lim, J. et al., "Uridylation by TUT4 and TUT7 Marks mRNA for Degradation" CELL, vol. 159, No. 6, Dec. 4, 2014 (Dec. 4, 2014), pp. 1365-1376.
Sergeeva, O.V. et al., "mRNA-Based Therapeutics—Advances and Perspectives" Biochemistry (Moscow) 81(7):709-722 (2016).

* cited by examiner

*Primary Examiner* — Weihua Fan
(74) *Attorney, Agent, or Firm* — McNeill Baur PLLC

(57) ABSTRACT

This disclosure relates to the field of poly-adenylated (poly-A) tails. In some embodiments, a DNA encodes a poly-A tail located 3' to nucleotides encoding a protein of interest, wherein the poly-A tail comprises one or more non-adenine nucleotide.

22 Claims, 7 Drawing Sheets

Specification includes a Sequence Listing.

STABILIZED NUCLEIC ACIDS ENCODING MESSENGER RIBONUCLEIC ACID (MRNA)

This application is a Continuation of International Application No. PCT/US2018/046772, which was filed Aug. 14, 2018 and which claims the benefit of priority to U.S. Provisional Application No. 62/545,883, which was filed on Aug. 15, 2017, both of which are incorporated by reference in their entirety.

This disclosure relates to the field of stabilized messenger ribonucleic acid (mRNA) and DNA encoding the stabilized mRNA.

BACKGROUND

Polyadenylation is the process of adding multiple adenine nucleotides to the 3' end of a messenger RNA (mRNA), forming a poly-A tail. The poly-A tail consists of multiple repeated adenine nucleotides, such as adenosine monophosphates, without other bases interrupting the sequence. The poly-A tail is critical for the nuclear export, translation, and stability of mRNA. In nature, as mRNA is produced from DNA, a terminal transferase adds adenine nucleotides to the 3' end of mRNA. This enzymatic process can be applied when producing mRNA ex vivo, but the process is difficult to control and results in poly-A tails of different lengths. By encoding a poly-A tail in the plasmid, it is possible to decrease the heterogeneity in the poly-A tail. However, it does not eliminate the heterogeneity, and has additional downsides such as potential instability of the plasmid.

The poly-A tail acts as the binding site for poly-A-binding protein. Poly-A-binding protein assists in exporting mRNA from the nucleus, translation, and inhibiting degradation of the mRNA. In the absence of export from the nucleus, mRNAs are typically degraded by the exosome. The poly-A-binding protein recruits proteins necessary for translation.

mRNA is now being used as a therapeutic molecule, for example, for the treatment of various diseases and disorders. mRNA is delivered to a subject in lieu of the protein so that the subject's cells produce the protein encoded by the mRNA within the cell. For these and other purposes, mRNA may be prepared via transcription from a DNA template, often contained in a plasmid. During mRNA production, the poly-A tail may be added to mRNA enzymatically after transcription from a plasmid or encoded on the plasmid itself. When the poly-A tail is encoded on a plasmid, the poly-A tail may become shorter (i.e., lose adenine nucleotides) over cycles of plasmid DNA replication, potentially leading to large variations in the resulting DNA and subsequent mRNA population. Thus, there exists a need in the art to design plasmids encoding poly-A tails that are stable and resistant to gradual loss of nucleotides encoding poly-A adenine nucleotides during DNA replication.

SUMMARY

Disclosed herein are DNA encoding, and mRNA comprising, poly-adenylated (poly-A) tails comprising consecutive adenine nucleotides located 3' to nucleotides encoding a protein of interest, wherein the poly-A tail is stabilized by inserting non-adenine nucleotide "anchors."

As used herein, the term "poly-A tail" refers to a poly-A tail on an mRNA molecule, or a sequence encoding a poly-A tail within a DNA plasmid. A poly-A tail may be encoded by a complementary DNA sequence within a plasmid. A sequence of repeating thymine (T) nucleotides in a DNA sequence, e.g. a homopolymer T sequence, may encode a poly-A tail on an mRNA. Two or more consecutive adenosine (e.g. adenosine or deoxyadenosine), thymidine, or other nucleotides are called homopolymers. Naturally-occurring poly-A tails comprise long, uninterrupted homopolymer A sequences.

The non-adenine nucleotide anchors disclosed herein interrupt the poly-A tail at regular or irregularly spaced intervals and stabilize the DNA encoding the poly-A tail as well as the mRNA produced from the DNA. Exemplary non-adenine nucleotide anchors are provided in Table 4. An anchor sequence, for example, is adjacent to two adenine nucleotide homopolymer sequences within the poly-A tail.

In some embodiments, a DNA composition comprising nucleotides encoding a poly-adenylated (poly-A) tail located 3' to nucleotides encoding a protein of interest, wherein the poly-A tail comprises at least 8 consecutive adenine (A) nucleotides and one or more non-adenine (A) nucleotides is encompassed.

In some embodiments, the poly-A tail comprises at least 10, 15, 20, 25, 30, 35, 40, 45, 50, 55, 60, 65, 70, 75, 80, 85, or 90 consecutive adenine nucleotides.

In some instances, the one or more non-adenine nucleotides prevent the loss of one or more adenine nucleotides during DNA replication as compared to the loss that occurs in a DNA comprising a 3' tail of a similar or same length that contains only adenine nucleotides.

In some embodiments, the one or more non-adenine nucleotides are positioned to interrupt the consecutive adenine nucleotides so that a poly(A) binding protein can bind to a stretch of consecutive adenine nucleotides.

In some embodiments, the poly-A tail comprises at least 50 total adenine nucleotides.

In some embodiments, the poly-A tail comprises 40-500 total adenine nucleotides.

In some instances, the poly-A tail comprises 95-100 total adenine nucleotides.

In some embodiments, the poly-A tail comprises or contains 90, 91, 92, 93, 94, 95, 96, or 97 total adenine nucleotides.

In some embodiments, the poly-A tail comprises or contains 96 or 97 total adenine nucleotides.

In some embodiments, the poly-A tail comprises or contains one non-adenine nucleotide or one consecutive stretch of 2-10 non-adenine nucleotides.

In some embodiments, the non-adenine nucleotide(s) is located after at least 8, 9, 10, 11, or 12 consecutive adenine nucleotides.

In some instances, the one or more non-adenine nucleotides are located after at least 8-50 consecutive adenine nucleotides.

In some embodiments, the one or more non-adenine nucleotides are located after at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

In some embodiments, the poly-A tail comprises or contains one non-adenine nucleotide or one consecutive stretch of 2-10 nucleotides every 8-50 consecutive adenine nucleotides. In some embodiments, the poly-A tail comprises or contains one non-adenine nucleotide or one consecutive stretch of 2-10 nucleotides comprising at least two non-adenine nucleotides every 8-50 consecutive adenine nucleotides. In some embodiments, the poly-A tail has one or more non-adenine nucleotides or one or more consecutive stretches of 2-10 non-adenine nucleotides irregularly spaced anywhere along the length of the poly-A tail, wherein somewhere along the length of the poly-A tail there are at least 8 consecutive adenines. For example, a poly-A tail may be 70-1000 nucleotides in length, and have any number of non-adenines (either singly or grouped) irregularly spaced along the length, as long as there is one or more stretch of at least 8 consecutive adenines.

In some instances, the poly-A tail comprises or contains one non-adenine nucleotide or one consecutive stretch of 2-10 nucleotides every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

In some instances, the poly-A tail comprises or contains one non-adenine nucleotide or one consecutive stretch of 2-10 nucleotides comprising at least two non-adenine nucleotides every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

In some embodiments, the poly-A tail comprises or contains 1, 2, 3, 4, or 5 consecutive non-adenine nucleotides every 8-50 consecutive adenine nucleotides.

In some instances, the poly-A tail comprises or contains 1, 2, 3, 4, or 5 consecutive non-adenine nucleotides every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

In some embodiments, the poly-A tail comprises or contains more than one non-adenine nucleotide or more than one consecutive stretch of 2-10 nucleotides as interrupting sequences irregularly spaced within the poly-A tail.

In some embodiments, the poly-A tail comprises or contains more than one non-adenine nucleotide or more than one consecutive stretch of 2-10 nucleotides comprising at least two non-adenine nucleotides irregularly spaced within the poly-A tail.

In some instances, the poly-A tail comprises or contains one non-adenine nucleotide or 2, 3, 4, or 5 consecutive non-adenine nucleotides every 12 consecutive adenine nucleotides.

In some embodiments, the poly-A tail comprises or contains one non-adenine nucleotide or 2, 3, 4, or 5 consecutive non-adenine nucleotides every 16 consecutive adenine nucleotides.

In some embodiments, the poly-A tail comprises or contains one non-adenine nucleotide or 2, 3, 4, or 5 consecutive non-adenine nucleotides every 25 consecutive adenine nucleotides.

In some instances, the poly-A tail comprises or contains one non-adenine nucleotide or 2, 3, 4, or 5 consecutive non-adenine nucleotides every 30 consecutive adenine nucleotides.

In some embodiments, the poly-A tail comprises or contains one non-adenine nucleotide or 2, 3, 4, or 5 consecutive non-adenine nucleotides every 39 consecutive adenine nucleotides.

In some embodiments, the non-adenine nucleotide is guanine, cytosine, or thymine. In some instances, the non-adenine nucleotide is a guanine nucleotide. In some embodiments, the non-adenine nucleotide is a cytosine nucleotide. In some embodiments, the non-adenine nucleotide is a thymine nucleotide.

In some instances, where more than one non-adenine nucleotide is present, the non-adenine nucleotide may be selected from: a) guanine and thymine nucleotides; b) guanine and cytosine nucleotides; c) thymine and cytosine nucleotides; or d) guanine, thymine and cytosine nucleotides.

In some embodiments, the non-adenine nucleotide consists of one non-adenine nucleotide selected from guanine, cytosine, and thymine.

In some instances, the non-adenine nucleotides comprise two non-adenine nucleotides selected from one or more of guanine, cytosine, and thymine.

In some embodiments, the non-adenine nucleotides comprise three non-adenine nucleotides selected from one or more of guanine, cytosine, and thymine.

The adenine nucleotides may be adenosine monophosphate.

In some embodiments, the protein encoded by the mRNA is a therapeutic protein. In some instances, the protein a cytokine, chemokine, growth factor, Cas9 or modified Cas9.

In some embodiments, mRNA encoded by any of the DNAs described herein is encompassed.

In some embodiments, the DNA is within a vector. The vector may be within a host cell, including insect, bacterial, or mammalian (e.g., human) cells.

In some embodiments, the one or more non-adenine nucleotide prevents loss of nucleotides encoding the poly-A tail within the vector during growth of the host cell as compared to the loss that occurs in a DNA comprising nucleotides encoding a poly-A tail of a similar or same length that contains only adenine nucleotides.

Methods of producing mRNA from any of the DNA vectors described herein are encompassed comprising: linearizing the vector downstream of the poly-A tail; denaturing the linearized vector; and contacting the denaturized DNA with an RNA polymerase in the presence of guanine, cytosine, uracil, and adenine nucleotides.

In some embodiments, this disclosure includes a DNA comprising nucleotides encoding a poly-adenylated (poly-A) tail located 3' to nucleotides encoding a protein of interest, wherein the poly-A tail comprises a first homopolymer sequence of at least 8 consecutive adenine (A) nucleotides and an interrupting sequence comprising one or more non-adenine (A) nucleotides. In some such embodiments, the poly-A tail further comprises a second homopolymer sequence of at least consecutive adenine (A) nucleotides. In some embodiments, the poly-A tail comprises three or more homopolymer sequences of at least 8 consecutive adenine (A) nucleotides. In some embodiments, the first and/or subsequent homopolymer sequence comprises at least 10, 15, 20, 25, 30, 35, or 40 consecutive adenine nucleotides. In some embodiments, the one or more non-adenine nucleotide prevents the loss of one or more adenine nucleotide during DNA replication as compared to the loss that occurs in a DNA comprising a 3' tail of a similar or same length that contains only adenine nucleotides. In some embodiments, the one or more non-adenine nucleotide is positioned to interrupt the consecutive adenine nucleotides so that a poly(A) binding protein can bind to a stretch of consecutive adenine nucleotides. In some embodiments, the poly-A tail comprises at least 50 total adenine nucleotides. In some embodiments, the poly-A tail comprises 40-1000, 40-900, 40-800, 40-700, 40-600, 40-500, 40-400, 40-300, 40-200, or 40-100 total adenine nucleotides. In some embodiments, the poly-A tail comprises 95-100 total adenine nucleotides. In some embodiments, the poly-A tail comprises or contains 90, 91, 92, 93, 94, 95, 96, or 97 total adenine nucleotides. In some embodiments, the poly-A tail comprises or contains 96 or 97 total adenine nucleotides. In some embodiments, the one or more interrupting sequence comprises or contains one non-adenine nucleotide or one consecutive stretch of 2-10 non-adenine nucleotides. In some embodiments, the one or more interrupting sequence comprises or contains one non-adenine nucleotide or one consecutive stretch of 2-10 nucleotides that includes two or more non-adenine nucleotides. In some embodiments, the non-adenine nucleotide(s) is located after at least 8, 9, 10, 11, or 12 consecutive adenine nucleotides. In some embodiments, the one or more non-adenine nucleotide is located after at least 8-50 consecutive adenine nucleotides. In some embodiments, the one or more non-adenine nucleotide is located after at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

In some embodiments, as described in the preceding paragraph, the interrupting sequence is a trinucleotide, dinucleotide or mononucleotide interrupting sequence. In some such embodiments, the poly-A tail comprises or contains one non-adenine nucleotide or one consecutive stretch of 2-10 non-adenine nucleotides every 8-50 consecutive adenine nucleotides. In some embodiments, the poly-A tail comprises or contains one non-adenine nucleotide or one consecutive stretch of 2-10 non-adenine nucleotides every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides. In some embodiments, the poly-A tail comprises or contains 1, 2, 3, 4, or 5 consecutive non-adenine nucleotides every 8-50 consecutive adenine nucleotides. In some embodiments, the poly-A tail comprises or contains 1, 2, 3, 4, or 5 consecutive non-adenine nucleotides every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides. In some embodiments, the poly-A tail comprises or contains more than one non-adenine nucleotide or more than one consecutive stretch of 2-10 non-adenine nucleotides. In some embodiments, the more than one non-adenine nucleotide or more than one consecutive stretch of 2-10 non-adenine nucleotides are irregularly spaced within the poly-A tail. In some embodiments, the poly-A tail comprises or contains one non-adenine nucleotide or 2, 3, 4, or 5 consecutive non-adenine nucleotides every 12 consecutive adenine nucleotides. In some embodiments, the poly-A tail comprises or contains one non-adenine nucleotide or 2, 3, 4, or 5 consecutive non-adenine nucleotides every 16 consecutive adenine nucleotides. In some embodiments, the poly-A tail comprises or contains one non-adenine nucleotide or 2, 3, 4, or 5 consecutive non-adenine nucleotides every 25 consecutive adenine nucleotides. In some embodiments, the poly-A tail comprises or contains one non-adenine nucleotide or 2, 3, 4, or 5 consecutive non-adenine nucleotides every 30 consecutive adenine nucleotides. In some embodiments, the poly-A tail comprises or contains one non-adenine nucleotide or 2, 3, 4, or 5 consecutive non-adenine nucleotides every 39 consecutive adenine nucleotides. In some embodiments, the non-adenine nucleotide is guanine, cytosine, or thymine. In some embodiments, the non-adenine nucleotide is a guanine nucleotide. In some embodiments, the non-adenine nucleotide is a cytosine nucleotide. In some embodiments, the non-adenine nucleotide is a thymine nucleotide. In some embodiments, the DNA comprises more than one non-adenine nucleotide selected from: (a) guanine and thymine nucleotides; (b) guanine and cytosine nucleotides; (c) thymine and cytosine nucleotides; or (d) guanine, thymine and cytosine nucleotides. In some embodiments described above, the non-adenine nucleotide consists of one non-adenine nucleotide selected from guanine, cytosine, and thymine. In some embodiments, non-adenine nucleotides comprise two non-adenine nucleotides selected from one or more of guanine, cytosine, and thymine. In some embodiments, non-adenine nucleotides comprise three non-adenine nucleotides selected from one or more of guanine, cytosine, and thymine. In some embodiments, adenine nucleotides are adenosine monophosphate. In some embodiments, the protein is a therapeutic protein. In some embodiments, the protein a cytokine or chemokine. In some embodiments, the protein a growth factor. In some embodiments, the protein is Cas9 or modified Cas9.

This disclosure also encompasses an mRNA encoded by the DNA as described in the preceding paragraphs.

In some embodiments, the DNA described in the preceding paragraphs may also be comprised within a vector. In some embodiments, the vector is comprised within a host cell. In some embodiments, where the DNA is within a vector, the one or more non-adenine nucleotide prevents loss of nucleotides encoding the poly-A tail within the vector during growth of the host cell as compared to the loss that occurs in a DNA comprising nucleotides encoding a poly-A tail of a similar or same length that contains only adenine nucleotides.

This disclosure also encompasses methods of producing mRNA from the DNA vectors described herein, comprising: (a) linearizing the vector downstream of the poly-A tail; (b) denaturing the linearized vector; and (c) contacting the denaturized DNA with an RNA polymerase in the presence of guanine, cytosine, uracil, and adenine nucleotides.

FIGURE LEGENDS

DETAILED DESCRIPTION

Figure 1:
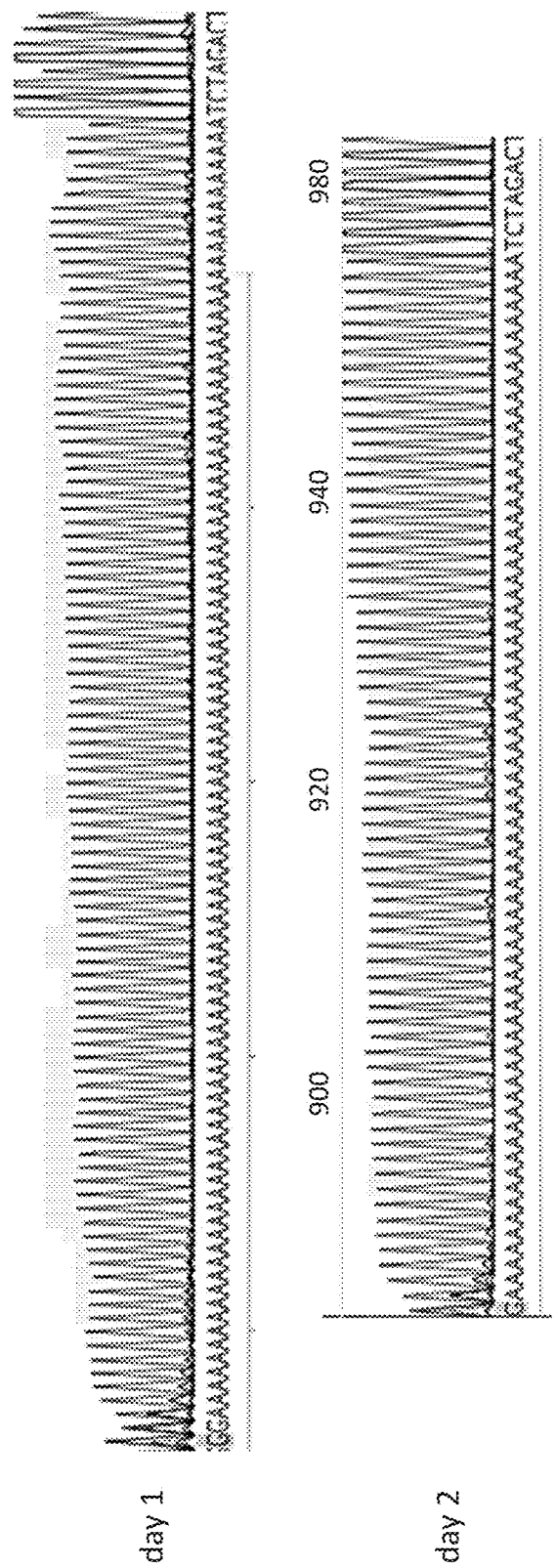
FIG. 1 shows a sequence encoding a poly-A tail that contains only adenosines decreasing in length over rounds of growth. Each clone refers to a DNA generated by successive rounds of growth/purification of host cells expressing plasmid encoding the clones.

Disclosed herein are DNAs encoding a poly-adenylated tail located 3' to nucleotides encoding a protein of interest, wherein the poly-A tail comprises one or more non-adenine nucleotides. During DNA replication, DNA encoding a poly-A tail comprising one or more non-adenine nucleotide may show less gradual loss of adenine nucleotides within the poly-A tail compared with poly-A tails consisting only of adenine nucleotides. Thus, plasmids comprising DNA encoding a poly-A tail comprising one or more non-adenine nucleotide are provided. mRNA encoded by such DNA is also encompassed. Both the DNA and RNA may exhibit greater stability against processive loss of adenine nucleotides than similar molecules comprising non-interrupted poly-A tails.

The protein of interest may be any natural or non-natural protein. As used herein, "protein" refers to any sequence of consecutive amino acids. As such, a protein may refer to a protein that comprises the full amino acid sequence of a naturally occurring protein. In addition, a protein may refer to an amino acid sequence that comprises a fragment of a full-length protein. A protein may be a naturally-occurring sequence, a naturally-occurring sequence with one or more modifications, or an artificial sequence that does not occur in nature.

The protein of interest may be of therapeutic use in a subject, or this protein may be of use in a biochemical reaction. Therapeutic proteins include, for example, growth factors, antigens for vaccines or immuno-oncology, and enzymes, among others. Therapeutic proteins may be naturally occurring or modified. In certain circumstances, a modified protein may be a fusion protein.

In some embodiments, expression of a protein by an mRNA is for use as a treatment for a disease. In some embodiments, expression of a protein by an mRNA is for use as a cancer immunotherapy, vaccination against infectious disease, to induce tolerance to a type I allergy, as a replacement therapy, or as a regenerative medicine (see Sergeeva O V et al, *Biochemistry (Moscow)* 81(7):709-722 (2016)).

In some embodiments, autologous dendritic cells are transfected ex vivo with an mRNA encoding for prostate-specific antigen (PSA) to modulate the T-cell immune response in subjects with metastatic prostate cancer.

In some embodiments, an mRNA is a prophylactic vaccine. In some embodiments, an mRNA encodes for one or more antigenic proteins. In some embodiments, the antigenic protein(s) is a viral protein. In some embodiments, the mRNA causes cells of the body to produce and express an antigenic protein. In some embodiments, the mRNA causes expression of antigenic proteins without a danger or disease or spread between individuals. In some embodiments, expression of antigenic proteins causes the immune system of a subject to produce antibodies. In some embodiments, these antibodies can neutralize a virus and prevent future infection after exposure to the virus. In some embodiments, the mRNA is a prophylactic vaccine for an infectious disease. In some embodiments, the mRNA is prophylactic vaccine against influenza, chikungunya, Zika, cytomegalovirus, human metapneumovirus (HMPV), or parainfluenza virus type 3 (PIV3). In some embodiments, the mRNA is a prophylactic vaccine against influenza H10 or H7 subtypes.

In some embodiments, an mRNA is a personalized cancer vaccine. In some embodiments, an mRNA primes the immune system of a subject with cancer to recognize cancer cells and mount a response. In some embodiments, this response is tailored to the individual patient's cancer or tumor. In some embodiments, an mRNA encodes a patient's specific neoantigens (unique proteins with mutations present in the patient's cancer or tumor). In some embodiments, an mRNA causes expression of a patient's specific neoantigens. In some embodiments, expression of neoantigens elicits a specific immune response in the patient to recognize and destroy cancer cells. In some embodiments, an mRNA is of use as a personalized cancer vaccine. In some embodiments, an mRNA is of use as a personalized cancer vaccine together with one or more checkpoint inhibitor antibodies, such as anti-PD-1 therapies.

In some embodiments, an mRNA is of use for intratumoral immuno-oncology. In some embodiments, injection of an mRNA into a tumor reduces off-target effects and/or may be more potent compared to systemic administration. In some embodiments, the mRNA causes expression of OX40L (CD252), the ligand for CD134. In some embodiments, the mRNA causes expression of cytokines such as interleukin 12 (IL-12).

In some embodiments, an mRNA causes expression of a protein for localized therapy. In some embodiments, an mRNA causes creation of more blood vessels and improved blood supply in a local tissue. In some embodiments, the mRNA causes expression of vascular endothelial growth factor A (VEGF-A). In some embodiments, expression of VEGF-A is local and transient. In some embodiments, local and transient expression of VEGF-A is of use for treatment of heart failure or after a heart attack, of diabetic wound healing, or of other ischemic vascular diseases.

In some embodiments, an mRNA causes expression of a protein for replacement therapy. In some embodiments, the protein is surfactant protein-B.

In some embodiments, an mRNA causes expression of an RNA-guided nuclease such as class 2 CRISPR-associated Cas endonuclease, e.g. Cas9/Csn1 (Cas9). An exemplary Cas9 sequence is UniProt Q99ZW2. In some embodiments, the protein is a modified Cas9 or a Cas9 protein fused to another functional protein or peptide. Modified versions of Cas9 having one catalytic domain, either RuvC or HNH, that is inactive are termed "nickases". In some embodiments, the compositions and methods comprise nickases. In some embodiments, the compositions and methods comprise a nickase Cas9 that induces a nick rather than a double strand break in the target DNA.

In some embodiments, the Cas protein may be modified to contain only one functional nuclease domain. For example, the Cas protein may be modified such that one of the nuclease domains is mutated or fully or partially deleted to reduce its nucleic acid cleavage activity. In some embodiments, a nickase Cas is used having a RuvC domain with reduced activity. In some embodiments, a nickase Cas is used having an inactive RuvC domain. In some embodiments, a nickase Cas is used having an HNH domain with reduced activity. In some embodiments, a nickase Cas is used having an inactive HNH domain.

In some embodiments, chimeric Cas proteins are encoded by the DNA, where one domain or region of the protein is replaced by a portion of a different protein. In some embodiments, a Cas nuclease domain may be replaced with a domain from a different nuclease such as Fok1. In some embodiments, a Cas protein may be a modified nuclease.

I. DNA Encoding Poly-A Tails Comprising Non-Adenine Nucleotides

As used herein, a "poly-A tail" refers to a sequence comprising adenosines or other adenine nucleotides at the 3' end of an mRNA. While natural poly-A tails may be comprised solely of adenine nucleotides, a "poly-A tail" of the present invention is stabilized by one or more non-adenine nucleotide "anchors". In some embodiments, the poly-A tail comprises at least 8 consecutive adenine nucleotides and one or more interrupting sequence comprising a non-adenine nucleotide. In other words, the poly-A tails of the present invention comprise at least 8 consecutive adenines, but also comprise one or more non-adenine nucleotide within the interrupting or anchor sequences. The interrupting sequences disclosed herein interrupt the poly-A tail at regular or irregularly spaced intervals and stabilize the DNA encoding the poly-A tail as well as the mRNA produced from the DNA. Exemplary interrupting sequences are provided in Table 4.

As used herein, "non-adenine nucleotides" refer to any natural or non-natural nucleotides that do not comprise adenine. Guanine, thymine, and cytosine nucleotides are exemplary non-adenine nucleotides.

Native poly-A tails are added in a process of polyadenylation that begins after transcription of a DNA into mRNA. In molecular biology methods, however, poly-A tails are often encoded by a section of DNA within a plasmid that encodes a protein of interest. In this instance, the size of the poly-A tail (i.e., the number of adenine nucleotides comprised in the poly-A tail) is directly dependent on the number of DNA nucleotides in the plasmid that encode for these consecutive adenine nucleotides.

The number of DNA nucleotides encoding the poly-A tail may gradually decrease during DNA replication during, for example, growth of the plasmid in a host cell. When the number of consecutive adenine-encoding nucleotides in a plasmid reduces, the yield of plasmid encoding full-length poly-A tail is reduced, and the resulting mRNA having shorter poly-A tails may have decreased stability and/or increased degradation. For example, an mRNA with a poly-A tail of 40 consecutive adenine nucleotides might be expected to have lower stability than an mRNA with a poly-A tail of 90 or more nucleotides. By lower stability, it is meant that an mRNA may be degraded more quickly, and consequently expression of a target protein is decreased from an mRNA with a shorter poly-A tail. As such, maintaining the length of a poly-A tail within a DNA plasmid over multiple rounds of DNA replication within host cells is beneficial. In addition, the poly-A tail may be important for translation, and maintaining a longer poly-A tail may result in improved protein expression from the mRNA.

Inclusion of one or more non-adenine nucleotides in a poly-A tail located 3' to nucleotides encoding a protein of interest may prevent the loss of one or more adenine nucleotides during DNA replication as compared to the loss that occurs in a DNA comprising a 3' poly-A tail of a similar or same length that contains only adenine nucleotides. The presence of a longer poly-A tail may also improve the efficiency of protein translation from an mRNA.

A. Adenine Nucleotides

The number of consecutive adenine nucleotides in a poly-A tail of this invention is designed to allow the poly-A-binding protein to bind to the consecutive adenosines. As used herein, "poly-A binding protein," "poly A binding protein," or "polyadenylate-binding protein" refers to a protein that binds to a poly-A tail of an mRNA. A poly-A binding protein may function to regulate translational initiation. By binding to poly-A tails, a poly-A binding protein may protect them from uridylation by ZCCHC6/ZCCHC11 and hence contribute to mRNA stability. A poly-A binding protein may be localized in cytoplasmic messenger ribonucleoprotein (mRNP) granules containing untranslated mRNAs that shuttle between the cytoplasm and the nucleus. An exemplary poly-A binding protein is PABPC1 (Uniprot Reference Number: P11940). DNA of the present invention may encode sufficient consecutive adenine nucleotides such that when transcribed into mRNA, one or more poly-A binding proteins retains ability to bind the poly-A tail. An interrupting non-adenine nucleotide anchor is placed after this functional number of consecutive adenine nucleotides.

In some embodiments, the one or more non-adenine nucleotide is positioned to interrupt the consecutive adenine nucleotides so that a poly-A binding protein can bind to a stretch of consecutive adenine nucleotides (i.e. an adenine nucleotide homopolymer or "homopolymer A". In some embodiments, the poly-A tail comprises at least 8 consecutive adenine nucleotides. In some embodiments, the at least 8 consecutive adenine nucleotides are 8, 9, 10, 11, and/or 12 consecutive nucleotides. In some embodiments, the poly-A tail comprises at least 10, 15, 20, 25, 30, 35, and/or 40 consecutive adenine nucleotides. In some embodiments, the poly-A tail comprises at least 10, 15, 20, 25, 30, 35, 40, 45, 50, 55, 60, 65, 70, 75, 80, 85, and/or 90 consecutive adenine nucleotides. A homopolymer, for example in a poly-A RNA sequence, may comprise at least 8, 9, 10, 11, 12, 13, 14, 15, 16, 17, 18, 19, 20, 21, 22, 23, 24, 25, 30, 35, or 40 consecutive adenosine nucleotides. A homopolymer, for example in a plasmid sequence encoding the poly-A tail, may comprise at least 8, 9, 10, 11, 12, 13, 14, 15, 16, 17, 18, 19, 20, 21, 22, 23, 24, 25, 30, 35, or 40 consecutive thymidine nucleotides. In some embodiments, the poly-A tail comprises two or more homopolymer A sequences of different lengths, e.g. the interrupting sequences in the poly-A tail are irregularly spaced. In some embodiments, the poly-A tail comprises regularly spaced interrupting sequences and two or more homopolymers of the same length.

In some embodiments, the poly-A tail comprises a first homopolymer sequence of at least 8 consecutive adenine nucleotides, a second homopolymer sequence of at least 5 consecutive adenine nucleotides, and an anchor comprising one or more non-adenine nucleotides.

In some embodiments, the poly-A tail comprises one or more sets of 8-50 consecutive adenine nucleotides. In some embodiments, the poly-A tail comprises one or more sets of 8-100 consecutive adenine nucleotides. For poly-A tails with multiple sets of consecutive adenine nucleotides, i.e. multiple homopolymer sequences, each set of adenine nucleotides does not need to be the same length.

In addition to the number of consecutive adenine nucleotides, a poly-A tail may also be characterized by the number of total adenine nucleotides. The number of total adenine nucleotides is simply the sum of all adenine nucleotides in a poly-A tail. All adenine nucleotides in different groups of consecutive or non-consecutive groupings of adenine nucleotides would therefore be included in the number of total adenine nucleotides in a poly-A tail.

In some embodiments, the poly-A tail comprises 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, 290-300, 300-310, 310-320, 320-330, 330-340, 340-350, 350-360, 360-370, 370-380, 380-390, 390-400, 400-410, 410-420, 420-430, 430-440, 440-450, 450-460, 460-470, 470-480, 480-490, 490-500, 500-510, 510-520, 520-530, 530-540, 540-550, 550-560, 560-570, 570-580, 580-590, or 590-600 total adenine nucleotides. In some embodiments, the poly-A tail comprises one or more homopolymer A sequence of at least 8, 9, 10, 12, 25, 30, 50 nucleotides in length.

In some embodiments, the poly-A tail comprises 40-1000, 40-900, 40-800, 40-700, 40-600, 40-500, 40-400, 40-300, 40-200, or 40-100 total adenine nucleotides.

In some embodiments, the poly-A tail comprises at least 40 total adenine nucleotides. In some embodiments, the poly-A tail comprises at least 50 total adenine nucleotides. In some embodiments, the poly-A tail comprises at least 40, 50, 60, 70 80, 90, 100, 110, 120, 130, 140, 150, 160, 170, 180, 190, 200, 220, 240, 260, 280, or 300 adenine nucleotides.

In some embodiments, the poly-A tail comprises or contains 90, 91, 92, 93, 94, 95, 96, or 97 total adenine nucleotides. In some embodiments, the poly-A tail comprises or contains 96 or 97 total adenine nucleotides.

In some embodiments, the adenine nucleotides are adenosine monophosphate. The nucleotides may be modified.

B. Interrupting Sequences Comprising Non-Adenine Nucleotides

Non-adenine nucleotides of the present invention may comprise or consist of natural or non-natural nucleotides such as guanine, cytosine, or thymine. The nucleotides may be modified.

In some embodiments, a poly-A tail comprises one non-adenine nucleotide in a poly-A tail that otherwise consists only of adenine nucleotides. The one non-adenine nucleotide may interrupt a sequence of adenine nucleotides. The one non-adenine nucleotide may be selected from guanine, cytosine, and thymine. In some embodiments, the one non-adenine nucleotide is a guanine nucleotide. In some embodiments, the one non-adenine nucleotide is a cytosine nucleotide. In some embodiments, the one non-adenine nucleotide is a thymine nucleotide. The interrupting sequence may be a mononucleotide, dinucleotide, trinucleotide sequence. The interrupting sequence may comprise 1, 2, 3, 4, 5, or more non-adenine nucleotides and it may be 1, 2, 3, 4, 5, 6, 7, 8, 9, 10, or more nucleotides in length.

In some embodiments, a single non-adenine nucleotide may interrupt sets or groups of consecutive adenine nucleotides. The one non-adenine nucleotide may be positioned to interrupt consecutive adenine nucleotides in such a way that a poly-A binding protein can bind to a stretch of consecutive adenine nucleotides.

In some embodiments, there are more than one non-adenine nucleotides in a poly-A tail. The more than one non-adenine nucleotide may be positioned to interrupt consecutive adenine nucleotides in such a way that a poly-A binding protein can bind to a stretch of consecutive adenine nucleotides. In some embodiments, non-adenine nucleotides are interspersed between more than one set of consecutive adenine nucleotides, with the number of adenine nucleotides in each series of consecutive adenine nucleotides being sufficient to allow binding of a poly-A binding protein.

The non-adenine nucleotides may be in stretches of more than one non-adenine nucleotide. The non-adenine nucleotides may be in stretches of 2-10 consecutive nucleotides that comprise one or more non-adenine nucleotides. The non-adenine nucleotides may be in interrupting sequences that are interspersed between more than one set of consecutive adenine nucleotides, e.g., more than one homopolymer A sequence. In some embodiments, the number of consecutive non-adenine nucleotides may be one, two, three, four, or five. In some embodiments, there are consecutive stretches of 2-10 non-adenine nucleotides. In some embodiments, there are consecutive stretches of 2-10 nucleotides comprising at least two non-adenine nucleotides.

The consecutive non-adenine nucleotides may be more than one of the same nucleotide or the consecutive non-adenine nucleotides may be different from each other. For example, the non-adenine nucleotides may be more than one guanine, cytosine, or thymine nucleotides. The non-adenine nucleotides may also be guanine and thymine nucleotides; guanine and cytosine nucleotides; thymine and cytosine nucleotides; or guanine, thymine and cytosine nucleotides. The non-adenine nucleotides may comprise two non-adenine nucleotide selected from one or more of guanine, cytosine, and thymine. The non-adenine nucleotide may comprise three non-adenine nucleotides selected from one or more of guanine, cytosine, and thymine. The non-adenine nucleotide may comprise more than three non-adenine nucleotides selected from one or more of guanine, cytosine, and thymine. The poly-A tail may comprise adenine nucleotides between non-adenine nucleotides at regular or irregular intervals. For example, one may view the poly-A tail as having a pattern, where the pattern is regular or irregular. The key to the pattern is the presence of one or more non-adenine nucleotide anywhere in the poly-A tail so long as there are at least 8 consecutive adenines anywhere along the length. In some embodiments, a poly-A may comprise a stretch of at least 8 consecutive adenine nucleotides anywhere along the length, where the adenine nucleotides are "interrupted" anywhere after 8 or more adenines with one or more non-adenine nucleotide. The interrupting sequence may be one non-adenine nucleotide, or 2 to 10 consecutive nucleotides, optionally comprising at least two non-adenine nucleotides. Each one or consecutive stretch of nucleotides comprising at least two non-adenine nucleotides may be followed by one or more adenines, optionally followed by one or more non-adenine nucleotides, optionally followed by one or more than one adenine nucleotides and so on until the end of the poly-A tail. This pattern of adenine nucleotides/non-adenine nucleotides may repeat at regular or irregular intervals. Alternatively, there may be no pattern, such as where there is only one or one consecutive stretch of 2-10 nucleotides, optionally comprising at least two non-adenine nucleotides along the entire length of poly-A.

II. Exemplary Patterns of Adenine and Non-Adenine Nucleotides in Poly-A Tails

Poly-A tails of this invention may comprise or consist of a number of different patterns of interrupting sequences such as consecutive adenine nucleotides and one or more non-adenine nucleotide.

A poly-A tail may begin with one or a series of consecutive adenine nucleotides followed by a non-adenine nucleotide. A poly-A tail that begins with a series of adenine nucleotides means that the 5' end of the poly-A tail consists of one or a series of consecutive adenine nucleotides with one or more non-adenine nucleotide coming after the consecutive adenine nucleotides. "After," means that the non-adenine nucleotides are 3' to a series of consecutive adenine nucleotides.

In some embodiments, the 5' end of the poly-A tail may consist of a series of consecutive adenine nucleotides followed by one or more non-adenine nucleotide(s). In some embodiments, one or more non-adenine nucleotide(s) is located after at least 8, 9, 10, 11, or 12 consecutive adenine nucleotides. In some embodiments, the one or more non-adenine nucleotide is located after at least 8-50 consecutive adenine nucleotides. In some embodiments, the one or more non-adenine nucleotide is located after at least 8-100 consecutive adenine nucleotides. In some embodiments, the non-adenine nucleotide is after one, two, three, four, five, six, or seven adenine nucleotides and is followed by at least 8 consecutive adenine nucleotides.

In some embodiments, the 5' end of the poly A tail consists of one to eight adenine nucleotides followed by one or more non-adenine nucleotide(s). In such embodiments, the non-adenine nucleotide(s) are followed by more adenine nucleotides. The adenine nucleotides that follow the one or more non-adenine nucleotide comprise at least 8 adenines nucleotides before another non-adenine nucleotide.

The range of size of a group of consecutive adenine nucleotides that begins the poly-A tail may vary. In some embodiments, the 5' end of the poly-A tail consists of 1, 2, 3 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 90, 91, 92, 93, 94, 95, 96, 97, 98, 99, or 100 consecutive adenine nucleotides. Where the first non-adenine nucleotide falls after 1-7 adenine nucleotides, the poly-A tail further comprises a stretch of at least 8 adenine nucleotides after the non-adenine nucleotide.

In some embodiments, the one or more non-adenine nucleotide is located after at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

The poly-A tail may end with a stretch of non-adenine nucleotides at the 3' end. The number of non-adenine nucleotides at the 3' end of the poly-A tail may be 1, 2, 3, 4, 5, 6, 7, 8, 9, or 10 non-adenine nucleotides. Alternatively, the 3' end of the poly-A tail may consist of one or more adenine nucleotides.

The poly-A tail of the present invention may comprise one sequence of consecutive adenine nucleotides followed by one or more non-adenine nucleotides, optionally followed by additional adenine nucleotides. The poly-A tail of the present invention may also comprise more than one sequence of consecutive adenine nucleotides interrupted by one or more non-adenine nucleotides. The sequence of consecutive adenine nucleotides may be at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides. The number of non-adenine nucleotides in an interrupting sequence may be 1, 2, 3, 4, 5, 6, 7, 8, 9, or 10 non-adenine nucleotides.

A poly-A tail of the invention may also comprise more than one series of consecutive adenine nucleotides that are interrupted or interspersed with non-adenine nucleotides. The length of the interrupting sequence may be 1, 2, 3, 4, 5, 6, 7, 8, 9, or 10 nucleotides. The length of the interrupting sequence may be 1-3, 1-5, 1-10, 2-10, 2-8, 2-6, or 2-5 nucleotides. The poly-A tails of the invention may comprise more than one set of consecutive adenine nucleotides and an interrupting sequence comprising one non-adenine nucleotide or more than one consecutive stretch of 2-10 non-adenine nucleotides between each set of consecutive adenine nucleotides. The poly-A tails of the invention may comprise more than one set of consecutive adenine nucleotides and one non-adenine nucleotide or more than one consecutive stretch of 2-10 nucleotides comprising at least two non-adenine nucleotides between each set of consecutive adenine nucleotides. The poly-A tails of the invention may comprise more than one set of consecutive adenine nucleotides and one or more interrupting sequences, each comprising one or more non-adenine nucleotide. The sets may each comprise the same or different number of adenine nucleotides. In embodiments with multiple sets of consecutive adenine nucleotides, each set of consecutive adenine nucleotides may be sufficient in length to allow binding of a poly-A binding protein.

In some embodiments, one or more non-adenine nucleotide is an interrupting sequence located at regular intervals with the poly-A tail. By regular intervals, it is meant that a set number of consecutive adenine nucleotides is followed by non-adenine nucleotides in a repeated fashion.

In some embodiments, one or more non-adenine nucleotide is located at irregular intervals with the poly-A tail. By irregular intervals, it is meant that a set number of consecutive adenine nucleotides is followed by non-adenine nucleotides followed by another set of consecutive adenine nucleotides that comprise a different number of adenines than the first set.

In some embodiments, the poly-A tail comprises or contains one non-adenine nucleotide or one consecutive stretch of 2-10 nucleotides non-adenine nucleotides every 8-50 consecutive adenine nucleotides. In some embodiments, the poly-A tail comprises or contains one non-adenine nucleotide or one consecutive stretch of 2-10 non-adenine nucleotides every 8-50 consecutive adenine nucleotides. In some embodiments, the poly-A tail comprises or contains one non-adenine nucleotide or one consecutive stretch of 2-10 nucleotides non-adenine nucleotides every 8-100 consecutive adenine nucleotides. In some embodiments, the poly-A tail comprises or contains one non-adenine nucleotide or one consecutive stretch of 2-10 non-adenine nucleotides every 8-100 consecutive adenine nucleotides.

In some embodiments, the poly-A tail comprises or contains one non-adenine nucleotide or one consecutive stretch of 2-10 nucleotides comprising at least two non-adenine nucleotides every 8-50 consecutive adenine nucleotides. In some embodiments, the poly-A tail comprises or contains one non-adenine nucleotide or one consecutive stretch of 2-10 nucleotides comprising at least two non-adenine nucleotides every 8-50 consecutive adenine nucleotides. In some embodiments, the poly-A tail comprises or contains one non-adenine nucleotide or one consecutive stretch of 2-10 nucleotides comprising at least two non-adenine nucleotides every 8-100 consecutive adenine nucleotides. In some embodiments, the poly-A tail comprises or contains one non-adenine nucleotide or one consecutive stretch of 2-10 nucleotides comprising at least two non-adenine nucleotides every 8-100 consecutive adenine nucleotides.

In some embodiments, the poly-A tail comprises or contains one non-adenine nucleotide or one consecutive stretch of 2-10 nucleotides comprising a non-adenine nucleotide every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

In some embodiments, the poly-A tail comprises or contains one non-adenine nucleotide or one consecutive stretch of 2-10 nucleotides comprising at least two non-adenine nucleotides every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

In some embodiments, number of non-adenine nucleotides may be 1, 2, 3, 4, or 5 consecutive non-adenine nucleotides. In some embodiments, the number of consecutive adenine nucleotides may be 8-50 adenine nucleotides.

In some embodiment embodiments, the poly-A tail comprises or contains 1, 2, 3, 4, or 5 consecutive non-adenine nucleotides every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

The numbers of consecutive adenine nucleotides in a poly-A tail may be 12, 16, 25, 30, or 39. The number of consecutive adenine nucleotides may also be greater than 39. In some embodiments, the poly-A tail comprises or contains 1, 2, 3, 4, or 5 consecutive non-adenine nucleotides every 12 consecutive adenine nucleotides. In some embodiments, the poly-A tail comprises or contains 1, 2, 3, 4, or 5 consecutive non-adenine nucleotides every 16 consecutive adenine nucleotides. In some embodiments, the poly-A tail comprises or contains 1, 2, 3, 4, or 5 consecutive non-adenine nucleotides every 25 consecutive adenine nucleotides. In some embodiments, the poly-A tail comprises or contains 1, 2, 3, 4, or 5 consecutive non-adenine nucleotides every 30 consecutive adenine nucleotides. In some embodiments, the poly-A tail comprises or contains 1, 2, 3, 4, or 5 consecutive non-adenine nucleotides every 39 consecutive adenine nucleotides. The number of consecutive non-adenine nucleotides may also be greater than 5.

Exemplary trinucleotide interrupting sequences include GCG, CCG, GTG, TGG, CGG, GGT, TAT, CAT, CGT, CTC, GAT, CCT, TGT, CGC, CAC, TGC, TCG, TCT, CCC, GAC, TAG, GTT, CTG, and TTT. There are 63 possible trinucleotide interrupting sequences, and 36 trinucleotide interrupting sequences that omit a terminal A. In some embodiments, the poly-A tail comprises one or more trinucleotide interrupting sequences chosen from TGG, CGG, GGT, TAT, CAT, CGT, CTC, GAT, CCT, TGT, CGC, CAC, TGC, TCG, TCT, CCC, GAC, TAG, GTT, CTG, and TTT. In some embodiments, the poly-A tail comprises multiple interrupting sequences designed to minimize hybridization and annealing between 3 or more nucleotides within the sequence encoding the poly-A tail or within the poly-A tail. In certain embodiments, the interrupting sequences that minimize annealing between 3 or more nucleotides are chosen from the 34 trinucleotide interrupting sequences that omit a terminal A. In some embodiments, the interrupting sequences that minimize annealing between 3 or more nucleotides are chosen from TGG, CGG, GGT, TAT, CAT, CGT, CTC, GAT, CCT, TGT, CGC, CAC, TGC, TCG, TCT, CCC, GAC, TAG, GTT, CTG, and TTT. In some embodiments, e.g. SEQ ID NO: 18, the poly-A tail comprises di- and/or tri-nucleotide interrupting sequences chosen from TGG, CGG, GGT, TAT, CAT, CGT, CTC, GAT, CCT, TGT, CGC, CAC, TGC, TCG, TCT, CCC, GAC, TAG, GTT, CTG, TTT, and CG. In certain embodiments, the poly-A tail comprises trinucleotide interrupting sequences chosen from GCG, CCG, and GTG. Exemplary dinucleotide interrupting sequences include CG, GC, CC, GG, TT, CT, TC, GT, and TG. There are 15 possible dinucleotide interrupting sequences, and 9 dinucleotides that do not include a terminal A. Mononucleotide interrupting sequences can be C, G, and T. Note that, with respect to any nucleotide sequence above, when referring to an RNA sequence (such as an mRNA), as opposed to a DNA sequence, T is replaced by U.

One skilled in the art would be able to design a number of different patterns of DNA encoding poly-A tails with consecutive adenine nucleotides and one or more non-adenine nucleotide. Some exemplary poly-A tails comprising at least 8 consecutive adenine nucleotides and one or more adenine-nucleotide are presented, for example, in SEQ ID Nos: 1-5, 10, 11, and 18.

III. Methods of Use

The DNA of this invention may be used for production of mRNA encoded by the DNA. In some embodiments, an mRNA is encoded by the DNA of the invention.

In some embodiments, the DNA of the invention is prepared for production of mRNA. In some embodiments, the DNA is within a vector. In some embodiments, the vector is within a host cell. In some embodiments, an mRNA encoded by the DNA of this invention is used for translating the protein of interest encoded by the DNA.

In some embodiments, the one or more non-adenine nucleotide prevents the loss of one or more adenine nucleotides during DNA replication as compared to the loss that occurs in a DNA comprising a 3' tail of a similar or same length that contains only adenine nucleotides. DNA replication is a necessary step in growth of plasmid for DNA purification. As such, a plasmid comprising the DNA of this invention encoding a poly-A tail comprising at least 8 consecutive adenine nucleotides and one or more non-adenine nucleotide may show improved stability over one or more rounds of growth and purification of the plasmid, as compared to a plasmid encoding a poly-A tail consisting only of adenine nucleotides.

A plasmid comprising the DNA of this invention comprising a sequence encoding a poly-A tail comprising at least 8 consecutive adenine nucleotides and one or more non-adenine nucleotide may have greater stability when grown in a host cell compared to a plasmid comprising a DNA comprising a sequence encoding a poly-A tail consisting only of consecutive adenine nucleotides. During growth of the host cell expressing a plasmid with a DNA sequence, a DNA sequence encoding a poly-A tail that comprises consecutive adenine nucleotides and one or more non-adenine nucleotide may be resistant to a decrease in length of the DNA encoding the poly-A tail compared to a poly-A tail consisting only of adenine nucleotides. In some embodiments, a plasmid comprising a DNA encoding a poly-A tail comprising one or more non-adenine nucleotide prevents loss of adenines during growth of a host cell as compared to a plasmid comprising a DNA encoding a poly-A tail comprising only adenine nucleotides.

Any means of growing and purifying a vector known to one skilled in the art may be used for growth of a host cell encoding a plasmid. The process of growth and purification of a vector may also be referred to as plasmid preparation. Standard steps of plasmid purification include growth of a bacterial culture, harvesting and lysis of the bacteria, and purification of plasmid DNA. Many kits are available from various manufacturers to purify plasmid DNA. The step of plasmid preparation may be minipreparation (with expected yield of 20 to 40 µg or 50 to 100 µg of plasmid DNA), midipreparation (with expected yield of 100 to 350 µg of plasmid DNA), maxipreparation (with expected yield of 500-850 µg of plasmid DNA), megapreparation (with expected yield of 1.5-2.5 mg of plasmid DNA), or gigapreparation (with expected yield of 7.5-10 mg of plasmid DNA). For therapeutic mRNA production, plasmids may be produced at scales of 100 mg, 1 g, 10 g, or more. The increased stability and replication efficiency of plasmids encoding poly-A tails with non-adenine nucleotides as described herein may improve the consistency and efficiency of plasmids made at such scales.

In some embodiments, a method of producing mRNA from a DNA vector of the present invention is encompassed. In some embodiments, the method of producing mRNA from the DNA vector comprises linearizing the vector downstream of the poly-A tail; denaturing the linearized vector; and contacting the denaturized DNA with an RNA polymerase in the presence of RNA nucleotides such as guanine, cytosine, uracil, adenine, or chemically modified version of such nucleotides such as pseudouridine, N-1-methyl pseudouridine, methoxyuridine, among others. Modified residues, such as base, sugar, and backbone modifications of nucleotide residues can be used in the mRNAs, polynucleotides, and methods described herein.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

DESCRIPTION OF SEQUENCES

This table provides a listing of certain sequences referenced herein. Note again that, when referring to the RNA version of a DNA sequence in the table below, T is replaced by U. When referring to a DNA version of an RNA sequence in the table below, U is replaced by T.

TABLE 1

| Description | Sequence | SEQ ID No |
|---|---|---|
| sequence of an exemplary poly-A tail comprising non-adenine nucleotides with 30, 30, and 39 consecutive adenosines and ending with non-adenine nucleotides | AAAAAAAAAA AAAAAAAAAA AAAAAAAAAA GCGAAAAAAA AAAAAAAAAA AAAAAAAAAA AAACCGAAAA AAAAAAAAAA AAAAAAAAAA AAAAAAAAAA AAAAACCC | 1 |
| 30PA - sequence of an exemplary poly-A tail comprising non-adenine nucleotides with 30, 30, and 39 consecutive adenosines | AAAAAAAAAA AAAAAAAAAA AAAAAAAAAA GCGAAAAAAA AAAAAAAAAA AAAAAAAAAA AAACCGAAAA AAAAAAAAAA AAAAAAAAAA AAAAAAAAAA AAAA | 2 |
| 25PA - sequence of an exemplary poly-A tail comprising non-adenine nucleotides with four sets of 25 consecutive adenosines | AAAAAAAAAA AAAAAAAAAA AAAAAGCGAA AAAAAAAAAA AAAAAAAAAA AAACCGAAAA AAAAAAAAAA AAAAAAAAAA AGTGAAAAAA AAAAAAAAAA AAAAAAAA | 3 |
| 16PA - sequence of an exemplary poly-A tail comprising non-adenine nucleotides with six sets of 16 consecutive adenosines | AAAAAAAAAA AAAAAGAAA AAAAAAAAAA AAACAAAAAA AAAAAAAAAA TAAAAAAAAA AAAAAAATAA AAAAAAAAAA AAAACAAAAA AAAAAAAAAA A | 4 |
| 16PA long - sequence of an exemplary poly-A tail comprising non-adenine nucleotides with six sets of 16 consecutive adenosines and 63 consecutive adenosines | AAAAAAAAAA AAAAAGAAA AAAAAAAAAA AAACAAAAAA AAAAAAAAAA TAAAAAAAAA AAAAAAATAA AAAAAAAAAA AAAACAAAAA AAAAAAAAAA ACAAAAAAAA AAAAAAAAAA AAAAAAAAAA AAAAAAAAAA AAAAAAAAAA AAAAA | 5 |
| Cas9 mRNA with a poly-A tail consisting of 97 adenosines | TAATACGACTCACTATAGGGTCCCGCAGTCGGCGTCCAGC GGCTCTGCTTGTTCGTGTGTGTGTCGTTGCAGGCCTTATT CGGATCCATGGATAAGAAGTACTCAATCGGGCTGGATATC GGAACTAATTCCGTGGGTTGGGCAGTGATCACGGATGAAT ACAAAGTGCCGTCCAAGAAGTTCAAGGTCCTGGGGAACAC CGATAGACACAGCATCAAGAAAAATCTCATCGGAGCCCTG CTGTTTGACTCCGGCGAAACCGCAGAAGCGACCCGGCTCA AACGTACCGCGAGGCGACGCTACACCCGGCGGAAGAATCG CATCTGCTATCTGCAAGAGATCTTTTCGAACGAAATGGCA AAGGTCGACGACAGCTTCTTCCACCGCCTGGAAGAATCTT TCCTGGTGGAGGAGGACAAGAAGCATGAACGGCATCCTAT CTTTGGAAACATCGTCGACGAAGTGGCGTACCACGAAAAG TACCCGACCATCTACCATCTGCGGAAGAAGTTGGTTGACT CAACTGACAAGGCCGACCTCAGATTGATCTACTTGGCCCT | 6 |

TABLE 1-continued

| Description | Sequence | SEQ ID No |
|---|---|---|
| | CGCCCATATGATCAAATTCCGCGGACACTTCCTGATCGAA | |
| | GGCGATCTGAACCCTGATAACTCCGACGTGGATAAGCTTT | |
| | TCATTCAACTGGTGCAGACCTACAACCAACTGTTCGAAGA | |
| | AAACCCAATCAATGCTAGCGGCGTCGATGCCAAGGCCATC | |
| | CTGTCCGCCCGGCTGTCGAAGTCGCGGCGCCTCGAAAACC | |
| | TGATCGCACAGCTGCCGGGAGAGAAAAAGAACGGACTTTT | |
| | CGGCAACTTGATCGCTCTCTCACTGGGACTCACTCCCAAT | |
| | TTCAAGTCCAATTTTGACCTGGCCGAGGACGCGAAGCTGC | |
| | AACTCTCAAAGGACACCTACGACGACGACTTGGACAATTT | |
| | GCTGGCACAAATTGGCGATCAGTACGCGGATCTGTTCCTT | |
| | GCCGCTAAGAACCTTTCGGACGCAATCTTGCTGTCCGATA | |
| | TCCTGCGCGTGAACACCGAAATAACCAAAGCGCCGCTTAG | |
| | CGCCTCGATGATTAAGCGGTACGACGAGCATCACCAGGAT | |
| | CTCACGCTGCTCAAAGCGCTCGTGAGACAGCAACTGCCTG | |
| | AAAAGTACAAGGAGATCTTCTTCGACCAGTCCAAGAATGG | |
| | GTACGCAGGGTACATCGATGGAGGCGCTAGCCAGGAAGAG | |
| | TTCTATAAGTTCATCAAGCCAATCCTGGAAAAGATGGACG | |
| | GAACCGAAGAACTGCTGGTCAAGCTGAACAGGGAGGATCT | |
| | GCTCCGGAAACAGAGAACCTTTGACAACGGATCCATTCCC | |
| | CACCAGATCCATCTGGGTGAGCTGCACGCCATCTTGCGGC | |
| | GCCAGGAGGACTTTTACCCATTCCTCAAGGACAACCGGGA | |
| | AAAGATCGAGAAAATTCTGACGTTCCGCATCCCGTATTAC | |
| | GTGGGCCCACTGGCGCGCGGCAATTCGCGCTTCGCGTGGA | |
| | TGACTAGAAAATCAGAGGAAACCATCACTCCTTGGAATTT | |
| | CGAGGAAGTTGTGGATAAGGGAGCTTCGGCACAAAGCTTC | |
| | ATCGAACGAATGACCAACTTCGACAAGAATCTCCCAAACG | |
| | AGAAGGTGCTTCCTAAGCACAGCCTCCTTTACGAATACTT | |
| | CACTGTCTACAACGAACTGACTAAAGTGAAATACGTTACT | |
| | GAAGGAATGAGGAAGCCGGCCTTTCTGTCCGGAGAACAGA | |
| | AGAAAGCAATTGTCGATCTGCTGTTCAAGACCAACCGCAA | |
| | GGTGACCGTCAAGCAGCTTAAAGAGGACTACTTCAAGAAG | |
| | ATCGAGTGTTTCGACTCAGTGGAAATCAGCGGGGTGGAGG | |
| | ACAGATTCAACGCTTCGCTGGGAACCTATCATGATCTCCT | |
| | GAAGATCATCAAGGACAAGGACTTCCTTGACAACGAGGAG | |
| | AACGAGGACATCCTGGAAGATATCGTCCTGACCTTGACCC | |
| | TTTTCGAGGATCGCGAGATGATCGAGGAGAGGCTTAAGAC | |
| | CTACGCTCATCTCTTCGACGATAAGGTCATGAAACAACTC | |
| | AAGCGCCGCCGGTACACTGGTTGGGGCCGCCTCTCCCGCA | |
| | AGCTGATCAACGGTATTCGCGATAAACAGAGCGGTAAAAC | |
| | TATCCTGGATTTCCTCAAATCGGATGGCTTCGCTAATCGT | |
| | AACTTCATGCAATTGATCCACGACGACAGCCTGACCTTTA | |
| | AGGAGGACATCCAAAAAGCACAAGTGTCCGGACAGGGAGA | |
| | CTCACTCCATGAACACATCGCGAATCTGGCCGGTTCGCCG | |
| | GCGATTAAGAAGGGAATTCTGCAAACTGTGAAGGTGGTCG | |
| | ACGAGCTGGTGAAGGTCATGGGACGGCACAAACCGGAGAA | |
| | TATCGTGATTGAAATGGCCCGAGAAAACCAGACTACCCAG | |
| | AAGGGCCAGAAAAACTCCCGCGAAAGGATGAAGCGGATCG | |
| | AAGAAGGAATCAAGGAGCTGGGCAGCCAGATCCTGAAAGA | |
| | GCACCCGGTGGAAAACACGCAGCTGCAGAACGAGAAGCTC | |
| | TACCTGTACTATTTGCAAAATGGACGGGACATGTACGTGG | |
| | ACCAAGAGCTGGACATCAATCGGTTGTCTGATTACGACGT | |
| | GGACCACATCGTTCCACAGTCCTTTCTGAAGGATGACTCG | |
| | ATCGATAACAAGGTGTTGACTCGCAGCGACAAGAACAGAG | |
| | GGAAGTCAGATAATGTGCCATCGGAGGAGGTCGTGAAGAA | |
| | GATGAAGAATTACTGGCGGCAGCTCCTGAATGCGAAGCTG | |
| | ATTACCCAGAGAAAGTTTGACAATCTCACTAAAGCCGAGC | |
| | GCGGCGGACTCTCAGAGCTGGATAAGGCTGGATTCATCAA | |
| | ACGGCAGCTGGTCGAGACTCGGCAGATTACCAAGCACGTG | |
| | GCGCAGATCTTGGACTCCCGCATGAACACTAAATACGACG | |
| | AGAACGATAAGCTCATCCGGGAAGTGAAGGTGATTACCCT | |
| | GAAAAGCAAACTTGTGTCGGACTTTCGGAAGGACTTTCAG | |
| | TTTTACAAAGTGAGAGAAATCAACAACTACCATCACGCGC | |
| | ATGACGCATACCTCAACGCTGTGGTCGGTACCGCCCTGAT | |
| | CAAAAAGTACCCTAAACTTGAATCGGAGTTTGTGTACGGA | |
| | GACTACAAGGTCTACGACGTGAGGAAGATGATAGCCAAGT | |
| | CCGAACAGGAAATCGGGAAAGCAACTGCGAAATACTTCTT | |
| | TTACTCAAACATCATGAACTTTTTCAAGACTGAAATTACG | |
| | CTGGCCAATGGAGAAATCAGGAAGAGGCCACTGATCGAAA | |
| | CTAACGGAGAAACGGGCGAAATCGTGTGGGACAAGGGCAG | |
| | GGACTTCGCAACTGTTCGCAAAGTGCTCTCTATGCCGCAA | |
| | GTCAATATTGTGAAGAAAACCGAAGTGCAAACCGGCGGAT | |
| | TTTCAAAGGAATCGATCCTCCCAAAGAGAAATAGCGACAA | |
| | GCTCATTGCACGCAAGAAAGACTGGGACCCGAAGAAGTAC | |
| | GGAGGATTCGATTCGCCGACTGTCGCATACTCCGTCCTCG | |
| | TGGTGGCCAAGGTGGAGAAGGGAAAGAGCAAAAAGCTCAA | |
| | ATCCGTCAAAGAGCTGCTGGGGATTACCATCATGGAACGA | |
| | TCCTCGTTCGAGAAGAACCCGATTGATTTCCTCGAGGCGA | |

TABLE 1-continued

| Description | Sequence | SEQ ID No |
|---|---|---|
| | AGGGTTACAAGGAGGTGAAGAAGGATCTGATCATCAAACT<br>CCCCAAGTACTCACTGTTCGAACTGGAAAATGGTCGGAAG<br>CGCATGCTGGCTTCGGCCGGAGAACTCCAAAAAGGAAATG<br>AGCTGGCCTTGCCTAGCAAGTACGTCAACTTCCTCTATCT<br>TGCTTCGCACTACGAAAAACTCAAAGGGTCACCGGAAGAT<br>AACGAACAGAAGCAGCTTTTCGTGGAGCAGCACAAGCATT<br>ATCTGGATGAAATCATCGAACAAATCTCCGAGTTTTCAAA<br>GCGCGTGATCCTCGCCGACGCCAACCTCGACAAAGTCCTG<br>TCGGCCTACAATAAGCATAGAGATAAGCCGATCAGAGAAC<br>AGGCCGAGAACATTATCCACTTGTTCACCCTGACTAACCT<br>GGGAGCCCCAGCCGCCTTCAAGTACTTCGATACTACTATC<br>GATCGCAAAGATACACGTCCACCAAGGAAGTTCTGGACG<br>CGACCCTGATCCACCAAAGCATCACTGGACTCTACGAAAC<br>TAGGATCGATCTGTCGCAGCTGGGTGGCGATGGCGGTGGA<br>TCTCCGAAAAAGAAGAGAAAGGTGTAATGAGCTAGCCATC<br>ACATTTAAAAGCATCTCAGCCTACCATGAGAATAAGAGAA<br>AGAAAATGAAGATCAATAGCTTATTCATCTCTTTTTCTTT<br>TTCGTTGGTGTAAAGCCAACACCCTGTCTAAAAAACATAA<br>ATTTCTTTAATCATTTTGCCTCTTTTCTCTGTGCTTCAAT<br>TAATAAAAAATGGAAAGAACCTCGAGAAAAAAAAAAAAAA<br>AAAAAAAAAAAAAAAAAAAAAAAAAAAAAAAAAAAAAAAA<br>AAAAAAAAAAAAAAAAAAAAAAAAAAAAAAAAAAAAAAAA<br>AAA | |
| T7 promoter and Cas9 mRNA with a poly-A tail comprising SEQ ID NO: 1 | TAATACGACT CACTATAGGG TCCCGCAGTC<br>GGCGTCCAGC GGCTCTGCTT GTTCGTGTGT<br>GTGTCGTTGC AGGCCTTATT CGGATCTGCC<br>ACCATGGATA AGAAGTACTC GATCGGGCTG<br>GATATCGGAA CTAATTCCGT GGGTTGGGCA<br>GTGATCACGG ATGAATACAA AGTGCCGTCC<br>AAGAAGTTCA AGGTCCTGGG GAACACCGAT<br>AGACACAGCA TCAAGAAGAA TCTCATCGGA<br>GCCCTGCTGT TTGACTCCGG CGAAACCGCA<br>GAAGCGACCC GGCTCAAACG TACCGCGAGG<br>CGACGCTACA CCCGGCGGAA GAATCGCATC<br>TGCTATCTGC AAGAAATCTT TTCGAACGAA<br>ATGGCAAAGG TGGACGACAG CTTCTTCCAC<br>CGCCTGGAAG AATCTTTCCT GGTGGAGGAG<br>GACAAGAAGC ATGAACGGCA TCCTATCTTT<br>GGAAACATCG TGGACGAAGT GGCGTACCAC<br>GAAAAGTACC CGACCATCTA CCATCTGCGG<br>AAGAAGTTGG TTGACTCAAC TGACAAGGCC<br>GACCTCAGAT TGATCTACTT GGCCCTCGCC<br>CATATGATCA AATTCCGCGG ACACTTCCTG<br>ATCGAAGGCG ATCTGAACCC TGATAACTCC<br>GACGTGGATA AGCTGTTCAT TCAACTGGTG<br>CAGACCTACA ACCAACTGTT CGAAGAAAAC<br>CCAATCAATG CCAGCGGCGT CGATGCCAAG<br>GCCATCCTGT CCGCCCGGCT GTCGAAGTCG<br>CGGCGCCTCG AAAACCTGAT CGCACAGCTG<br>CCGGGAGAGA AGAAGAACGG ACTTTTCGGC<br>AACTTGATCG CTCTCTCACT GGGACTCACT<br>CCCAATTTCA AGTCCAATTT TGACCTGGCC<br>GAGGACGCGA AGCTGCAACT CTCAAAGGAC<br>ACCTACGACG ACGACTTGGA CAATTTGCTG<br>GCACAAATTG GCGATCAGTA CGCGGATCTG<br>TTCCTTGCCG CTAAGAACCT TTCGGACGCA<br>ATCTTGCTGT CCGATATCCT GCGCGTGAAC<br>ACCGAAATAA CCAAAGCGCC GCTTAGCGCC<br>TCGATGATTA AGCGGTACGA CGAGCATCAC<br>CAGGATCTCA CGCTGCTCAA AGCGCTCGTG<br>AGACAGCAAC TGCCTGAAAA GTACAAGGAG<br>ATTTTCTTCG ACCAGTCCAA GAATGGGTAC<br>GCAGGGTACA TCGATGGAGG CGCCAGCCAG<br>GAAGAGTTCT ATAAGTTCAT CAAGCCAATC<br>CTGGAAAAGA TGGACGGAAC CGAAGAACTG<br>CTGGTCAAGC TGAACAGGGA GGATCTGCTC<br>CGCAAACAGA GAACCTTTGA CAACGGAAGC<br>ATTCCACACC AGATCCATCT GGGTGAGCTG<br>CACGCCATCT TGCGGCGCCA GGAGGACTTT<br>TACCCATTCC TCAAGGACAA CCGGGAAAAG<br>ATCGAGAAAA TTCTGACGTT CCGCATCCCG<br>TATTACGTGG CCCACTGGC GCGCGGCAAT<br>TCGCGCTTCG CGTGGATGAC TAGAAAATCA<br>GAGGAAACCA TCACTCCTTG GAATTTCGAG<br>GAAGTTGTGG ATAAGGGAGC TTCGGCACAA<br>TCCTTCATCG AACGAATGAC CAACTTCGAC | 7 |

TABLE 1-continued

| Description | Sequence | SEQ ID No |
|---|---|---|
| | AAGAATCTCC CAAACGAGAA GGTGCTTCCT | |
| | AAGCACAGCC TCCTTTACGA ATACTTCACT | |
| | GTCTACAACG AACTGACTAA AGTGAAATAC | |
| | GTTACTGAAG GAATGAGGAA GCCGGCCTTT | |
| | CTGAGCGGAG AACAGAAGAA AGCGATTGTC | |
| | GATCTGCTGT TCAAGACCAA CCGCAAGGTG | |
| | ACCGTCAAGC AGCTTAAAGA GGACTACTTC | |
| | AAGAAGATCG AGTGTTTCGA CTCAGTGGAA | |
| | ATCAGCGGAG TGGAGGACAG ATTCAACGCT | |
| | TCGCTGGGAA CCTATCATGA TCTCCTGAAG | |
| | ATCATCAAGG ACAAGGACTT CCTTGACAAC | |
| | GAGGAGAACG AGGACATCCT GGAAGATATC | |
| | GTCCTGACCT TGACCCTTTT CGAGGATCGC | |
| | GAGATGATCG AGGAGAGGCT TAAGACCTAC | |
| | GCTCATCTCT TCGACGATAA GGTCATGAAA | |
| | CAACTCAAGC GCCGCCGGTA CACTGGTTGG | |
| | GGCCGCCTCT CCCGCAAGCT GATCAACGGT | |
| | ATTCGCGATA AACAGAGCGG TAAAACTATC | |
| | CTGGATTTCC TCAAATCGGA TGGCTTCGCT | |
| | AATCGTAACT TCATGCAGTT GATCCACGAC | |
| | GACAGCCTGA CCTTTAAGGA GGACATCCAG | |
| | AAAGCACAAG TGAGCGGACA GGGAGACTCA | |
| | CTCCATGAAC ACATCGCGAA TCTGGCCGGT | |
| | TCGCCGGCGA TTAAGAAGGG AATCCTGCAA | |
| | ACTGTGAAGG TGGTGGACGA GCTGGTGAAG | |
| | GTCATGGGAC GGCACAAACC GGAGAATATC | |
| | GTGATTGAAA TGGCCCGAGA AAACCAGACT | |
| | ACCCAGAAGG GCCAGAAGAA CTCCCGCGAA | |
| | AGGATGAAGC GGATCGAAGA AGGAATCAAG | |
| | GAGCTGGGCA GCCAGATCCT GAAAGAGCAC | |
| | CCGGTGGAAA ACACGCAGCT GCAGAACGAG | |
| | AAGCTCTACC TGTACTATTT GCAAAATGGA | |
| | CGGGACATGT ACGTGGACCA AGAGCTGGAC | |
| | ATCAATCGGT TGTCTGATTA CGACGTGGAC | |
| | CACATCGTTC CACAGTCCTT TCTGAAGGAT | |
| | GACTCCATCG ATAACAAGGT GTTGACTCGC | |
| | AGCGACAAGA ACAGAGGGAA GTCAGATAAT | |
| | GTGCCATCGG AGGAGGTCGT GAAGAAGATG | |
| | AAGAATTACT GGCGGCAGCT CCTGAATGCG | |
| | AAGCTGATTA CCCAGAGAAA GTTTGACAAT | |
| | CTCACTAAAG CCGAGCGCGG CGGACTCTCA | |
| | GAGCTGGATA AGGCTGGATT CATCAAACGG | |
| | CAGCTGGTCG AGACTCGGCA GATTACCAAG | |
| | CACGTGGCGC AGATCCTGGA CTCCCGCATG | |
| | AACACTAAAT ACGACGAGAA CGATAAGCTC | |
| | ATCCGGGAAG TGAAGGTGAT TACCCTGAAA | |
| | AGCAAACTTG TGTCGGACTT TCGGAAGGAC | |
| | TTTCAGTTTT ACAAAGTGAG AGAAATCAAC | |
| | AACTACCATC ACGCGCATGA CGCATACCTC | |
| | AACGCTGTGG TCGGCACCGC CCTGATCAAG | |
| | AAGTACCCTA AACTTGAATC GGAGTTTGTG | |
| | TACGGAGACT ACAAGGTCTA CGACGTGAGG | |
| | AAGATGATAG CCAAGTCCGA ACAGGAAATC | |
| | GGGAAAGCAA CTGCGAAATA CTTCTTTTAC | |
| | TCAAACATCA TGAACTTCTT CAAGACTGAA | |
| | ATTACGCTGG CCAATGGAGA AATCAGGAAG | |
| | AGGCCACTGA TCGAAACTAA CGGAGAAACG | |
| | GGCGAAATCG TGTGGGACAA GGGCAGGGAC | |
| | TTCGCAACTG TTCGCAAAGT GCTCTCTATG | |
| | CCGCAAGTCA ATATTGTGAA GAAAACCGAA | |
| | GTGCAAACCG GCGGATTTTC AAAGGAATCG | |
| | ATCCTCCCAA AGAGAAATAG CGACAAGCTC | |
| | ATTGCACGCA AGAAAGACTG GGACCCGAAG | |
| | AAGTACGGAG GATTCGATTC GCCGACTGTC | |
| | GCATACTCCG TCCTCGTGGT GGCCAAGGTG | |
| | GAGAAGGGAA AGAGCAAGAA GCTCAAATCC | |
| | GTCAAAGAGC TGCTGGGGAT TACCATCATG | |
| | GAACGATCCT CGTTCGAGAA GAACCCGATT | |
| | GATTTCCTGG AGGCGAAGGG TTACAAGGAG | |
| | GTGAAGAAGG ATCTGATCAT CAAACTGCCC | |
| | AAGTACTCAC TGTTCGAACT GGAAAATGGT | |
| | CGGAAGCGCA TGCTGGCTTC GGCCGGAGAA | |
| | CTCCAGAAAG GAAATGAGCT GGCCTTGCCT | |
| | AGCAAGTACG TCAACTTCCT CTATCTTGCT | |
| | TCGCACTACG AGAAACTCAA AGGGTCACCG | |
| | GAAGATAACG AACAGAAGCA GCTTTTCGTG | |
| | GAGCAGCACA AGCATTATCT GGATGAAATC | |

TABLE 1-continued

| Description | Sequence | SEQ ID No |
|---|---|---|
| | ATCGAACAAA TCTCCGAGTT TTCAAAGCGC<br>GTGATCCTCG CCGACGCCAA CCTCGACAAA<br>GTCCTGTCGG CCTACAATAA GCATAGAGAT<br>AAGCCGATCA GAGAACAGGC CGAGAACATT<br>ATCCACTTGT TCACCCTGAC TAACCTGGGA<br>GCTCCAGCCG CCTTCAAGTA CTTCGATACT<br>ACTATCGACC GCAAAAGATA CACGTCCACC<br>AAGGAAGTTC TGGACGCGAC CCTGATCCAC<br>CAAAGCATCA CTGGACTCTA CGAAACTAGG<br>ATCGATCTGT CGCAGCTGGG TGGCGATGGT<br>GGCGGTGGAT CCTACCCATA CGACGTGCCT<br>GACTACGCCT CCGGAGGTGG TGGCCCCAAG<br>AAGAAACGGA AGGTGTGATA GCTAGCCATC<br>ACATTTAAAA GCATCTCAGC CTACCATGAG<br>AATAAGAGAA AGAAAATGAA GATCAATAGC<br>TTATTCATCT CTTTTTCTTT TTCGTTGGTG<br>TAAAGCCAAC ACCCTGTCTA AAAAACATAA<br>ATTTCTTTAA TCATTTTGCC TCTTTTCTCT<br>GTGCTTCAAT TAATAAAAA TGGAAAGAAC<br>CTCGAGAAAA AAAAAAAAAA AAAAAAAAAA<br>AAAAAAGCGA AAAAAAAAAA AAAAAAAAAA<br>AAAAAAAAAC CGAAAAAAAA AAAAAAAAAA<br>AAAAAAAAAA AAAAAAAAAA A | |
| Single guide RNA targeting SEAP | mC*mU*mC*C CUGAUGGAGA UGACAGGUUU<br>UAGAmGmCmU mAmGmAmAmA mUmAmGmCAA<br>GUUAAAAUAA GGCUAGUCCG UUAUCAmAmC<br>mUmUmGmAm mAmAmAmGmU mGmGmCmAmC<br>mCmGmAmGmU mCmGmGmUmG<br>mCmU*mU*mU *mU | 8 |
| Single guide RNA targeting mouse TTR | mU*mU*mA*CAGCCACGUCUACAGCAGUUUUAGAmGmCmU<br>mAmGmAmAm<br>AmUmAmGmCAAGUUAAAAUAAGGCUAGUCCGUUAUCAmAm<br>CmUmUmGm<br>AmAmAmAmGmUmGmGmCmAmCmCmGmAmGmUmCmGmGm<br>UmGmCmU*<br>mU*mU*mU | 9 |
| 12PA - sequence of an exemplary poly-A tail comprising non-adenine nucleotides with nine sets of 12 consecutive adenosines and mononucleotide interrupting sequences | AAAAAAAAAAAATAAAAAAAAAAAATAAAAAAAAAAAACA<br>AAAAAAAAAAATAAAAAAAAAAAACAAAAAAAAAAAGAA<br>AAAAAAAAACAAAAAAAAAAAATAAAAAAAAAAAA | 10 |
| 8PA - sequence of an exemplary poly-A tail comprising non-adenine nucleotides with twelve sets of 8 consecutive adenosines and mononucleotide interrupting sequences | AAAAAAAATAAAAAAAATAAAAAAAACAAAAAAAAAAAA<br>AAAGAAAAAAAATAAAAAAAACAAAAAAAACAAAAAAAAT<br>AAAAAAAAGAAAAAAACAAAAAAAATAAAAAAAA | 11 |
| PolyA-1<br>Bcl11a primer annealing sites flanking sequence comprising five interrupting sequences separating six repeats of 12 consecutive adenosines | TCTTCCTTCAGTCTGTAAACCTCAGCTCGAGAAAAAAAAA<br>AAATGGAAAAAAAAAAAACGGAAAAAAAAAAAAGGTAAAA<br>AAAAAAAATATAAAAAAAAAAAACATAAAAAAAAAAAACG<br>TTCATATCGGTTCTAGACCACACTTCTTACTGAGGTCCC | 12 |
| PolyA-2<br>Bcl11a primer annealing sites flanking sequence comprising five interrupting sequences separating six sets of 12 consecutive adenosines | TCTTCCTTCAGTCTGTAAACCTCAGAATTCATCTAGCTCG<br>AGAAAAAAATTCGAAAAAAAAAAAACGTAAAAAAAAAAAC<br>TCAAAAAAAAAAAGATAAAAAAAAAAAACCTAAAAAAAA<br>AAATGTAAAAAAAAAAAGGGAAAGTCTTCCATATCGGT<br>TCTAGACCACACTTCTTACTGAGGTCCC | 13 |
| PolyA-3<br>Bcl11a primer annealing sites flanking sequence | TCTTCCTTCAGTCTGTAAACCTCAGCTCGAGGAAGACAAG<br>GGAAAAAAAAAAACGCAAAAAAAAAAAACACAAAAAAAA<br>AAAATGCAAAAAAAAAAAATCGAAAAAAAAAAAATCTAAA | 14 |

TABLE 1-continued

| Description | Sequence | SEQ ID No |
|---|---|---|
| comprising five interrupting sequences separating six sets of 12 consecutive adenosines | AAAAAAAAACGTTCATATCGGTTCTAGACCACACTTCTTA CTGAGGTCCC | |
| PolyA-4 Blc11a primer annealing sites flanking sequence comprising six interrupting sequences separating seven sets of 12 consecutive adenosines | TCTTCCTTCAGTCTGTAAACCTCAGCTCGAGAAAAAATTC GAAAAAAAAAAAACCCAAAAAAAAAAAAGACAAAAAAAAA AAATAGAAAAAAAAAAAAAGTTAAAAAAAAAAAACTGAAAA AAAAAAAATTTAAAAAAAAAAAAATCTAGACCACACTTCTT ACTGAGGTCCC | 15 |
| PolyA 1-2 Blc11a primer annealing sites flanking sequence comprising 11 interrupting sequences separating 12 sets of 12 consecutive adenosines | TCTTCCTTCAGTCTGTAAACCTCAGAATTCATCTAGCTCG AGAAAAAAAAAAAATGGAAAAAAAAAAAACGGAAAAAAAA AAAAGGTAAAAAAAAAAAAATATAAAAAAAAAAAACATAAA AAAAAAAACGAAAAAAAAAAAACGTAAAAAAAAAAAACT CAAAAAAAAAAAGATAAAAAAAAAAAACCTAAAAAAAAA AAATGTAAAAAAAAAAAAGGGAAAGTCTTCCATATCGGTT CTAGACCACACTTCTTACTGAGGTCCC | 16 |
| PolyA 3-4 Blc11a primer annealing sites flanking sequence comprising 12 interrupting sequences separating 13 sets of 12 consecutive adenosines | TCTTCCTTCAGTCTGTAAACCTCAGCTCGAGGAAGACAAG GGAAAAAAAAAAAACGCAAAAAAAAAAAAACACAAAAAAAA AAAATGCAAAAAAAAAAAAATCGAAAAAAAAAAAATCTAAA AAAAAAAACGAAAAAAAAAAAAACCCAAAAAAAAAAAAGA CAAAAAAAAAAAATAGAAAAAAAAAAAAGTTAAAAAAAAA AAACTGAAAAAAAAAAAAATTTAAAAAAAAAAAATCTAGAC CACACTTCTTACTGAGGTCCC | 17 |
| 300PA sequence of an exemplary poly-A tail comprising 24 interrupting sequences separating 13 repeats of 12 consecutive adenosines | AAAAAAAAAAAATGGAAAAAAAAAAAACGGAAAAAAAAAA AAGGTAAAAAAAAAAAATATAAAAAAAAAAAACATAAAAA AAAAAACGAAAAAAAAAAAACGTAAAAAAAAAAAACTCA AAAAAAAAAAGATAAAAAAAAAAAACCTAAAAAAAAAA ATGTAAAAAAAAAAAAGGGAAAAAAAAAAAACGCAAAAAA AAAAACACAAAAAAAAAAAATGCAAAAAAAAAAAATCGA AAAAAAAAAAATCTAAAAAAAAAAAACGAAAAAAAAAAAA CCCAAAAAAAAAAAAGACAAAAAAAAAAAATAGAAAAAA AAAAAGTTAAAAAAAAAAAACTGAAAAAAAAAAAATTTAA AAAAAAAAA | 18 |
| 100PA - sequence of an exemplary poly-A tail comprising 97 adenine nucleotide homopolymer | AAAAAAAAAA AAAAAAAAAA AAAAAAAAAA AAAAAAAAAA AAAAAAAAAA AAAAAAAAAA AAAAAAAAAA AAAAAAAAAA AAAAAAAAAA AAAAAAA | 19 |
| pUC-M seq2 forward primer | GGGTTATTGTCTCATGAGCG | 20 |
| pUC-M seq reverse primer | TTTTGTGATGCTCGTCAGGG | 21 |
| RN-Bcl11a for | TCTTCCTTCAGTCTGTAAACCTCAG | 22 |
| RN-Bcl11a rev | GGGACCTCAGTAAGAAGTGTGG | 23 |
| Liv-Udepleted: Cas9 mRNA with a poly-A tail consisting of 98 consecutive adenosines | TCCCGCAGTCGGCGTCCAGCGGCTCTGCTTGTTCGTGTGT GTGTCGTTGCAGGCCTTATTCGGATCCGCCACCATGGACA AGAAGTACAGCATCGGACTGGACATCGGAACAAACAGCGT CGGATGGGCAGTCATCACAGACGAATACAAGGTCCCGAGC AAGAAGTTCAAGGTCCTGGGAAACACAGACAGACACAGCA TCAAGAAGAACCTGATCGGAGCACTGGTGTTCGACAGCGG AGAAACAGCAGAAGCAACAAGACTGAAGAGAACAGCAAGA AGAAGATACACAAGAAGAAAGAACAGAATCTGCTACCTGC AGGAAATCTTCAGCAACGAAATGGCAAAGGTCGACGACAG CTTCTTCGACAGACTGGAAGAAAGCTTCCTGGTCGAAGAA GACAAGAAGCACGAAAGACACCCGATCTTCGaAAACATCG TCGACGAAGTCGCATACCACGAAAAGTACCCGACAATCTA CCACCTGAGAAAGAAGCTGGTCGACAGCACAGACAAGGCA GACCTGAGACTGATCTACCTGGCACTGGCACACATGATCA AGTTCAGAGGACACTTCCTGATCGAAGGAGACCTGAACCC GGACAACAGCGACGTCGACAAGCTGTTCATCCAGGTGGTC CAGACATACAACCAGCTGTTCGAAGAAAACCCGATCAACG CAAGCGGAGTCGACGCAAAGGCAATCCTGAGCGCAAGACT GAGCAAGAGCAGAAGACTGGAAAACCTGATCGCACAGCTG CCGGGAGAAAAGAAGAACGGACTGTTCGGAAACCTGATCG CACTGAGCCTGGGACTGACACCGAACTTCAAGAGCAACTT CGACCTGGCAGAAGACGCAAAGCTGCAGCTGAGCAAGGAC ACATACGACGACGACCTGGACAACCTGCTGGCACAGATCG GAGACCAGTACGCAGACCTGTTCCTGGCAGCAAAGAACCT | 24 |

TABLE 1-continued

| Description | Sequence | SEQ ID No |
|---|---|---|
| | GAGCGACGCAATCCTGCTGAGCGACATCCTGAGAGTCAAC | |
| | ACAGAAATCACAAAGGCACCGCTGAGGGCAAGCATGATCA | |
| | AGAGATACGACGAACACCACCAGGACCTGACACTGCTGAA | |
| | GGCACTGGTCAGACAGCAGCTGCCGGAAAAGTACAAGGAA | |
| | ATCTTCTTCGACCAGAGCAAGAACGGATACGCAGGATACA | |
| | TCGACGGAGGAGCAAGCCAGGAAGAATTCTACAAGTTCAT | |
| | CAAGCCGATCCTGGAAAAGATGGACGGAACAGAAGAACTG | |
| | CTGGTCAAGCTGAACAGAGAAGACCTGCTGAGAAAGCAGA | |
| | GAACATTCGACAACGGAAGCATCCCGCACCAGATCCACCT | |
| | GGGAGAACTGCACGCAATCCTGAGAAGACAGGAAGACTTC | |
| | TACCCGTTCCTGAAGGACAACAGAGAAAAGATCGAAAAGA | |
| | TCCTGACATTCAGAATCCCGTACTACGTCGGACCGCTGGC | |
| | AAGAGGAAACAGCAGATTCGCATGGATGACAAGAAAGAGC | |
| | GAAGAAACAATCACACCGTGGAACTTCGAAGAAGTCGTCG | |
| | ACAAGGGAGCAAGCGCACAGAGCTTCATCGAAAGAATGAC | |
| | AAACTTCGACAAGAACCTGCCGAACGAAAAGGTCCTGCCG | |
| | AAGCACAGCCTGCTGTACGAATACTTCACAGTCTACAACG | |
| | AACTGACAAAGGTCAAGTACGTCACAGAAGGAATGAGAAA | |
| | GCCGGCATTCCTGAGCGGAGAACAGAAGAAGGCAATCGTC | |
| | GACCTGCTGTTCAAGACAAACAGAAAGGTCACAGTCAAGC | |
| | AGCTGAAGGAAGACTACTTCAAGAAGATCGAATGCTTCGA | |
| | CAGCGTCGAAATCAGCGGAGTCGAAGACAGATTCAACGCA | |
| | AGGCTGGGAACATACCACGACCTGCTGAAGATCATCAAGG | |
| | ACAAGGACTTCCTGGACAACGAAGAAAACGAAGACATCCT | |
| | GGAAGACATCGTCCTGACACTGACACTGTTCGAAGACAGA | |
| | GAAATGATCGAAGAAAGACTGAAGACATACGCACACCTGT | |
| | TCGACGACAAGGTCATGAAGCAGCTGAAGAGAAGAAGATA | |
| | CACAGGATGGGGAAGACTGAGCAGAAAGCTGATCAACGGA | |
| | ATCAGAGACAAGCAGAGCGGAAAGACAATCCTGGACTTCC | |
| | TGAAGAGCGACGGATTCGCAAACAGAAACTTCATGCAGCT | |
| | GATCCACGACGACAGCCTGACATTCAAGGAAGACATCCAG | |
| | AAGGCACAGGTCAGCGGACAGGGAGACAGCCTGCACGAAC | |
| | ACATCGCAAACCTGGCAGGAAGCCCGGCAATCAAGAAGGG | |
| | AATCCTGCAGACAGTCAAGGTCGTCGACGAACTGGTCAAG | |
| | GTCATGGGAAGACACAAGCCGGAAAACATCGTCATCGAAA | |
| | TGGCAAGAGAAAACCAGACAACACAGAAGGGACAGAAGAA | |
| | CAGCAGAGAAAGAATGAAGAGAATCGAAGAAGGAATCAAG | |
| | GAACTGGGAAGCCAGATCCTGAAGGAACACCCGGTCGAAA | |
| | ACACACAGCTGCAGAACGAAAAGCTGTACCTGTACTACCT | |
| | GCAGAACGGAAGAGACATGTACGTCGACCAGGAACTGGAC | |
| | ATCAACAGACTGAGCGACTACCCTGACGACCACATCGTCC | |
| | CGCAGAGCTTCCTGAAGGACGACAGCATCGACAACAAGGT | |
| | CCTGACAAGAAGCGACAAGAACAGAGGAAAGAGCGACAAC | |
| | GTCCCGAGCGAAGAAGTCCCCAAGAAGATGAAGAACTACT | |
| | GGAGACAGCTGCTGAACGCAAAGCTGATCACACAGAGAAA | |
| | GTTCGACAACCTGACAAAGGCAGAGAGAGGAGGACTGAGC | |
| | GAACTGGACAAGGCAGGATTCATCAAGAGACAGCTGGTCG | |
| | AAACAAGACAGATCACAAAGCACGTCGCACAGATCCTGGA | |
| | CAGCAGAATGAACACAAAGTACGACGAAAACGACAAGCTG | |
| | ATCAGAGAAGTCAAGGTCATCACACTGAAGAGCAAGCTGC | |
| | TCAGCGACTTCAGAAAGGACTTCCAGTTCTACAAGGTCAG | |
| | AGAAATCAACAACTACCACCACGCACACGACGCATACCTG | |
| | AACGCAGTCGTCGGAACAGCACTGATCAAGAAGTACCCGA | |
| | AGCTGGAAAGCGAATTCGTCTACGGAGACTACAAGGTCTA | |
| | CGACGTCAGAAAGATGATCGCAAAGAGCGAACAGGAAATC | |
| | GGAAAGGCAACAGCAAAGTACTTCTTCTACAGCAACATCA | |
| | TGAACTTCTTCAAGACAGAAATCACACTGGCAAACGGAGA | |
| | AATCAGAAAGAGACCGCTGATCGAAACAAACGGAGAAACA | |
| | GGAGAAATCGTCTGGGACAAGGGAAGAGACTTCGCAACAG | |
| | TCAGAAAGGTCCTGAGCATGCCGCAGGTCAACATCGTCAA | |
| | GAAGACAGAAGTCCAGACAGGAGGATTCAGCAAGGAAAGC | |
| | ATCCTGCCGAAGAGAAACAGCGACAAGCTGATCGCAAGAA | |
| | AGAAGGACTGGGACCCGAAGAAGTACGGAGGATTCGACAG | |
| | CCCGACAGTCGCATACAGCGTCCTGGTCGTCGCAAAGGTC | |
| | GAAAAGGGAAAGAGCAAGAAGCTGAAGAGCGTCAAGGAAC | |
| | TGCTGGGAATCACAATCATGGAAAGAAGCAGCTTCGAAAA | |
| | GAACCCGATCGACTTCCTGGAAGCAAAGGGATACAAGGAA | |
| | GTCAAGAAGGACCTGATCATCAAGCTGCCGAAGTACAGCC | |
| | TGTTCGAACTGGAAAACGGAAGAAAGAGAATGCTGGCAAG | |
| | CGCAGFAGAACTGCAGAAGGCAAACGAACTGGCACTGCCG | |
| | AGCAAGTACGTCAACTTCCTGTACCTGGCAAGCCACTACG | |
| | AAAAGCTGAAGGGAAGCCCGGAAGACAACGAACAGAAGCA | |
| | GCTGTTCGTCGAACAGCAaAAGCACTACCTGGACGAAATC | |
| | ATCGAACAGATCAGCGAATTCAGCAAGAGAGTCATCCTGG | |
| | CAGACGCAACCTGGACAAGGTCCTGAGCGCATAACAACAA | |
| | GCACAGAGACAAGCCGATCAGAGAACAGGCAGAAAACATC | |
| | ATCCACCTGTTCACACTGACAAACCTGGGAGCACCGCCAG | |

TABLE 1-continued

| Description | Sequence | SEQ ID No |
|---|---|---|
| | CATTCAAGTACTTCGACACAACAATCGACAGAAAGAGATA<br>CACAAGCACAAAGGAAGTCCTGGACGCAACACTGATCCAC<br>CAGAGCATCACAGGACTGTACGAAACAAGAATCGACCTGA<br>GCCAGCTGGGAGGAGACGGAGGAGGAAGCCCGAAGAAGAA<br>GAGAAAGGTCTAGCTAGCCATCACATTTAAAAGCATCTCA<br>GCCTACCATGAGAATAAGAAAAGAAAATGAAGATCAATA<br>GCTTATTCATCTCTTTTTCTTTTTCGTTGGTGTAAAGCCA<br>ACACCCTGTCTAAAAAACATAAATTTCTTTAATCATTTTG<br>CCTCTTTTCTCTGTGCTTCAATTAATAAAAAATGGAAAGA<br>ACCTCGAGAAAAAAAAAAAAAAAAAAAAAAAAAAAAAAA<br>AAAAAAAAAAAAAAAAAAAAAAAAAAAAAAAAAAAAAAA<br>AAAAAAAAAAAAAAAAAAAAAAAAA | |
| Cas9 mRNA with a poly-A tail comprising SEQ ID NO: 3 | TCCCGCAGTCGGCGTCCAGCGGCTCTGCTTGTTCGTGTGT<br>GTGTCGTTGCAGGCCTTATTCGGATCCGCCACCATGGACA<br>AGAAGTACAGCATCGGACTGGACATCGGAACAAACAGCGT<br>CGGATGGGCAGTCATCACAGACGAATACAAGGTCCCGAGC<br>AAGAAGTTCAAGGTCCTGGGAAACACAGACAGACACAGCA<br>TCAAGAAGAACCTGATCGGAGCACTGCTGTTCGACAGCGG<br>AGAAACAGCAGAAGCAACAAGACTGAAGAGAACAGCAAGA<br>AGAAGATACACAAGAAGAAAGAACAGAATCTGCTACCTGC<br>AGGAAATCTTCAGCAACGAAATGGCAAAGGTCGACGACAG<br>CTTCTTCCACAGACTGGAAGAAAGCTTCCTGGTCGAAGAA<br>GACAAGAAGCACGAAAGACACCCGATCTTCGGAAACATCG<br>TCGACGAAGTCGCATACCACGAAAAGTACCCGACAATCTA<br>CCACCTGAGAAAGAAGCTGGTCGACAGCACAGACAAGGCA<br>GACCTGAGACTGATCTACCTGGCACTGGCACACATGATCA<br>AGTTCAGAGGACACTTCCTGATCGAAGGAGACCTGAACCC<br>GGACAACAGCGACGTCGACAAGCTGTTCATCCAGCTGGTC<br>CAGACATACAACCAGCTGTTCGAAGAAAACCCGATCAACG<br>CAAGCGGAGTCGACGCAAAGGCAATCCTGAGCGCAAGACT<br>GAGCAAGAGCAGAAGACTGGAAAACCTGATCGCACAGCTG<br>CCGGGAGAAAAGAAGAACGGACTGTTCGGAAACCTGATCG<br>CACTGAGCCTGGGACTGACACCGAACTTCAAGAGCAACTT<br>CGACCTGGCAGAAGACGCAAAGCTGCAGCTGAGCAAGGAC<br>ACATACGACGACGACCTGGACAACCTGCTGGCACAGATCG<br>GAGACCAGTACGCAGACCTGTTCCTGGCAGCAAAGAACCT<br>GAGCGACGCAATCCTGCTGAGCGACATCCTGAGAGTCAAC<br>ACAGAAATCACAAAGGCACCGCTGAGCGCAAGCATGATCA<br>AGAGATACGACGAACACCACCAGGACCTGACACTGCTGAA<br>GGCACTGGTCAGACAGCAGCTGCCGGAAAAGTACAAGGAA<br>ATCTTCTTCGACCAGAGCAAGAACGGATACGCAGGATACA<br>TCGACGGAGGAGCAAGCCAGGAAGAATTCTACAAGTTCAT<br>CAAGCCGATCCTGGAAAAGATGGACGGAACAGAAGAACTG<br>CTGGTCAAGCTGAACAGAGAAGACCTGCTGAGAAAGCAGA<br>GAACATTCGACAACGGAAGCATCCCGCACCAGATCCACCT<br>GGGAGAACTGCACGCAATCCTGAGAAGACAGGAAGACTTC<br>TACCCGTTCCTGAAGGACAACAaAGAAAAGATCGAAAAGA<br>TCCTGACATTCAGAATCCCGTACTACGTCGGACCGCTGGC<br>AAGAGGAAACAGCAGATTCGCATGGATGACAAGAAAGAGC<br>GAAGAAACAATCACACCGTGGAACTTCGAAGAAGTCGTCG<br>ACAAGGGAGCAAGCGCACAGAGCTTCATCGAAAGAATGAC<br>AAACTTCGACAAGAACCTGCCGAACGAAAAGGTCCTGCCG<br>AAGCACAGCCTGCTGTACGAATACTTCACAGTCTACAACG<br>AACTGACAAAGGTCAAGTACGTCACAGAAGGAATGAGAAA<br>GCCGGCATTCCTGAGCGGAGAACAGAAGAAGGCAATCGTC<br>GACCTGCTGTTCAAGACAAACAGAAAGGTCACAGTCAAGC<br>AGCTGAAGGAAGACTACTTCAAGAAGATCGAATGCTTCGA<br>CAGCGTCGAAATCAGCGGAGTCGAAGACAGATTCAACGCA<br>AGCCTGGaAACATACCACGACCTGCTGAAGATCATCAAGG<br>ACAAGGACTTCCTGGACAACGAAGAAAACGAAGACATCCT<br>GGAAGACATCGTCCTGACACTGACACTGTTCGAAGACAGA<br>GAAATGATCGAAGAAAGACTGAAGACATACGCACACCTGT<br>TCGACGACAAGGTCATGAAGCAGCTGAAGAGAAGAAGATA<br>CACAGGATGGGAAGACTGAGCAGAAAGCTGATCAACGGA<br>ATCAGAGACAAGCAGAGCGGAAAGACAATCCTGGACTTCC<br>TGAAGAGCGACGGATTCGCAAACAGAAACTTCATGCAGCT<br>GATCCACGACGACAGCCTGACATTCAAGGAAGACATCCAG<br>AAGGCACAGGTCAGCGGACAGGGAGACAGCCTGCACGAAC<br>ACATCGCAAACCTGGCAGGAAGCCCGGCAATCAAGAAGGG<br>AATCCTGCAGACAGTCAAGGTCGTCGACGAACTGGTCAAG<br>GTCATGGGAAGACACAAGCCGGAAAACATCGTCATCGAAA<br>TGGCAAGAGAAAACCAGACAACACAGAAGGGACAGAAGAA<br>CAGCAGAGAAAGAATGAAGAGAATCGAAGAAGGAATCAAG<br>GAACTGGGAAGCCAGATCCTGAAGGAACACCCGGTCGAAA<br>ACACACAGCTGCAGAACGAAAAGCTGTACCTGTACTACCT<br>GCAGAACGGAAGAGACATGTACGTCGACCAGGAACTGGAC | 25 |

TABLE 1-continued

| Description | Sequence | SEQ ID No |
|---|---|---|
| | ATCAACAGACTGAGCGACTACGACGTCGACCACATCGTCC CGCAGAGCTTCCTGAAGGACGACAGCATCGACAACAAGGT CCTGACAAGAAGCGACAAGAACAGAGGAAAGAGCGACAAC GTCCCGAGCGAAGAAGTCGTCAAGAAGATGAAGAACTACT GGAGACAGCTGCTGAACGCAAAGCTGATCACACAGAGAAA GTTCGACAACCTGACAAAGGCAGAGAGAGGAGGACTGAGC GAACTGGACAAGGCAGGATTCATCAAGAGACAGCTGGTCG AAACAAGACAGATCACAAAGCACGTCGCACAGATCCTGGA CAGCAGAATGAACACAAAGTACGACGAAAACGACAAGCTG ATCAGAGAAGTCAAGGTCATCACACTGAAGAGCAAGCTGG TCAGCGACTTCAGAAAGGACTTCCAGTTCTACAAGGTCAG AGAAATCAACAACTACCACCACGCACACGACGCATACCTG ATCGCAGTCGTCGGAACAGCACTGATCAAGAAGTACCCGA AGCTGGAAAGCGAATTCGTCTACGGAGACTACAAGGTCTA CGACGTCAGAAAGATGATCGCAAAGAGCGAACAGGAAATC GGAAAGGCAACAGCAAAGTACTTCTTCTACAGCAACATCA TGAACTTCTTCAAGACAGAAATCACACTGGCAAACGGAGA AATCAGAAAGAGACCGCTGATCGAAACAAACGGAGAAACA GGAGAAATCGTCTGGGACAAGGGAAGAGACTTCGCAACAG TCAGAAAGGTCCTGAGCATGCCGCAGGTCAACATCGTCAA GAAGACAGAAGTCCAGACAGGAGGATTCAGCAAGGAAAGC ATCCTGCCGAAGAGAAACAGCGACAAGCTGATCGCAAGAA AGAAGGACTGGGACCCCGAAGAAGTACGGAGGATTCGACAG CCCGACAGTCGCATACAGCGTCCTGGTCGTCGCAAAGGTC GAAAAGGGAAAGAGCAAGAAGCTGAAGAGCGTCAAGGAAC TGCTGGGAATCACAATCATGGAAAGAAGCAGCTTCGAAAA GAACCCGATCGACTTCCTGGAAGCAAAGGGATACAAGGAA GTCAAGAAGGACCTGATCATCAAGCTGCCGAAGTACAGCC TGTTCGAACTGGAAAACGGAAGAAAGAGAATGCTGGCAAG CGCAGGAGAACTGCAGAAGGGAAACGAACTGGCACTGCCG AGCAAGTACGTCAACTTCCTGTACCTGGCAAGCCACTACG AAAAGCTGAAGGGAAGCCCGGAAGACAACGAACAGAAGGA GCTGTTCGTCGAACAGCACAAGCACTACCTGGACGAAATC ATCGAACAGATCAGCGAATTCAGCAAGAGAGTCATCCTGG CAGACGCAAACCTGGACAAGGTCCTGAGCGCATACAACAA GCACAGAGACAAGCCGATCAGAGAACAGGCAGAAAACATC ATCCACCTGTTCACACTGACAAACCTGGGAGCACCGGCAG CATTCAAGTACTTCGACACAACAATCGACAGAAAGAGATA CACAAGCACAAAGGAAGTCCTGGACGCAACACTGATCCAC CAGAGCATCACAGGACTGTACGAAACAAGAATCGACCTGA GCCAGCTGGGAGGAGACGGAGGAGGAAGCCCGAAGAAGAA GAGAAAGGTCTAGCTAGCCATCACATTTAAAAGCATCTCA GCCTACCATGAGAATAAGAGAAAGAAAATGAAGATCAATA GCTTATTCATCTCTTTTTCTTTTTCGTTGGTGTAAAGCCA ACACCCTGTCTAAAAAACATAAATTTCTTTAATCATTTTG CCTCTTTTCTCTGTGCTTCAATTAATAAAAAATGGAAAGA ACCAAAAAAAAAAAAAAAAAAAAAAAAAAGCGAAAAAAAA AAAAAAAAAAAAAAAACCGAAAAAAAAAAAAAAAAAAAAA AAAAGTGAAAAAAAAAAAAAAAAAAAAAAAAA | |
| Cas9 mRNA with a poly-A tail comprising SEQ ID NO: 4 | TCCCGCAGTCGGCGTCCAGCGGCTCTGCTTGTTCGTGTGT GTGTCGTTGCAGGCCTTATTCGGATCCGCCACCATGGACA AGAAGTACAGCATCGGACTGGACATCGGAACAAACAGCGT CGGATGGGCAGTCATCACAGACGAATACAAGGTCCCGAGC AAGAAGTTCAAGGTCCTGGGAAACACAGACAGACAGGA TCAAGAAGAACCTGATCGGAGCACTGCTGTTCGACAGCGG AGAAACAGCAGAAGAAGCAAGACTGAAGAGAACAGCAAGA AGAAGATACACAAGAAGAAAGAACAGAATCTGCTACCTGC AGGAAATCTTCAGCAACakAATGGCAAAGGTCGACGACAG CTTCTTCCACAGACTGGAAGAAAGCTTCCTGGTCGAAGAA GACAAGAAGCACGAAAGACACCCGATCTTCGGAAACATCG TCGACGAAGTCGCATACCACGAAAAGTACCCGACAATCTA CCACCTGAGAAAGAAGCTGGTCGACAGCACAGACAAGGCA GACCTGAGACTGATCTACCTGGCACTGGCACACATGATCA AGTTCAGAGGACACTTCCTGATCGAAGGAGACCTGAACCC GGACAACAGCGACGTCGACAAGCTGTTCATCCAGCTGGTC CAGACATACAACCAGCTGTTCGAAGAAAACCCGATCAACG CAAGCGGAGTCGACGCAAAGGCAATCCTGAGCGCAAGACT GAGCAAGAGCAGAAGACTGGAAAACCTGATCGCACAGCTG CCGCCAGAAAAGAAGAACGGACTGTTCGGAAACCTGATCG CACTGAGCCTGGGACTGACACCGAACTTCAAGAGCAACTT CGACCTGGCAGAAGACGCAAAGCTGCAGCTGAGCAAGGAC ACATACGACGACGACCTGGACAACCTGCTGGCACAGATCG GAGACCAGTACGCAGACCTGTTCCTGGCAGCAAAGAACCT GAGCGACGCAATCCTGCTGAGCGACATCCTGAGAGTCAAC ACAGAAATCACAAAGGCACCGCTGAGCGCAAGCATGATCA AGAGATACGACGAACACCACCAGGACCTGACACTGCTGAA | 26 |

TABLE 1-continued

| Description | Sequence | SEQ ID No |
|---|---|---|
| | GGCACTGGTCAGACAGCAGCTGCCGGAAAAGTACAAGGAA ATCTTCTTCGACCAGAGCAAGAACGGATACGCAGGATACA TCGACGGAGGAGCAAGCCAGGAAGAATTCTACAAGTTCAT CAAGCCGATCCTGGAAAAGATGGACGGAACAGAAGAACTG CTGGTCAAGCTGAACAGAGAAGACCTGCTGAGAAAGCAGA GAACATTCGACAACGGAAGCATCCCGCACCAGATCCACCT GGGAGAACTGCACGCAATCCTGAGAAGACAGGAAGACTTC TACCCGTTCCTGAAGGACAACAGAGAAAAGATCGAAAAGA TCCTGACATTCAGAATCCCGTACTACGTCGGACCGCTGGC AAGAGGAAACAGCAGATTCGCATGGATGACAAGAAAGAGC GAAGAAACAATCACACCGTGGAACTTCGAAGAAGTCGTCG ACAAGGGAGCAAGCGCACAGAGCTTCATCGAAAGAATGAC AAACTTCGACAAGAACCTGCCGAACGAAAAGGTCCTGCCG AAGCACAGCCTGCTGTACGAATACTTCACAGTCTACAACG AACTGACAAAGGTCAAGTACGTCACAGAAGGAATGAGAAA GCCGGCATTCCTGAGCGGAGAACAGAAGAAGGCAATCGTC GACCTGCTGTTCAAGACAAACAGAAAGGTCACAGTCAAGC AGCTGAAGGAAGACTACTTCAAGAAGATCGAATGCTTCGA CAGCGTCGAAATCAGCGGAGTCGAAGACAGATTCAACGCA AGCCTGGGAACATACCACGACCTGCTGAAGATCATCAAGG ACAAGGACTTCCTGGACAACGAAGAAAACGAAGACATCCT GGAAGACATCGTCCTGACACTGACACTGTTCGAAGACAGA GAAATGATCGAAGAAAGACTGAAGACATACGCACACCTGT TCGACGACAAGGTCATGAAGCAGCTGAAGAGAAGAAGATA CACAGGATGGGGAAGACTGAGCAGAAAGCTGATCAACGGA ATCAGAGACAAGCAGAGCGGAAAAGACAATCCTGGACTTCC TGAAGAGCGACGGATTCGCAAACAGAAACTTCATGCAGCT GATCCACGACGACAGCCTGACATTCAAGGAAGACATCCAG AAGGCACAGGTCAGCGGACAGGGAGACAGCCTGCACGAAC ACATCGCAAACCTGGCAGGAAGCCCGGCAATCAAGAAGGG AATCCTGCAGACAGTCAAGGTCGTCGACGAACTCCCCAAG GTCATGGGAAGCACAAGCCGGAAAACATCGTCATCGAAA TGGCAAGAGAAAACCAGACAACACAGAAGGGACAGAAGAA CAGCAGAGAAAGAATGAAGAGAATCGAAGAAGGAATCAAG GAACTGGGAAGCCAGATCCTGAAGGAACACCCGGTCGAAA ACACACAGCTGCAGAACGAAAAGCTGTACCTGTACTACCT GCAGAACGGAAGAGACATGTACGTCGACCAGGAACTGGAC ATCAACAGACTGAGCGACTACGACGTCGACCACATCGTCC CGCAGAGCTTCCTGAAGGACGACAGCATCGACAACAAGGT CCTGACAAGAAGCGACAAGAACAGAGGAAAGAGCGACAAC GTCCCGAGCGAAGAAGTCCCCAAGAAGATGAAGAACTACT GGAGACAGCTGCTGAACGCAAAGCTGATCACACAGAGAAA GTTCGACAACCTGACTAAGGCAGAGAGAGGAGGACTGAGC GAACTGGACAAGGCAGGATTCATCAAGAGACAGCTGGTCG AAAACAAGACAGATCACAAAGCACGTCGCACAGATCCTGGA CAGCAGAATGAACACAAAGTACGACGAAAACGACAAGCTG ATCAGAGAAGTCAAGGTCATCACACTGAAGAGCAAGCTGG TCAGCGACTTCAGAAAGGACTTCCAGTTCTACAAGGTCAG AGAAATCAACAACTACCACCACGCACACGACGCATACCTG AACGCAGTCGTCGGAACAGCACTGATCAAGAAGTACCCGA AGCTGGAAAGCGAATTCGTCTACGGAGACTACAAGGTCTA CGACGTCAGAAAGATGATCGCAAAGAGCGAACAGGAAATC GGAAAGGCAACAGCAAAGTACTTCTTCTACAGCAACATCA TGAACTTCTTCAAGACAGAAATCACACTGGCAAACGGAGA AATCAGAAAGAGACCGCTGATCGAAACAAACGGAGAAACA GGAGAAATCGTCTGGGACAAGGGAAGAGACTTCGCAACAG TCAGAAAGGTCCTCACCATGCCGCAGGTCAACATCGTCAA GAAGACAGAAGTCCAGACAGGAGGATTCAGCAAGGAAAGC ATCCTGCCGAAGAGAAACAGCGACAAGCTGATCGCAAGAA AGAAGGACTGGGACCCGAAGAAGTACGGAGGATTCGACAG CCCGACAGTCGCATACAGCGTCCTGGTCGTCGCAAAGGTC GAAAAGGGAAAGAGCAAGAAGCTGAAGAGCGTCAAGGAAC TGCTGGGAATCACAATCATGGAAAGAAGCAGCTTCGAAAA GAACCCGATCGACTTCCTGGAAGCAAAGGGATACAAGGAA GTCAAGAAGGACCTGATCATCAAGCTGCCGAAGTACAGCC TGTTCGAACTGGAAAACGGAAGAAAGAGAATGCTGGCAAG CGCAGGAGAACTGCAGAAGGGAAACGAACTGGCACTGCCG AGCAAGTACGTCAACTTCCTGTACCTGGCAAGCCACTACG AAAAGCTGAAGGGAAGCCCGGAAGACAACGAACAGAAGCA GCTGTTCGTCGAACAGCACAAGCACTACCTGGACGAAATC ATCGAACAGATCAGCGAATTCAGCAAGAGAGTCATCCTGC CAGACGCAAACCTGGACAAGGTCCTGAGCGCATACAACAA GCACAGAGACAAGCCGATCAGAGAACAGGCAGAAAACATC ATCCACCTGTTCACACTGACAAACCTGGGAGCACCGGCAG CATTCAAGTACTTCGACACAACAATCGACAGAAAGAGATA CACAAGCACAAAGGAAGTCCTGGACGCAACACTGATCCAC CAGAGCATCACAGGACTGTACGAAACAAGAATCGACCTGA | |

TABLE 1-continued

| Description | Sequence | SEQ ID No |
|---|---|---|
| | GCCAGCTGGGAGGAGACGGAGGAGGAAGCCCGAAGAAGAA GAGAAAGGTCTAGCTAGCCATCACATTTAAAAGCATCTCA GCCTACCATGAGAATAAGAGAAAGAAAATGAAGATCAATA GCTTATTCATCTCTTTTTCTTTTTCGTTGGTGTAAAGCCA ACACCCTGTCTAAAAAACATAAATTTCTTTAATCATTTTG CCTCTTTTCTCTGTGCTTCAATTAATAAAAAATGGAAAGA ACCAAAAAAAAAAAAAAAGAAAAAAAAAAAAAAAACAAA AAAAAAAAAAAATAAAAAAAAAAAAAAAAAAAAAAAAAA AAAAAACAAAAAAAAAAAAAAAA | |
| Cas9 mRNA with a poly-A tail comprising SEQ ID NO: 5 | TCCCGCAGTCGGCGTCCAGCGGCTCTGCTTGTTCGTGTGT GTGTCGTTGCAGGCCTTATTCGGATCCGCCACCATGGACA AGAAGTACAGCATCGGACTGGACATCGGAACAAACAGCGT CGGATGGGCAGTCATCACAGACGAATACAAGGTCCCGAGC AAGAAGTTCAAGGTCCTGGGAAACACAGACAGACACAGCA TCAAGAAGAACCTGATCGGAGCACTGCTGTTCGACAGCGG AGAAACAGCAGAAGCAACAAGACTGAAGAGAACAGCAAGA AGAAGATACACAAGAAGAAAGAACAGAATCTGCTACCTGC AGGAAATCTTCAGCAACGAAATGGCAAAGGTCGACGACAG CTTCTTCCACAGACTGGAAGAAAGCTTCCTGGTCGAAGAA GACAAGAAGCACGAAAGACACCCGATCTTCGGAAACATCG TCGACGAAGTCGCATACCACGAAAAGTACCCGACAATCTA CCACCTGAGAAAGAAGCTGGTCGACAGCACAGACAAGGCA GACCTGAGACTGATCTACCTGGCACTGGCACACATGATCA AGTTCAGAGGACACTTCCTGATCGAAGGAGACCTGAACCC GGACAACAGCGACGTCGACAAGCTGTTCATCCAGCTGGTC CAGACATACAACCAGCTGTTCGAAGAAAACCCGATCAACG CAAGCGGAGTCGACGCAAAGGCAATCCTGAGCGCAAGACT GAGCAAGAGCAGAAGACTGGAAAACCTGATCGCACAGCTG CCGGGAGAAAAGAAGAACGGACTGTTCGGAAACCTGATCG CACTGAGCCTGGGACTGACACCGAACTTCAAGAGCAACTT CGACCTGGCAGAAGACGCAAAGCTGCAGCTGAGCAAGGAC ACATACGACGACGACCTGGACAACCTGCTGGCACAGATCG GAGACCAGTACGCAGACCTGTTCCTGGCAGCAAAGAACCT GAGCGACGCAATCCTGCTGAGCGACATCCTGAGAGTCAAC ACAGAAATCACAAAGGCACCGCTGAGCGCAAGCATGATCA AGAGATACGACGAACACCACCAGGACCTGACACTGCTGAA GGCACTGGTCAGACAGCAGCTGCCGGAAAAGTACAAGGAA ATCTTCTTCGACCAGAGCAAGAACGGATACGCAGGATACA TCGACGGAGGAGCAAGCCAGGAAGAATTCTACAAGTTCAT CAAGCCGATCCTGGAAAAGATGGACGGAACAGAAGAACTG CTGGTCAAGCTGAACAGAGAAGACCTGCTGAGAAAGCAGA GAACATTCGACAACGGAAGCATCCCGCACCAGATCCACCT GGGAGAACTGCACGCAATCCTGAGAAGACAGGAAGACTTC TACCCGTTCCTGAAGGACAACAGAGAAAAGATCGAAAAGA TCCTGACATTCAGAATCCCGTACTACGTCGGACCGCTGGC AAGAGGAAACAGCAGATTCGCATGGATGACAAGAAAGAGC GAAGAAACAATCACACCGTGGAACTTCGAAGAAGTCGTCG ACAAGGGAGCAAGCGCACAGAGCTTCATCGAAAGAATGAC AAACTTCGACAAGAACCTGCCGAACGAAAAGGTCCTGCCG AAGCACAGCCTGCTGTACGAATACTTCACAGTCTACAACG AACTGACAAAGGTCAAGTACGTCACAGAAGGAATGAGAAA GCCGGCATTCCTGAGCGGAGAACAGAAGAAGGCAATCGTC GACCTGCTGTTCAAGACAAACAGAAAGGTCACAGTCAAGC AGCTGAAGGAAGACTACTTCAAGAAGATCGAATGCTTCGA CAGCGTCGAAATCAGCGGAGTCGAAGACAGATTCAACGCA AGCCTGGGAACATACCACGACCTGCTGAAGATCATCAAGG ACAAGGACTTCCTGGACAACGAAGAAAACGAAGACATCCT GGAAGACATCGTCCTGACACTGACACTGTTCGAAGACAGA GAAATGATCGAAGAAAGACTGAAGACATACGCACACCTGT TCGACGACAAGGTCATGAAGCAGCTGAAGAGAAGAAGATA CACAGGATGGGGAAGACTGAGCAGAAAGCTGATCAACGGA ATCAGAGACAAGCAGAGCGGAAAGACAATCCTGGACTTCC TGAAGAGCGACGGATTCGCAAACAGAAACTTCATGCAGCT GATCCACGACGACAGCCTGACATTCAAGGAAGACATCCAG AAGGCACAGGTCAGCGGACAGGGAGACAGCCTGCACGAAC ACATCGCAAACCTGGCAGGAAGCCCGGCAATCAAGAAGGG AATCCTGCAGACAGTCAAGGTCGTCGACGAACTGGTCAAG GTCATGGGAAGACACAAGCCGGAAAACATCGTCATCGAAA TGGCAAGAGAAAACCAGACAACACAGAAGGGACAGAAGAA CAGCAGAGAAAGAATGAAGAGAATCGAAGAAGGAATCAAG GAACTGGGAAGCCAGATCCTGAAGGAACACCCGGTCGAAA ACACACAGCTGCAGAACGAAAAGCTGTACCTGTACTACCT GCAGAACGGAAGAGACATGTACGTCGACCAGGAACTGGAC ATCAACAGACTGAGCGACTACGACGTCGACCACATCGTCC CGCAGAGCTTCCTGAAGGACGACAGCATCGACAACAAGGT CCTGACAAGAAGCGACAAGAACAGAGGGAAAGAGCGACAAC | 27 |

TABLE 1-continued

| Description | Sequence | SEQ ID No |
|---|---|---|
| | GTCCCGAGCGAAGAAGTCGTCAAGAAGATGAAGAACTACT<br>GGAGACAGCTGCTGAACGCAAAGCTGATCACACAGAGAAA<br>GTTCGACAACCTGACAAAGGCAGAGAGAGGAGGACTGAGC<br>GAACTGGACAAGGCAGGATTCATCAAGAGACAGCTGGTCG<br>AAACAAGACAGATCACAAAGCACGTCGCACAGATCCTGGA<br>CAGCAGAATGAACACAAAGTACGACGAAAACGACAAGCTG<br>ATCAGAGAAGTCAAGGTCATCACACTGAAGAGCAAGCTGG<br>TCAGCGACTTCAGAAAGGACTTCCAGTTCTACAAGGTCAG<br>AGAAATCAACAACTACCACCACGCACACGACGCATACCTG<br>AACGCAGTCGTCGGAACAGCACTGATCAAGAAGTACCCGA<br>AGCTGGAAAGCGAATTCGTCTACGGAGACTACAAGGTCTA<br>CGACGTCAGAAAGATGATCGCAAAGAGCGAACAGGAAATC<br>GGAAAGGCAACAGCAAAGTACTTCTTCTACAGCAACATCA<br>TGAACTTCTTCAAGACAGAAATCACACTGGCAAACGGAGA<br>AATCAGAAAGAGACCGCTGATCGAAACAAACGGAGAAACA<br>GGAGAAATCGTCTGGGACAAGGGAAGAGACTTCGCAACAG<br>TCAGAAAGGTCCTGAGCATGCCGCAGGTCAACATCGTCAA<br>GAAGACAGAAGTCCAGACAGGAGGATTCAGCAAGGAAAGC<br>ATCCTGCCGAAGAGAAACAGCGACAAGCTGATCGCAAGAA<br>AGAAGGACTGGGACCCGAAGAAGTACGGAGGATTCGACAG<br>CCCGACAGTCGCATACAGCGTCCTGGTCGTCGCAAAGGTC<br>GAAAAGGGAAAGAGCAAGAAGCTGAAGAGCGTCAAGGAAC<br>TGCTGGGAATCACAATCATGGAAAGAAGCAGCTTCGAAAA<br>GAACCCGATCGACTTCCTGGAAGCAAAGGGATACAAGGAA<br>GTCAAGAAGGACCTGATCATCAAGCTGCCGAAGTACAGCC<br>TGTTCGAACTGGAAAACGGAAGAAAGAGAATGCTGGCAAG<br>CGCAGGAGAACTGCAGAAGGGAAACGAACTGGCACTGCCG<br>AGCAAGTACGTCAACTTCCTGTACCTGGCAAGCCACTACG<br>AAAAGCTGAAGGGAAGCCCGGAAGACAACGAACAGAAGCA<br>GCTGTTCGTCGAACAGCACAAGCACTACCTGGACGAAATC<br>ATCGAACAGATCAGCGAATTCAGCAAGAGAGTCATCCTGG<br>CAGACGCAAACCTGGACAAGGTCCTGAGCGCATACAACAA<br>GCACAGAGACAAGCCGATCAGAGAACAGGCAGAAAACATC<br>ATCCACCTGTTCACACTGACAAACCTGGGAGCACCGGCAG<br>CATTCAAGTACTTCGACACAACAATCGACAGAAAGAGATA<br>CACAAGCACAAAGGAAGTCCTGGACGCAACACTGATCCAC<br>CAGAGCATCACAGGACTGTACGAAACAAGAATCGACCTGA<br>GCCAGCTGGGAGGAGACGGAGGAGGAAGCCCGAAGAAGAA<br>GAGAAAGGTCTAGCTAGCCATCACATTTAAAAGCATCTCA<br>GCCTACCATGAGAATAAGAGAAAGAAAATGAAGATCAATA<br>GCTTATTCATCTCTTTTTCTTTTTCGTTGGTGTAAAGCCA<br>ACACCCTGTCTAAAAAACATAAATTTCTTTAATCATTTTG<br>CCTCTTTTCTCTGTGCTTCAATTAATAAAAAATGGAAAGA<br>ACCAAAAAAAAAAAAAAAAGAAAAAAAAAAAAAAAACAAA<br>AAAAAAAAAAAATAAAAAAAAAAAAAAATAAAAAAAAAA<br>AAAAAAAAAAAAAAAAAAAAAACAAAAAAAAAAAAAAAA<br>AAAAAAAAAAAAAAAAAAAAAAAAAAAAAAAAAAAAAAA<br>AAAAAAAA | |
| Cas9 mRNA with a poly-A tail comprising SEQ ID NO: 10 | TCCCGCAGTCGGCGTCCAGCGGCTCTGCTTGTTCGTGTGT<br>GTGTCGTTGCAGGCCTTATTCGGATCCGCCACCATGGACA<br>AGAAGTACAGCATCGGACTGGACATCGGAACAAACAGCGT<br>CGGATGGGCAGTCATCACAGACGAATACAAGGTCCCGAGC<br>AAGAAGTTCAAGGTCCTGGGAAACACAGACAGACACAGCA<br>TCAAGAAGAACCTGATCGGAGCACTGCTGTTCGACAGCGG<br>AGAAACAGCAGAAGCAACAAGACTGAAGAGAACAGCAAGA<br>AGAAGATACACAAGAAGAAAGAACAGAATCTGCTACCTGC<br>AGGAAATCTTCAGCAACGAAATGGCAAAGGTCGACGACAG<br>CTTCTTCCACAGACTGGAAGAAAGCTTCCTGGTCGAAGAA<br>GACAAGAAGCACGAAAGACACCCGATCTTCGGAAACATCG<br>TCGACGAAGTCGCATACCACGAAAAGTACCCGACAATCTA<br>CCACCTGAGAATGAAGCTGGTCGACAGCACAGACATGGCA<br>GACCTGAGACTGATCTACCTGGCACTGGCACACATGATCA<br>AGTTCAGAGGACACTTCCTGATCGAAGGAGACCTGAACCC<br>GGACAACAGCGACGTCGACAAGCTGTTCATCCAGCTGGTC<br>CAGACATACAACCAGCTGTTCGAAGAAAACCCGATCAACG<br>CAAGCGGAGTCGACGCAAAGGCAATCCTGAGCGCAAGACT<br>GAGCAAGAGCAGAAGACTGGAAAACCTGATCGCACAGCTG<br>CCGGGAGAAAAGAAGAACGGACTGTTCGGAAACCTGATCG<br>CACTGAGCCTGGGACTGACACCGAACTTCAAGAGCAACTT<br>CGACCTGGCAGAAGACGCAAAGCTGCAGCTGAGCAAGGAC<br>ACATACGACGACCTGGACAACCTGCTGGCACAGATCG<br>GAGACCAGTACGCAGACCTGTTCCTGGCAGCAAAGAACCT<br>GAGCGACGCAATCCTGCTGAGCGACATCCTGAGAGTCAAC<br>ACAGAAATCACAAAGGCACCGCTGAGCGCAAGCATGATCA<br>AGAGATACGACGAACACCACCAGGACCTGACACTGCTGAA<br>GGCACTGGTCAGACAGCAGCTGCCGGAAAAGTACAAGGAA | 28 |

TABLE 1-continued

| Description | Sequence | SEQ ID No |
|---|---|---|
| | ATCTTCTTCGACCAGAGCAAGAACGGATACGCAGGATACA | |
| | TCGACGGAGGAGCAAGCCAGGAAGAATTCTACAAGTTCAT | |
| | CAAGCCGATCCTGGAAAAGATGGACGGAACAGAAGAACTG | |
| | CTGGTCAAGCTGAACAGAGAAGACCTGCTGAGAAAGCAGA | |
| | GAACATTCGACAACGGAAGCATCCCGCACCAGATCCACCT | |
| | GGGAGAACTGCACGCAATCCTGAGAAGACAGGAAGACTTC | |
| | TACCCGTTCCTGAAGGACAACAGAGAAAAGATCGAAAAGA | |
| | TCCTGACATTCAGAATCCCGTACTACGTCGGACCGCTGGC | |
| | AAGAGGAAACAGCAGATTCGCATGGATGACAAGAAAGAGC | |
| | GAAGAAACAATCACACCGTGGAACTTCGAAGAAGTCGTCG | |
| | ACAAGGGAGCAAGCGCACAGAGCTTCATCGAAAGAATGAC | |
| | AAACTTCGACAAGAACCTGCCGAACGAAAAGGTCCTGCCG | |
| | AAGCACAGCCTGCTGTACGAATACTTCACAGTCTACAACG | |
| | AACTGACAAAGGTCAAGTACGTCACAGAAGGAATGAGAAA | |
| | GCCGGCATTCCTGAGCGGAGAACAGAAGAAGGCAATCGTC | |
| | GACCTGCTGTTCAAGACAAACAGAAAGGTCACAGTCAAGC | |
| | AGCTGAAGGAAGACTACTTCAAGAAGATCGAATGCTTCGA | |
| | CAGCGTCGAAATCAGCGGAGTCGAAGACAGATTCAACGCA | |
| | AGCCTGGGAACATACCACGACCTGCTGAAGATCATCAAGG | |
| | ACAAGGACTTCCTGGACAACGAAGAAAACGAAGACATCCT | |
| | GGAAGACATCGTCCTGACACTGACACTGTTCGAAGACAGA | |
| | GAAATGATCGAAGAAAGACTGAAGACATACGCACACCTGT | |
| | TCGACGACAAGGTCATGAAGCAGCTGAAGAGAAGAAGATA | |
| | CACAGGATGGGGAAGACTGAGCAGAAAGCTGATCAACGGA | |
| | ATCAGAGACAAGCAGAGCGGAAAGACAATCCTGGACTTCC | |
| | TGAAGAGCGACGGATTCGCAAACAGAAACTTCATGCAGCT | |
| | GATCCACGACGACAGCCTGACATTCAAGGAAGACATCCAG | |
| | AAGGCACAGGTCAGCGGACAGGGAGACAGCCTGCACGAAC | |
| | ACATCGCAAACCTGGCAGGAAGCCCGGCAATCAAGAAGGG | |
| | AATCCTGCAGACAGTCAAGGTCGTCGACGAACTGGTCAAG | |
| | GTCATGGGAAGACACAAGCCGGAAAACATCGTCATCGAAA | |
| | TGGCAAGAGAAAACCAGACAACACAGAAGGGACAGAAGAA | |
| | CAGCAGAGAAAGAATGAAGAGAATCGAAGAAGGAATCAAG | |
| | GAACTGGGAAGCCAGATCCTGAAGGAACACCCGGTCGAAA | |
| | ACACACAGCTGCAGAACGAAAAGCTGTACCTGTACTACCT | |
| | GCAGAACGGAAGAGACATGTACGTCGACCAGGAACTGGAC | |
| | ATCAACGACTGAGCGACTACGACGTCGACCACATCGTCC | |
| | CGCAGAGCTTCCTGAAGGACGACAGCATCGACAACAAGGT | |
| | CCTGACAAGAAGCGACAAGAACAGAGGAAAGAGCGACAAC | |
| | GTCCCGAGCGAACAAGTCGTCAAGAAGATGAAGAACTACT | |
| | GGAGACAGCTGCTGAACGCAAAGCTGATCACACAGAGAAA | |
| | GTTCGACAACCTGACAAAGGCAGAGAGAGGAGGACTGAGC | |
| | GAACTGGACAAGGCAGGATTCATCAAGAGACAGCTGGTCG | |
| | AAACAAGACAGATCACAAAGCACGTCGCACAGATCCTGGA | |
| | CAGCAGAATGAACACAAAGTACGACGAAAACGACAAGCTG | |
| | ATCAGAGAAGTCAAGGTCATCACACTGAAGAGCAAGCTGG | |
| | TCAGCGACTTCAGAAAGGACTTCCAGTTCTACAAGGTCAG | |
| | AGAAATCAACAACTACCACCACGCACACGACGCATACCTG | |
| | AACGCAGTCGTCGGAACAGCACTGATCAAGAAGTACCCGA | |
| | AGCTGGAAAGCGAATTCGTCTACGGAGACTACAAGGTCTA | |
| | CGACGTCAGAAAGATGATCGCAAAGAGCGAACAGGAAATC | |
| | GGAAAGGCAACAGCAAAGTACTTCTTCTACAGCAACATCA | |
| | TGAACTTCTTCAAGACAGAAATCACACTGGCAAACGGAGA | |
| | AATCAGAAAGAGACCGCTGATCGAAACAAACGGAGAAACA | |
| | GGAGAAATCGTCTGGGACAAGGGAAGAGACTTCGCAACAG | |
| | TCAGAAAGGTCCTGAGCATGCCGCAGGTCAACATCGTCAA | |
| | GAAGACAGAAGTCCAGACAGGAGGATTCAGCAAGGAAAGC | |
| | ATCCTGCCGAAGAGAAACAGCGACAAGCTGATCGCAAGAA | |
| | AGAAGGACTGGGACCCGAAGAAGTACGGAGGATTCGACAG | |
| | CCCGACAGTCGCATACAGCGTCCTGGTCGTCGCAAAGGTC | |
| | GAAAAGGGAAAGAGCAAGAAGCTGAAGAGCGTCAAGGAAC | |
| | TGCTGGGAATCACAATCATGGAAAGAAGCAGCTTCGAAAA | |
| | GAACCCGATCGACTTCCTGGAAGCAAAGGGATACAAGGAA | |
| | GTCAAGAAGGACCTGATCATCAAGCTGCCGAAGTACAGCC | |
| | TGTTCGAACTGGAAAACGGAAGAAAGAGAATGCTGGCAAG | |
| | CGCAGGAGAACTGCAGAAGGGAAACGAACTGGCACTGCCG | |
| | AGCAAGTACGTCAACTTCCTGTACCTGGCAAGCCACTACG | |
| | AAAAGCTGAAGGGAAGCCCGGAAGACAACGAACAGAAGCA | |
| | GCTGTTCGTCGAACAGCACAAGCACTACCTGGACGAAATC | |
| | ATCGAACAGATCAGCGAATTCAGCAAGAGAGTCATCCTGG | |
| | CAGACGCAAACCTGGACAAGGTCCTGAGCGCATACAACAA | |
| | GCACAGAGACAAGCCGATCAGAGAACAGGCAGAAAACATC | |
| | ATCCACCTGTTCACACTGACAAACCTGGGAGCACCGGCAG | |
| | CATTCAAGTACTTCGACACAACAATCGACAGAAAGAGATA | |
| | CACAAGCACAAAGGAAGTCCTGGACGCAACACTGATCCAC | |
| | CAGAGCATCACAGGACTGTACGAAACAAGAATCGACCTGA | |
| | GCCAGCTGGGAGGAGACGGAGGAGGAAGCCCGAAGAAGAA | |

TABLE 1-continued

| Description | Sequence | SEQ ID No |
|---|---|---|
|  | GAGAAAGGTCTAGCTAGCCATCACATTTAAAAGCATCTCA GCCTACCATGAGAATAAGAGAAAGAAAATGAAGATCAATA GCTTATTCATCTCTTTTTCTTTTTCGTTGGTGTAAAGCCA ACACCCTGTCTAAAAAACATAAATTTCTTTAATCATTTTG CCTCTTTTCTCTGTGCTTCAATTAATAAAAAATGGAAAGA ACCAAAAAAAAAAAATAAAAAAAAAAAATAAAAAAAAAA ACAAAAAAAAAAAATAAAAAAAAAAAACAAAAAAAAAAA GAAAAAAAAAAAACAAAAAAAAAAAATAAAAAAAAAAA |  |
| Cas 9 mRNA with a poly-A tail comprising SEQ ID NO: 11 | TCCCGCAGTCGGCGTCCAGCGGCTCTGCTTGTTCGTGTGT GTGTCGTTGCAGGCCTTATTCGGATCCGCCACCATGGACA AGAAGTACAGCATCGGACTGGACATCGGAACAAACAGCGT CGGATGGGCAGTCATCACAGACGAATACAAGGTCCCGAGC AAGAAGTTCAAGGTCCTGGGAAACACAGACAGACACAGCA TCAAGAAGAACCTGATCGGAGCACTGCTGTTCGACAGCGG AGAAACAGCAGAAGCAACAAGACTGAAGAGAACAGCAAGA AGAAGATACAAGAAGAAAGAACAGAATCTGCTACCTGC AGGAAATCTTCAGCAACGAAATGGCAAAGGTCGACGACAG CTTCTTCCACAGACTGGAAGAAAGCTTCCTGGTCGAAGAA GACAAGAAGCACGAAAGACACCCGATCTTCGGAAACATCG TCGACGAAGTCGCATACCACGAAAAGTACCCGACAATCTA CCACCTGAGAAAGAAGCTGGTCGACAGCACAGACAAGGCA GACCTGAGACTGATCTACCTGGCACTGGCACACATGATCA AGTTCAGAGGACACTTCCTGATCGAAGGAGACCTGAACCC GGACAACAGCGACGTCGACAAGCTGTTCATCCAGCTGGTC CAGACATACAACCAGCTGTTCGAAGAAAACCCGATCAACG CAAGCGGAGTCGACGCAAAGGCAATCCTGAGCGCAAGACT GAGCAAGAGCAGAAGACTGGAAAACCTGATCGCACAGCTG CCGGGAGAAAAGAAGAACGGACTGTTCGGAAACCTGATCG CACTGAGCCTGGGACTGACACCGAACTTCAAGAGCAACTT CGACCTGGCAGAAGACGCAAAGCTGCAGCTGAGCAAGGAC ACATACGACGACGACCTGGACAACCTGCTGGCACACATCG GAGACCAGTACGCAGACCTGGTCCTGGCAGCAAAGAACCT GAGCGACGCAATCCTGCTGAGCGACATCCTGAGAGTCAAC ACAGAAATCACAAAGGCACCGCTGAGCGCAAGCATGATCA AGAGATACGACGAACACCACCAGGACCTGACACTGCTGAA GGCACTGGTCAGACAGCAGCTGCCGGAAAAGTACAAGGAA ATCTTCTTCGACCAGAGCAAGAACGGATACGCAGGATACA TCGACGGAGGAGCAAGCCAGGAAGAATTCTACAAGTTCAT CAAGCCGATCCTGGAAAAGATGGACGGAACAGAAGAACTG CTGGTCAAGCTGAACAGAGAAGACCTGCTGAGAAAGCAGA GAACATTCGACAACGGAAGCATCCCGCACCAGATCCACCT GGGAGAACTGCACGCAATCCTGAGAAGACAGGAAGACTTC TACCCGTTCCTGAAGGACAACAGAGAAAAGATCGAAAAGA TCCTGACATTCAGAATCCCGTACTACGTCGGACCGCTGGC AAGAGGAAACAGCAGATTCGCATGGATGACAAGAAAGAGC GAAGAAACAATCACACCGTGGAACTTCGAAGAAGTCGTCG ACAAGGGAGCAAGCGCACAGAGCTTCATCGAAAGAATGAC AAACTTCGACAAGAACCTGCCGAACGAAAAGGTCCTGCCG AAGCACAGCCTGCTGTACGAATACTTCACAGTCTACAACG AACTGACAAAGGTCAAGTACGTCACAGAAGGAATGAGAAA GCCGGCATTCCTGAGCGGAGAACAGAAGAAGGCAATCGTC GACCTGCTGTTCAAGACAAACAGAAAGGTCACAGTCAAGC AGCTGAAGGAAGACTACTTCAAGAAGATCGAATGCTTCGA CAGCGTCGAAATCAGCGGAGTCGAAGACAGATTCAACGCA AGCCTGGGAACATACCACGACCTGCTGAAGATCATCAAGG ACAAGGACTTCCTGGACAACGAAGAAAACGAAGACATCCT GGAAGACATCGTCCTGACACTGACACTGTTCGAAGACAGA GAAATGATCGAAGAAAGACTGAAGACATACGCACACCTGT TCGACGACAAGGTCATGAAGCAGCTGAAGAGAAGAAGATA CACAGGATGGGGAAGACTGAGCAGAAAGCTGATCAACGGA ATCAGAGACAAGCAGAGCGGAAAGACAATCCTGGACTTCC TGAAGAGGGACGGATTCGCAAACAGAAACTTCATGCAGCT GATCCACGACGACAGCCTGACATTCAAGGAAGACATCCAG AAGGCACAGGTCAGCGGACAGGGAGACAGCCTGCACGAAC ACATCGCAAACCTGGCAGGAAGCCCGGCAATCAAGAAGGG AATCCTGCAGACAGTCAAGGTCGTCGACGAACTGGTCAAG GTCATGGGAAGACACAAGCCGGAAAACATCGTCATCGAAA TGGCAAGAGAAAACCAGACAACACAGAAGGGACAGAAGAA CAGCAGAGAAAGAATGAAGAGAATCGAAGAAGGAATCAAG GAACTGGGAAGCCAGATCCTGAAGGAACACCCGGTCGAAA ACACACAGCTGCAGAACGAAAAGGTGTACCTGTACTACCT GCAGAACGGAAGAGACATGTACGTCGACCAGGAACTGGAC ATCAACAGACTGAGGGACTACGACGTCGACCACATCGTCC CGCAGAGCTTCCTGAAGGACGACAGCATCGACAACAAGGT CCTGACAAGAAGCGACAAGAACAGAGGAAAGAGCGAaAAC GTCCCGAGCGAAGAAGTCGTCAAGAAGATGAAGAAGTACT | 29 |

TABLE 1-continued

| Description | Sequence | SEQ ID No |
|---|---|---|
| | GGAGACAGCTGGTGAACGCAAAGCTGATCACACAGAGAAA<br>GTTCGACAACCTGACAAAGGCAGAGAGAGGAGGACTGAGC<br>GAACTGGACAAGGCAGGATTCATCAAGAGACAGCTGGTCG<br>AAACAAGACAGATCACAAAGCACGTCGCACAGATCCTGGA<br>CAGCAGAATGAACACAAAGTACGACGAAAACGACAAGCTG<br>ATCAGAGAAGTCAAGGTCATCACACTGAAGAGCAAGCTGG<br>TCAGCGACTTCAGAAAGGACTTCCAGTTCTACAAGGTCAG<br>AGAAATCAACAACTACCACCACGCACACGACGCATACCTG<br>AACGCAGTCGTCGGAACAGCACTGATCAAGAAGTACCCGA<br>AGCTGGAAAGCGAATTCGTCTACGGAGACTACAAGGTCTA<br>CGACGTCAGAAAGATGATCGCAAAGAGGGAACAGGAAATC<br>GGAAAGGCAACAGCAAAGTACTTCTTCTACAGCAACATCA<br>TGAACTTCTTCAAGACAGAAATCACACTGGCAAACGGAGA<br>AATCAGAAAGAGACCGCTGATCGAAACAAACGGAGAAACA<br>GGAGAAATCGTCTGGGACAAGGGAAGAGACTTCGCAACAG<br>TCAGAAAGGTCCTGAGCATGCCGGAGGTCAACATCGTCAA<br>GAAGACAGAAGTCCAGACAGGAGGATTCAGGAAGGAAAGG<br>ATCCTGCCGAAGAGAAACAGCGACAAGCTGATCGCAAGAA<br>AGAAGGACTGGGACCCCGAAGAAGTACGGAGGATTCGACAG<br>CCCGACAGTCGGATACAGCGTCCTGGTCGTCGCAAAGGTC<br>GAAAAGGGAAAGAGCPAGAAGCTGAAGAGCGTCAAGGAAC<br>TGGTGGGAATCACAATCATGGAAAGAAGCAGCTTCGAAAA<br>GAACCCGATCGACTTCCTGGAAGCAAAGGGATACAAGGAA<br>GTCAAGAAGGACCTGATCATCAAGCTGCCGAAGTACAGCC<br>TGTTCGAACTGGAAAACGGAAGAAAGAGAATGCTGGCAAG<br>CGCAGGAGAACTGCAGAAGGGAAACGAACTGGCACTGCCG<br>AGCAAGTACGTCAACTTCCTGTACCTGGCAAGCCACTACG<br>AAAAGCTGAAGGGAAGCCCGGAAGACAACGAACAGAAGCA<br>GCTGTTCGTCGAACAGCACAAGCACTACCTGGACGAAATC<br>ATCGAACAGATCAGCGAATTCAGCAAGAGAGTCATCCTGG<br>CAGACGCAAACCTGGACAAGGTCCTGAGCGCATACAACAA<br>GCACAGAGACAAGCCGATCAGAGAACAGGCAGAAAACATC<br>ATCCACCTGTTCACACTGACAAACCTGGGAGCACCGGCAG<br>CATTCAAGTACTTCGACACAACAATCGACAGAAAGAGATA<br>CACAAGCACAAAGGAAGTCCTGGACGCAACACTGATCCAC<br>CAGAGCATCACAGGACTGTACGAAACAAGAATCGACCTGA<br>GCCAGCTGGGAGGAGACGGAGGAGGAAGCCCGAAGAAGAA<br>GAGAAAGGTCTAGCTAGCCATCACATTTAAAAGCATCTCA<br>GCCTACCATGAGAATAAGAGAAAGAAAATGAAGATCAATA<br>GCTTATTCATCTCTTTTTCTTTTTCGTTGGTGTAAAGCCA<br>ACACCCTGTCTAAAAAACATAAATTTCTTTAATCATTTTG<br>CCTCTTTTCTCTGTGCTTCAATTAATAAAAAATGGAAAGA<br>ACCAAAAAAATAAAAAAATAAAAAAACAAAAAAAAAA<br>AAAAAAAAAAAAAATAAAAAAAACAAAAAAAACAAAAAA<br>AATAAAAAAAAGAAAAAAAACAAAAAAAATAAAAAAAA | |
| Cas 9 mRNA with a poly-A tail comprising SEQ ID NO: 19 | TCCCGCAGTCGGCGTCCAGCGGCTCTGCTTGTTCGTGTGT<br>GTGTCGTTGCAGGCCTTATTCGGATCCGCCACCATGGACA<br>AGAAGTACAGCATCGGACTGGACATCGGAACAAACAGCGT<br>CGGATGGGCAGTCATCACAGACGAATACAAGGTCCCGAGC<br>AAGAAGTTCAAGGTCCTGGGAAACACAGACAGACACAGCA<br>TCAAGAAGAACCTGATCGGAGCACTGCTGTTCGACAGCGG<br>AGAAACAGCAGAAGCAACAAGACTGAAGAGAACAGCAAGA<br>AGAAGATACACAAGAAGAAAGAACAGAATCTGCTACCTGC<br>AGGAAATCTTCAGCAACGAAATGGCAAAGGTCGACGACAG<br>CTTCTTCCACAGACTGGAAGAAAGCTTCCTGGTCGAAGAA<br>GACAAGAAGCACGAAAGACACCCGATCTTCGGAAACATCG<br>TCGACGAAGTCGCATACCACGAAAAGTACCCGACAATCTA<br>CCACCTGAGAAAGAAGCTGGTCGACAGCACAGACAAGGCA<br>GACCTGAGACTGATCTACCTGGCACTGGCACACATGATCA<br>AGTTCAGAGGACACTTCCTGATCGAAGGAGACCTGAACCC<br>GGACAACAGCGACGTCGACAAGCTGTTCATCCAGCTGGTC<br>CAGACATACAACCAGCTGTTCGAAGAAAACCCGATCAACG<br>CAAGCGGAGTCGACGCAAAGGCAATCCTGAGCGCAAGACT<br>GAGCAAGAGCAGAAGACTGGAAAACCTGATCGCACAGCTG<br>CCGGGAGAAAAGAAGAACGGACTGTTCGGAAACCTGATCG<br>CACTGAGCCTGGGACTGACACCGAACTTCAAGAGCAACTT<br>CGACCTGGCAGAAGACGCAAAGCTGCAGCTGAGCAAGGAC<br>ACATACGACGACGACCTGGACAACCTGCTGGCACAGATCG<br>GAGACCAGTACGCAGACCTGTTCCTGGCAGCAAAGAACCT<br>GAGCGACGCAATCCTGCTGAGCGACATCCTGAGAGTCAAC<br>ACAGAAATCACAAAGGCACCGCTGAGCGCAAGCATGATCA<br>AGAGATACGACGAACACCACCAGGACCTGACACTGCTGAA<br>GGCACTGGTCAGACAGCAGCTGCCGGAAAAGTACAAGGAA<br>ATCTTCTTCGACCAGAGCAAGAACGGATACGCAGGATACA<br>TCGACGGAGGAGCAAGCCAGGAAGAATTCTACAAGTTCAT<br>CAAGCCGATCCTGGAAAAGATGGACGGAACAGAAGAACTG | 30 |

TABLE 1-continued

| Description | Sequence | SEQ ID No |
|---|---|---|
| | CTGGTCAAGCTGAACAGAGAAGACCTGCTGAGAAAGCAGA GAACATTCGACAACGGAAGCATCCCGCACCAGATCCACCT GGGAGAACTGCACGCAATCCTGAGAAGACAGGAAGACTTC TACCCGTTCCTGAAGGACAACAGAGAAAAGATCGAAAAGA TCCTGACATTCAGAATCCCGTACTACGTCGGACCGCTGGC AAGAGGAAACAGCAGATTCGCATGGATGACAAGAAAGAGC GAAGAAACAATCACACCGTGGAACTTCGAAGAAGTCGTCG ACAAGGGAGCAAGCGCACAGAGCTTCATCGAAAGAATGAC AAACTTCGACAAGAACCTGCCGAACGAAAAGGTCCTGCCG AAGCACAGCCTGCTGTACGAATACTTCACAGTCTACAACG AACTGACAAAGGTCAAGTACGTCACAGAAGGAATGAGAAA GCCGGCATTCCTGAGCGGAGAACAGAAGAAGGCAATCGTC GACCTGCTGTTCAAGACAAACAGAAAGGTCACAGTCAAGC AGCTGAAGGAAGACTACTTCAAGAAGATCGAATGCTTCGA CAGCGTCGAAATCAGCGGAGTCGAAGACAGATTCAACGCA AGCCTGGAACATACCACGACCTGCTGAAGATCATCAAGG ACAAGGACTTCCTGGACAACGAAGAAAACGAAGACATCCT GGAAGACATCGTCCTGACACTGACACTGTTCGAAGACAGA GAAATGATCGAAGAAGACTGAAGACATACGCACACCTGT TCGACGACAAGGTCATGAAGCAGCTGAAGAGAAGAAGATA CACAGGATGGGGAAGACTGAGCAGAAAGCTGATCAACGGA ATCAGAGACAAGCAGAGCGGAAAAGACAATCCTGGACTTCC TGAAGAGCGACGGATTCGCAAACAGAAACTTCATGCAGCT GATCCACGACGACAGCCTGACATTCAAGGAAGACATCCAG AAGGCACAGGTCAGCGGACAGGGAGACAGCCTGCACGAAC ACATCGCAAACCTGGCAGGAAGCCCGGCAATCAAGAAGGG AATCCTGCAGACAGTCAAGGTCGTCGACGAACTGGTCAAG GTCATGGGAAGACACAAGCCGGAAAACATCGTCATCGAAA TGGCAAGAGAAAACCAGACAACACAGAAGGGACAGAAGAA CAGCAGAGAAAGAATGAAGAGAATCGAAGAAGGAATCAAG GAACTGGGAAGCCAGATCCTGAAGGAACACCCGGTCGAAA ACACACAGCTGCAGAACGAAAAGCTGTACCTGTACTACCT GCAGAACGGAAGAGACATGTACGTCGACCAGGAACTGGAC ATCAACAGACTGAGCGACTACGACGTCGACCACATCGTCC CGCAGAGCTTCCTGAAGGACGACAGCATCGACAACAAGGT CCTGACAAGAAGCGACAAGAACAGAGGAAAGAGCGACAAC GTCCCGAGCGAAGAAGTCGTCAAGAAGATGAAGAACTACT GGAGACAGCTGCTGAACGCAAAGCTGATCACACAGAGAAA GTTCGACAACCTGACAAAGGCAGAGAGAGGAGGACTGAGC GAACTGGACAAGGCAGGATTCATCAAGAGACAGCTGGTCG AAACAAGACAGATCACAAAGCACGTCGCACAGATCCTGGA CAGCAGAATGAACACAAAGTACGACGAAAACGACAAGCTG ATCAGAGAAGTCAAGGTCATCACACTGAAGAGCAAGCTGG TCAGCGACTTCAGAAAGGACTTCCAGTTCTACAAGGTCAG AGAAATCAACAACTACCACCACGCACACGACGCATACCTG AACGCAGTCGTCGGAACAGCACTGATCAAGAAGTACCCGA AGCTGGAAAGCGAATTCGTCTACGGAGACTACAAGGTCTA CGACGTCAGAAAGATGATCGCAAAGAGCGAACAGGAAATC GGAAAGGCAACAGCAAAGTACTTCTTCTACAGCAACATCA TGAACTTCTTCAAGACAGAAATCACACTGGCAAACGGAGA AATCAGAAAGAGACCGCTGATCGAAACAAACGGAGAAACA GGAGAAATCGTCTGGGACAAGGGAAGAGACTTCGCAACAG TCAGAAAGGTCCTGAGCATGCCGCAGGTCAACATCGTCAA GAAGACAGAAGTCCAGACAGGAGGATTCAGCAAGGAAAGC ATCCTGCCGAAGAGAAACAGCGACAAGCTGATCGCAAGAA AGAAGGACTGGGACCCGAAGAAGTACGGAGGATTCGACAG CCCGACAGTCGCATACAGCGTCCTGGTCGTCGCAAAGGTC GAAAAGGGAAAGAGCAAGAAGCTGAAGAGCGTCAAGGAAC TGCTGGGAATCACAATCATGGAAAGAAGCAGCTTCGAAAA GAACCCGATCGACTTCCTGGAAGCAAAGGGATACAAGGAA GTCAAGAAGGACCTGATCATCAAGCTGCCGAAGTACAGCC TGTTCGAACTGGAAAACGGAAGAAAGAGAATGCTGGCAAG CGCAGGAGAACTGCAGAAGGGAAACGAACTGGCACTGCCG AGCAAGTACGTCAACTTCCTGTACCTGGCCACTACG AAAAGCTGAAGGGAAGCCCGGAAGACAACGAACAGAAGCA GCTGTTCGTCGAACAGCACAAGCACTACCTGGACGAAATC ATCGAACAGATCAGCGAATTCAGCAAGAGAGTCATCCTGG CAGACGCAAACCTGGACAAGGTCCTGAGCGCATACAACAA GCACAGAGACAAGCCGATCAGAGAACAGGCAGAAAACATC ATCCACCTGTTCACACTGACAAAACCTGGGAGCACCGGCAG CATTCAAGTACTTCGACACAACAATCGACAGAAAGAGATA CACAAGCACAAAGGAAGTCCTGGACGCAACACTGATCCAC CAGAGCATCACAGGACTGTACGAAACAAGAATCGACCTGA GCCAGCTGGGAGGAGACGGAGGAGGAAGCCCGAAGAAGAA GAGAAAGGTCTAGCTAGCCATCACATTTAAAAGCATCTCA GCCTACCATGAGAATAAGAGAAAGAAAATGAAGATCAATA GCTTATTCATCTCTTTTTCTTTTTCGTTGGTGTAAAGCCA | |

TABLE 1-continued

| Description | Sequence | SEQ ID No |
|---|---|---|
| | ACACCCTGTCTAAAAAACATAAATTTCTTTAATCATTTTG CCTCTTTTCTCTGTGCTTCAATTAATAAAAAATGGAAAGA ACCAAAAAAAAAAAAAAAAAAAAAAAAAAAAAAAAAAA AAAAAAAAAAAAAAAAAAAAAAAAAAAAAAAAAAAAAA AAAAAAAAAAAAAAAAAAA | |
| Cas 9 mRNA with a poly-A tail comprising SEQ ID NO: 2 | TCCCGCAGTCGGCGTCCAGCGGCTCTGCTTGTTCGTGTGT GTGTCGTTGCAGGCCTTATTCGGATCCGCCACCATGGACA AGAAGTACAGCATCGGACTGGACATCGGAACAAACAGCGT CGGATGGGCAGTCATCACAGACGAATACAAGGTCCCGAGC AAGAAGTTCAAGGTCCTGGGAAACACAGACAGACACAGCA TCAAGAAGAACCTGATCGGAGCACTGCTGTTCGACAGCGG AGAAACAGCAGAAGCAACAAGACTGAAGAGAACAGCAAGA AGAAGATACACAAGAAGAAAGAACAGAATCTGCTACCTGC AGGAAATCTTCAGCAACGAAATGGCAAAGGTCGACGACAG CTTCTTCCACAGACTGGAAGAAAGCTTCCTGGTCGAAGAA GACAAGAAGCACGAAAGACACCCGATCTTCGGAAACATCG TCGACGAAGTCGCATACCACGAAAAGTACCCGACAATCTA CCACCTGAGAAAGAAGCTGGTCGACAGCACAGACAAGGCA GACCTGAGACTGATCTACCTGGCACTGGCACACATGATCA AGTTCAGAGGACACTTCCTGATCGAAGGAGACCTGAACCC GGACAACAGCGACGTCGACAAGCTGTTCATCCAGCTGGTC CAGACATACAACCAGCTGTTCGAAGAAAACCCGATCAACG CAAGCGGAGTCGACGCAAAGGCAATCCTGAGCGCAAGACT GAGCAAGAGCAGAAGACTGGAAAACCTGATCGCACAGCTG CCGGGAGAAAAGAAGAACGGACTGTTCGGAAACCTGATCG CACTGAGCCTGGGACTGACACCGAACTTCAAGAGCAACTT CGACCTGGCAGAAGACGCAAAGCTGCAGCTGAGCAAGGAC ACATACGACGACGACCTGGACAACCTGCTGGCACAGATCG GAGACCAGTACGCAGACCTGTTCCTGGCAGCAAAGAACCT GAGCGACGCAATCCTGCTGAGCGACATCCTGAGAGTCAAC ACAGAAATCACAAAGGCACCGCTGAGCGCAAGCATGATCA AGAGATACGACGAACACCACCAGGACCTGACACTGCTGAA GGCACTGGTCAGACAGCAGCTGCCGGAAAAGTACAAGGAA ATCTTCTTCGACCAGAGCAAGAACGGATACGCAGGATACA TCGACGGAGGAGCAAGCCAGGAAGAATTCTACAAGTTCAT CAAGCCGATCCTGGAAAAGATGGACGGAACAGAAGAACTG CTGGTCAAGCTGAACAGAGAAGACCTGCTGAGAAAGCAGA GAACATTCGACAACGGAAGCATCCCGCACCAGATCCACCT GGGAGAACTGCACGCAATCCTGAGAAGACAGGAAGACTTC TACCCGTTCCTGAAGGACAACAGAGAAAAGATCGAAAAGA TCCTGACATTCAGAATCCCGTACTACGTCGGACCGCTGGC AAGAGGAAACAGCAGATTCGCATGGATGACAAGAAAGAGC GAAGAAACAATCACACCGTGGAACTTCGAAGAAGTCGTCG ACAAGGGAGCAAGCGCACAGAGCTTCATCGAAAGAATGAC AAACTTCGACAAGAACCTGCCGAACGAAAAGGTCCTGCCG AAGCACAGCCTGCTGTACGAATACTTCACAGTCTACAACG AACTGACAAAGGTCAAGTACGTCACAGAAGGAATGAGAAA GCCGGCATTCCTGAGCGGAGAACAGAAGAAGGCAATCGTC GACCTGCTGTTCAAGACAAACAGAAAGGTCACAGTCAAGC AGCTGAAGGAAGACTACTTCAAGAAGATCGAATGCTTCGA CAGCGTCGAAATCAGCGGAGTCGAAGACAGATTCAACGCA AGCCTGGGAACATACCACGACCTGCTGAAGATCATCAAGG ACAAGGACTTCCTGGACAACGAAGAAAACGAAGACATCCT GGAAGACATCGTCCTGACACTGACACTGTTCGAAGACAGA GAAATGATCGAAGAAAGACTGAAGACATACGCACACCTGT TCGACGACAAGGTCATGAAGCAGCTGAAGAGAAGAAGATA CACAGGATGGGGAAGACTGAGCAGAAAGCTGATCAACGGA ATCAGAGACAAGCAGAGCGGAAAAGACAATCCTGGACTTCC TGAAGAGCGACGGATTCGCAAACAGAAACTTCATGCAGCT GATCCACGACGACAGCCTGACATTCAAGGAAGACATCCAG AAGGCACAGGTCAGCGGACAGGGAGACAGCCTGCACGAAC ACATCGCAAACCTGGCAGGAAGCCCGGCAATCAAGAAGGG AATCCTGCAGACAGTCAAGGTCGTCGACGAACTGGTCAAG GTCATGGGAAGACACAAGCCGGAAAACATCGTCATCGAAA TGGCAAGAGAAAACCAGACAACACAGAGGGACAGAAGAA CAGCAGAGAAAGAATGAAGAGAATCGAAGAAGGAATCAAG GAACTGGGAAGCCAGATCCTGAAGGAACACCCGGTCGAAA ACACACAGCTGCAGAACGAAAAGCTGTACCTGTACTACCT GCAGAACGGAAGAGACATGTACGTCGACCAGGAACTGGAC ATCAACAGACTGAGCGACTACGACGTCGACCACATCGTCC CGCAGAGCTTCCTGAAGGACGACAGCATCGACAACAAGGT CCTGACAAGAAGCGACAAGAACAGAGGAAAGAGCGACAAC GTCCCGAGCGAAGAAGTCGTCAAGAAGATGAAGAACTACT GGAGACAGCTGCTGAACGCAAAGCTGATCACACAGAGAAA GTTCGACAACCTGACAAAGGCAGAGAGAGGAGGACTGAGC GAACTGGACAAGGCAGGATTCATCAAGAGACAGCTGGTCG | 31 |

TABLE 1-continued

| Description | Sequence | SEQ ID No |
|---|---|---|
| | AAACAAGACAGATCACAAAGCACGTCGCACAGATCCTGGA<br>CAGCAGAATGAACACAAAGTACGACGAAAACGACAAGCTG<br>ATCAGAGAAGTCAAGGTCATCACACTGAAGAGCAAGCTGG<br>TCAGCGACTTCAGAAAGGACTTCCAGTTCTACAAGGTCAG<br>AGAAATCAACAACTACCACCACGCACACGACGCATACCTG<br>AACGCAGTCGTCGGAACAGCACTGATCAAGAAGTACCCGA<br>AGCTGGAAAGCGAATTCGTCTACGGAGACTACAAGGTCTA<br>CGACGTCAGAAAGATGATCGCAAAGAGCGAACAGGAAATC<br>GGAAAGGCAACAGCAAAGTACTTCTTCTACAGCAACATCA<br>TGAACTTCTTCAAGACAGAAATCACACTGGCAAACGGAGA<br>AATCAGAAAGAGACCGCTGATCGAAACAAACGGAGAAACA<br>GGAGAAATCGTCTGGGACAAGGGAAGAGACTTCGCAACAG<br>TCAGAAAGGTCCTGAGCATGCCGCAGGTCAACATCGTCAA<br>GAAGACAGAAGTCCAGACAGGAGGATTCAGCAAGGAAAGC<br>ATCCTGCCGAAGAGAAACAGCGACAAGCTGATCGCAAGAA<br>AGAAGGACTGGGACCCGAAGAAGTACGGAGGATTCGACAG<br>CCCGACAGTCGCATACAGCGTCCTGGTCGTCGCAAAGGTC<br>GAAAAGGGAAAGAGCAAGAAGCTGAAGAGCGTCAAGGAAC<br>TGCTGGGAATCACAATCATGGAAAGAAGCAGCTTCGAAAA<br>GAACCCGATCGACTTCCTGGAAGCAAAGGGATACAAGGAA<br>GTCAAGAAGGACCTGATCATCAAGCTGCCGAAGTACAGCC<br>TGTTCGAACTGGAAAACGGAAGAAAGAGAATGCTGGCAAG<br>CGCAGGAGAACTGCAGAAGGGAAACGAACTGGCACTGCCG<br>AGCAAGTACGTCAACTTCCTGTACCTGGCAAGCCACTACG<br>AAAAGCTGAAGGGAAGCCCGGAAGACAACGAACAGAAGCA<br>GCTGTTCGTCGAACAGCACAAGCACTACCTGGACGAAATC<br>ATCGAACAGATCAGCGAATTCAGCAAGAGAGTCATCCTGG<br>CAGACGCAAACCTGGACAAGGTCCTGAGCGCATACAACAA<br>GCACAGAGACAAGCCGATCAGAGAACAGGCAGAAAACATC<br>ATCCACCTGTTCACACTGACAAACCTGGGAGCACCGGCAG<br>CATTCAAGTACTTCGACACAACAATCGACAGAAAGAGATA<br>CACAAGCACAAAGGAAGTCCTGGACGCAACACTGATCCAC<br>CAGAGCATCACAGGACTGTACGAAACAAGAATCGACCTGA<br>GCCAGCTGGGAGGAGACGGAGGAGGAAGCCCGAAGAAGAA<br>GAGAAAGGTCTAGCTAGCCATCACATTTAAAAGCATCTCA<br>GCCTACCATGAGAATAAGAGAAAGAAAATGAAGATCAATA<br>GCTTATTCATCTCTTTTTCTTTTTCGTTGGTGTAAAGCCA<br>ACACCCTGTCTAAAAAACATAAATTTCTTTAATCATTTTG<br>CCTCTTTTCTCTGTGCTTCAATTAATAAAAAATGGAAAGA<br>ACCAAAAAAAAAAAAAAAAAAAAAAAAAAAAAAAAAAAAA<br>AAAAAAAAAAAAAAAAAAAAAAAAAAAAAAAAAAAAAAAA<br>AAAAAAAAAAAAAAAAAAAA | |

Phosphorothioate (PS) linkage or bond refers to a bond where a sulfur is substituted for one nonbridging phosphate oxygen in a phosphodiester linkage, for example in the bonds between nucleotides bases. When phosphorothioates are used to generate oligonucleotides, the modified oligonucleotides may also be referred to as S-oligos.

A "*" may be used to depict a PS modification. In this application, the terms A*, C*, U*, or G* may be used to denote a nucleotide that is linked to the next (e.g., 3') nucleotide with a PS bond.

In this application, the terms "mA*," "mC*," "mU*," or "mG*" may be used to denote a nucleotide that has been substituted with 2'-O-Me and that is linked to the next (e.g., 3') nucleotide with a PS bond.

EXAMPLES

The following examples are provided to illustrate certain disclosed embodiments and are not to be construed as limiting the scope of this disclosure in any way.

Example 1—Design and Stability of Stable Plasmids for Poly-A Coding

Poly-A tails were designed that comprised non-adenine nucleotides. The stability of plasmids encoding these poly-A tails with consecutive adenine nucleotides and non-adenine nucleotides (e.g., interrupting sequences) were compared to poly-A tails composed solely of adenine nucleotides.

The issue of loss of the number of adenosines in an mRNA poly-A tail consisting of only adenosines is highlighted in Table 2. A sequence containing a poly-A tail of 96 adenosines was inserted into a pUC57 plasmid (Genscript) and transformed into E. coli. Cells were plated on LB-Amp plates, and incubated overnight at either 30° C. or 37° C. Eight colonies were picked and inoculated into 96-well plates with LB-Amp media and grown overnight at 30° C. or 37° C. (Day 1). Samples from the Day 1 cultures were added to fresh LB-Amp media and grown for two additional days at 30° C. or 37° C. (Day 2). DNA was purified from Day 1 and Day 2 cultures and sequenced to determine poly-A tail length in the plasmids. Exemplary results are shown in Table 2 below and in FIG. 1.

TABLE 2

Poly-A length after plasmid growth in E. Coli

| | 37° C. | | | 30° C. | |
|---|---|---|---|---|---|
| Initial colony size | Day 1 poly-A length | Day 2 poly-A length | | Initial colony size | Day 1 poly-A length |
| Sm | 95 | 18 | | Reg | 80 |
| Reg | 95 | 68 | | Sm | 95 |

TABLE 2-continued

Poly-A length after plasmid growth in E. Coli

| 37° C. | | | 30° C. | |
|---|---|---|---|---|
| Initial colony size | Day 1 poly-A length | Day 2 poly-A length | Initial colony size | Day 1 poly-A length |
| Reg | 95 | 94 | Reg | 39 |
| Sm | 95 | N/A | Reg | 48 |
| Reg | 96 | N/A | Sm | 95 |
| Sm | 36-95 mix | 18 | Sm | 95 |
| Sm | 62 | 61 | Reg | 47 |
| Reg | 69 | 68 | Sm | 95 |

For a number of the colonies each round of growth was associated with a decrease in the number of adenosines within the poly-A tail, with only one colony maintaining over 90 adenosines through two rounds of replication. In addition, the size of bacterial colonies correlated with loss of poly-A tail length from the plasmid (i.e., larger colonies corresponded with loss of poly-A length), suggesting that sequences encoding longer poly-A tails may inhibit bacterial growth during plasmid production. DNA purified from colonies of E. coli represent a population of DNAs from individual E. coli harboring plasmid DNA. Thus, the values provided in Table 2 (and similar values described herein) represent average poly-A length of the population. Further, during PCR and sequencing of long repeats such as poly-A, the polymerase may slip, resulting in the appearance that the sequence is slightly shorter than the actual sequence. Thus, for results showing 95 adenosines, it is not certain whether the plasmid has lost one adenosine, or whether it is a PCR artifact. However, significant loss is not an artifact of polymerase slippage during PCR amplification and sequencing.

Figure 2:
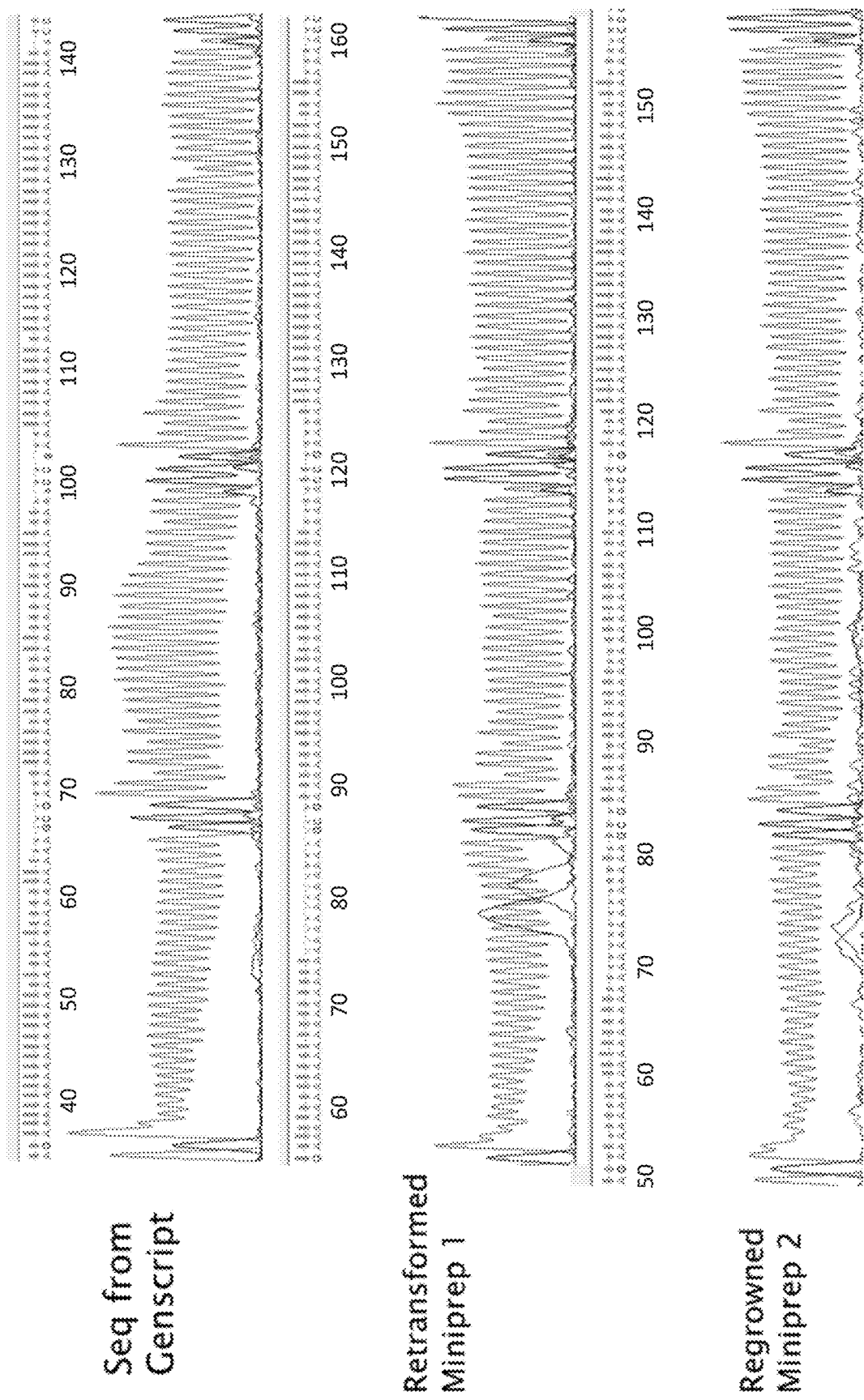
FIG. 2 shows retention of size of a poly-A tail comprising non-adenine nucleotides over 2 growth passages.

In a separate experiment, E. coli were transformed with a pUC57 plasmid containing a poly-A tail of SEQ ID NO: 1 and plated on LB-Amp plates. Eight clones were cultured through two rounds of growth and tested for maintenance of the sequence encoding the poly-A tail. Representative data on one clone is shown in FIG. 2, where no change in size of the tail was seen with the poly-A tail of SEQ ID NO: 1 over 2 rounds of growth of a plasmid encoding it. Miniprep 1 refers to the first round of growth, while Miniprep 2 refers to the second round of growth. Minipreps were performed using an Invitrogen Purelink Quick Plasmid Miniprep kit.

A plasmid encoding a poly-A tail with an additional non-adenosine pattern (SEQ ID NO: 3) was tested for its ability to withstand replication in E. coli. A sequence containing a poly-A tail of SEQ ID NO: 3 was inserted into a pUC19 plasmid (Genscript) and transformed into E. coli. Cells were plated on LB-Kan plates, and incubated overnight at either 30° C. or 37° C. Eight colonies were picked and inoculated into 96-well plates with LB-Kan media, and grown overnight at 30° C. or 37° C. (Day 1). Samples from the Day 1 cultures were added to fresh LB-Kan media and grown for two additional days at 30° C. or 37° C. (Day 2). DNA was purified from Day 1 and Day 2 cultures and sequenced to determine poly-A tail length in the plasmids. Of eight Day 1 cultures sequenced, six maintained stretches of 25, 24, 24, and 24 adenosines, and of twelve Day 2 cultures sequenced, nine maintained stretches of 25, 24, 24, and 24 adenosines, demonstrating an improvement of poly-A retention compared to adenosine-only sequences.

These data indicate that DNAs encoding poly-A tails comprising non-adenine nucleotides have improved stability over multiple rounds of plasmid growth and purification in comparison to DNAs encoding poly-A tails containing only adenosines.

Example 2—Activity of Constructs with Poly-A Tails Comprising Non-Adenine Nucleotides Experiments were performed to determine whether there was a difference in efficacy of mRNA with poly-A tails comprising non-adenine nucleotides (interrupting sequences) versus those with poly-A tails containing only adenosines. A model system was used where mRNA encoding Cas9 protein was transfected by electroporation into HEK-293 cells with a reporter plasmid encoding secreted embryonic alkaline phosphatase (SEAP), as well as a guide RNA targeting SEAP. Successful expression of Cas9 protein from the mRNA results in cleavage of the SEAP target sequence, leading to a color change reflecting decreased production of SEAP. The SEAP HEK-Blue reporter reagents were obtained from Invivogen. A sequence containing a T7 promoter and encoding a Cas9 mRNA with adenosine-only poly-A tail (designed to have 100 adenosine nucleotides, but shown as having 97 adenosine nucleotides by sequencing) (SEQ ID NO: 6) or a sequence containing a T7 promoter and encoding a Cas9 mRNA with a poly-A tail of SEQ ID NO: 1 (SEQ ID NO: 7) were cloned into pUC57 plasmid (Genscript). mRNA was produced by in vitro transcription from the linearized plasmids encoding each mRNA.

Figure 3:
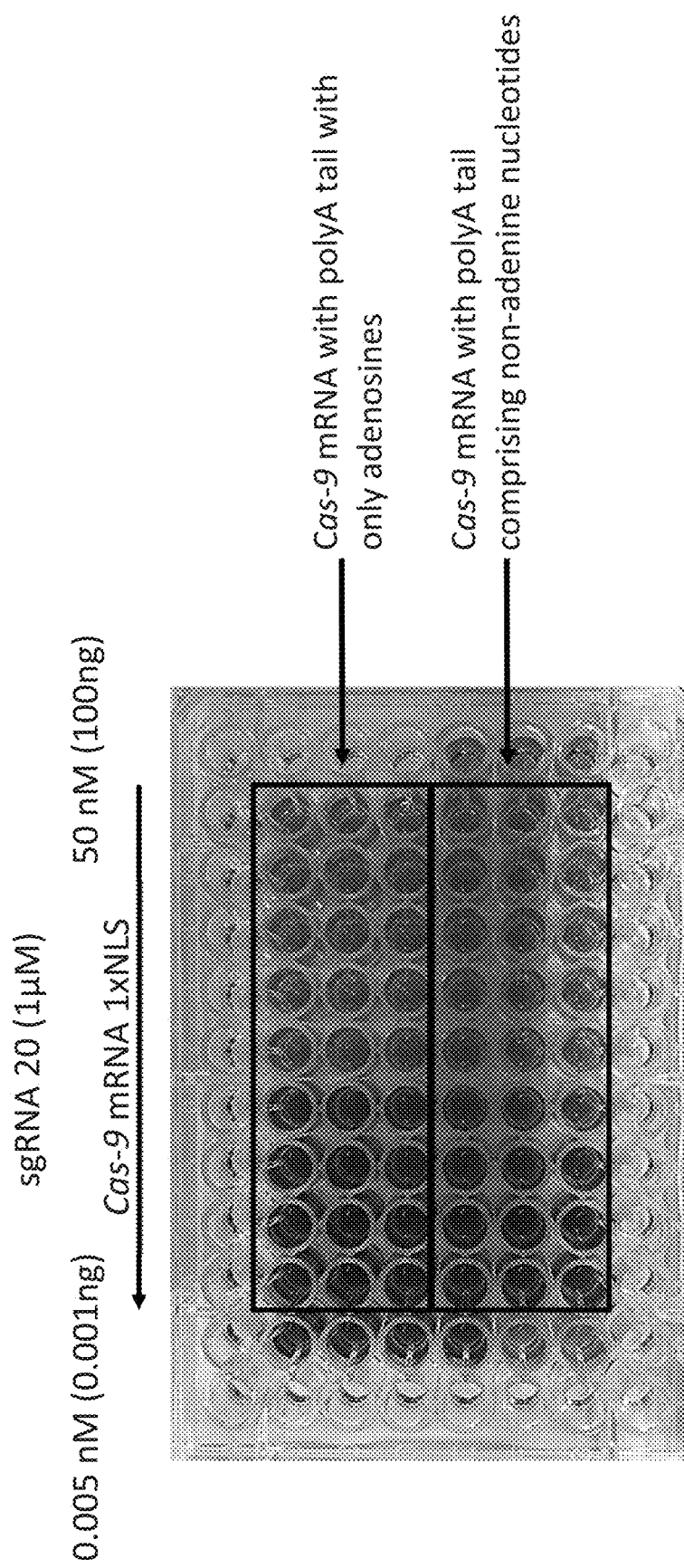
FIG. 3 shows secreted embryonic alkaline phosphatase (SEAP) levels measured in a Cas9 mRNA assay using Cas9 mRNA with a poly-A tail containing only adenosines or Cas9 mRNA with a poly-A tail comprising non-adenine nucleotides and single guide RNA targeting SEAP (SEQ ID NO: 8).

FIG. 3 shows titration of Cas9 mRNA with adenosine-only poly-A or the poly-A of SEQ ID NO: 1 in the HEK-Blue cell assay at concentrations from 0.005-50 nM, and 1 µM single guide RNA targeting SEAP (SEQ ID NO: 8).

The HEK-Blue results show that the effect of mRNA with either poly-A tail was similar across the dose-response curve. Higher concentrations of mRNA led to a decrease in SEAP reporter gene expression as evidenced by the color change to pink, as the baseline blue color indicates SEAP expression. Thus, the poly-A tail comprising non-adenine nucleotides did not change the efficacy of expression and function of a Cas9 construct compared to a poly-A tail containing only adenosines.

The efficacy of editing conferred by expression of a Cas 9 mRNA of SEQ ID NO: 6 was also compared to the Cas9 mRNA of SEQ ID NO: 7 (i.e., adenosine-only poly-A tail compared to poly-A tail of SEQ ID NO: 1). For these experiments, HEK-Blue cells were transfected with sgRNA (SEQ ID NO: 8) and the two different mRNAs by electroporation.

Figure 4:
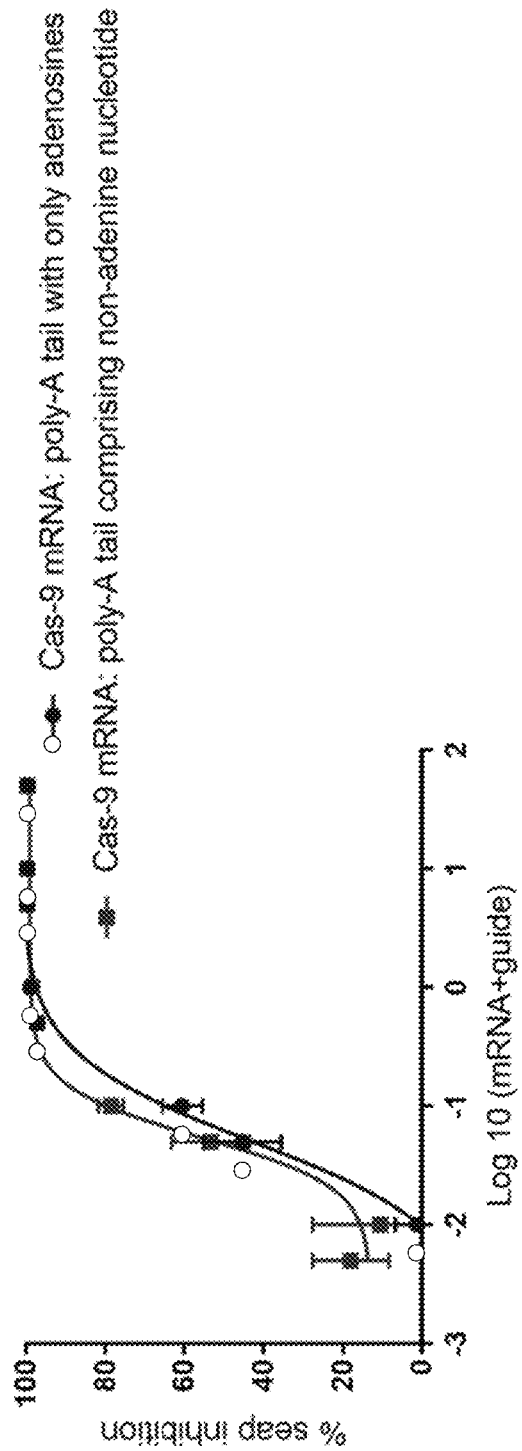
FIG. 4 shows percent SEAP inhibition measured in a Cas9 mRNA assay using Cas9 mRNA with a poly-A tail containing only adenosines or Cas9 mRNA with a poly-A tail comprising non-adenine nucleotides and single guide RNA targeting SEAP (SEQ ID NO: 8) with a 24-hour incubation.

FIG. 4 shows percent SEAP inhibition for both constructs after 24-hour incubation. The $EC_{50}$ for SEAP editing for mRNA with a poly-A tailing containing only adenosine and a poly-A tail comprising non-adenine nucleotides were similar at 0.050 and 0.054, respectively.

Figure 5:
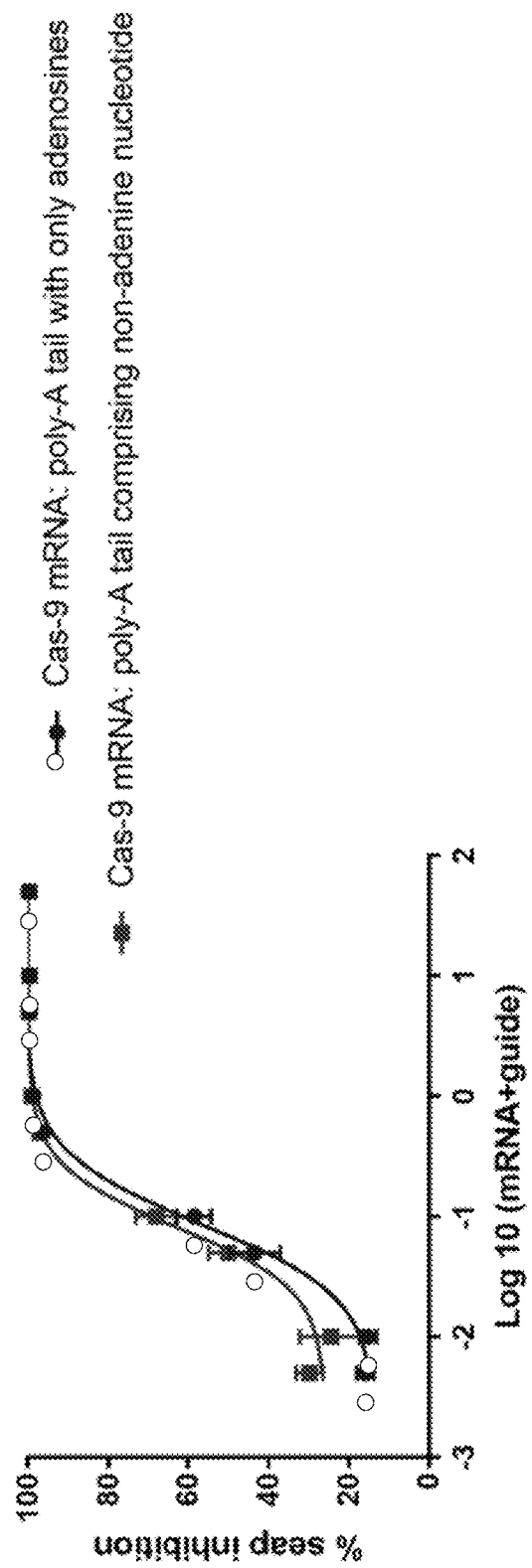
FIG. 5 shows percent SEAP inhibition measured in a Cas9 mRNA assay using Cas9 mRNA with a poly-A tail containing only adenosines or Cas9 mRNA with a poly-A tail comprising non-adenine nucleotides and single guide RNA targeting SEAP (SEQ ID NO: 8) with a 48-hour incubation.

FIG. 5 shows percent SEAP inhibition for both constructs after a 48-hour incubation. The $EC_{50}$ for SEAP editing for mRNA with a poly-A tailing containing only adenosine and a poly-A tail comprising non-adenine nucleotides were similar at 0.086 and 0.082, respectively.

mRNA expression and activity were also confirmed in vivo. The Cas9 mRNAs of SEQ ID NO: 6 (HiCas9 mRNA) and SEQ ID NO: 7 (Disrupted PolyA mRNA) were formulated with single guide RNA of SEQ ID NO: 9 (targeting mouse TTR gene) at a 1:1 weight ratio into lipid nanoparticles (LNPs) and administered to CD-1 female mice (n=5) by intravenous dosing at 1 or 0.5 mg/kg of total RNA. Blood was collected from the animals at 7 days post-dose, and serum levels of TTR protein were measured by ELISA. In short, total TTR serum levels were determined using a Mouse Prealbumin (Transthyretin) ELISA Kit (Aviva Systems Biology, Cat. OKIA00111). Kit reagents and standards were prepared according to the manufacture's protocol. The plate was read on a SpectraMax M5 plate reader at an absorbance of 450 nm. Serum TTR levels were calculated by SoftMax Pro software ver. 6.4.2 using a four parameter logistic curve fit off the standard curve. Final serum values were adjusted for the assay dilution.

Figure 6:
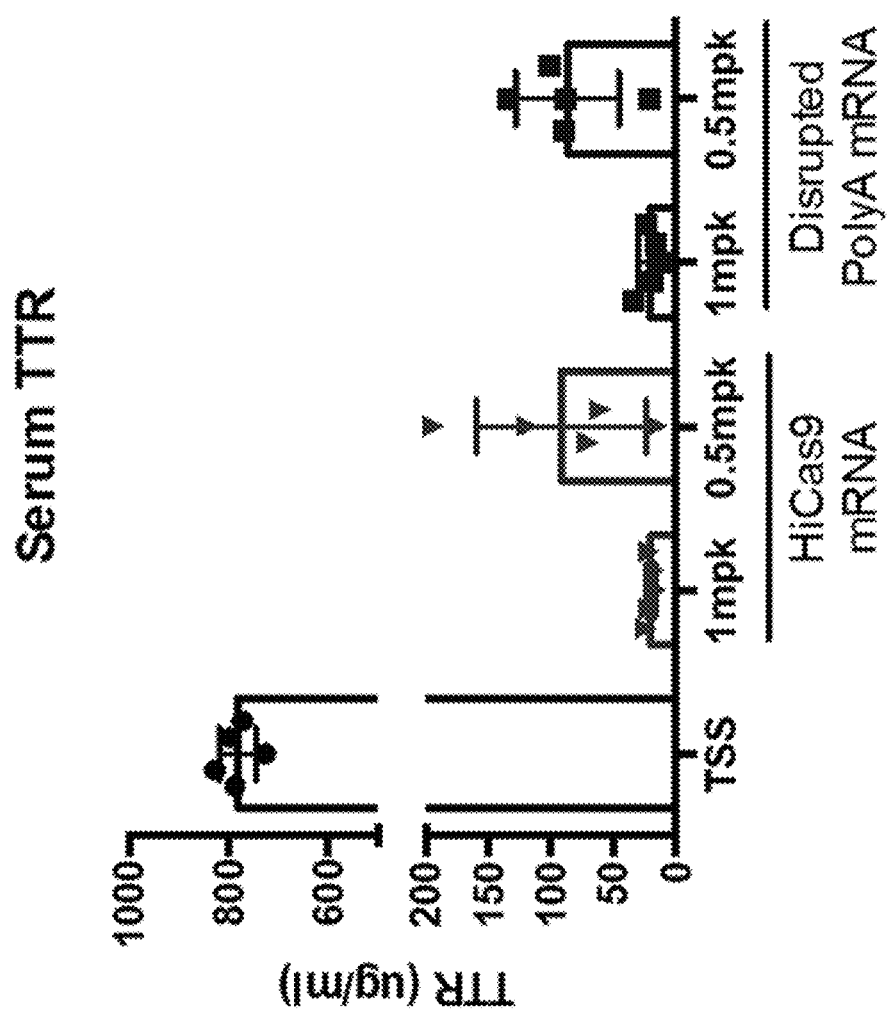
FIG. 6 shows serum transthyretin (TTR) levels in mice 7 days after dosing of a control transformation and storage solution (TSS) buffer or dosing of liquid nanoparticles (LNP) formulated with the single guide RNA of SEQ ID NO: 9 (targeting the mouse TTR gene) and either an mRNA encoded by SEQ ID NO: 6 (HiCas9 mRNA) or by SEQ ID NO: 7 (disrupted Poly-A mRNA).

FIG. 6 shows comparable levels of serum TTR knockdown (representative of percentage editing of the TTR gene) for both poly-A constructs at 7 days post-dose. Serum TTR knockdown results were confirmed by sequencing of the TTR locus in livers of the mice harvested at 7 days. Mice receiving the adenosine-only poly-A mRNA showed 61.74% and 69.84% editing at 0.5 and 1 mg/kg total RNA, respectively, while mice receiving the poly-A mRNA containing non-adenosine nucleotides showed 63.14% and 70.82% editing at 0.5 and 1 mg/kg total RNA.

Therefore, expression of a Cas9 mRNA with a poly-A tail comprising non-adenine nucleotides produced similar editing efficacy compared to a Cas9 mRNA with a poly-A tail containing only adenosines.

Example 3—Activity of Constructs with Poly-A Tails Comprising Additional Interrupting Sequences Experiments were performed to determine efficacy of mRNA with poly-A tails comprising non-adenine nucleotides versus those with poly-A tails containing only adenosine nucleotides as in Example 2. Sequences containing a T7 promoter and encoding a Cas9 mRNA with an interrupted poly-A tail comprising SEQ ID NO: 2, SEQ ID NO: 3, SEQ ID NO: 4, SEQ ID NO: 5, SEQ ID NO: 10, or SEQ ID NO: 11 were made by PCR amplification using primers to incorporate the poly-A sequences. mRNA was produced by in vitro transcription from these PCR products. mRNA for SEQ ID NO: 18 was produced by in vitro transcription from a linearized plasmid encoding the mRNA.

Figure 7:
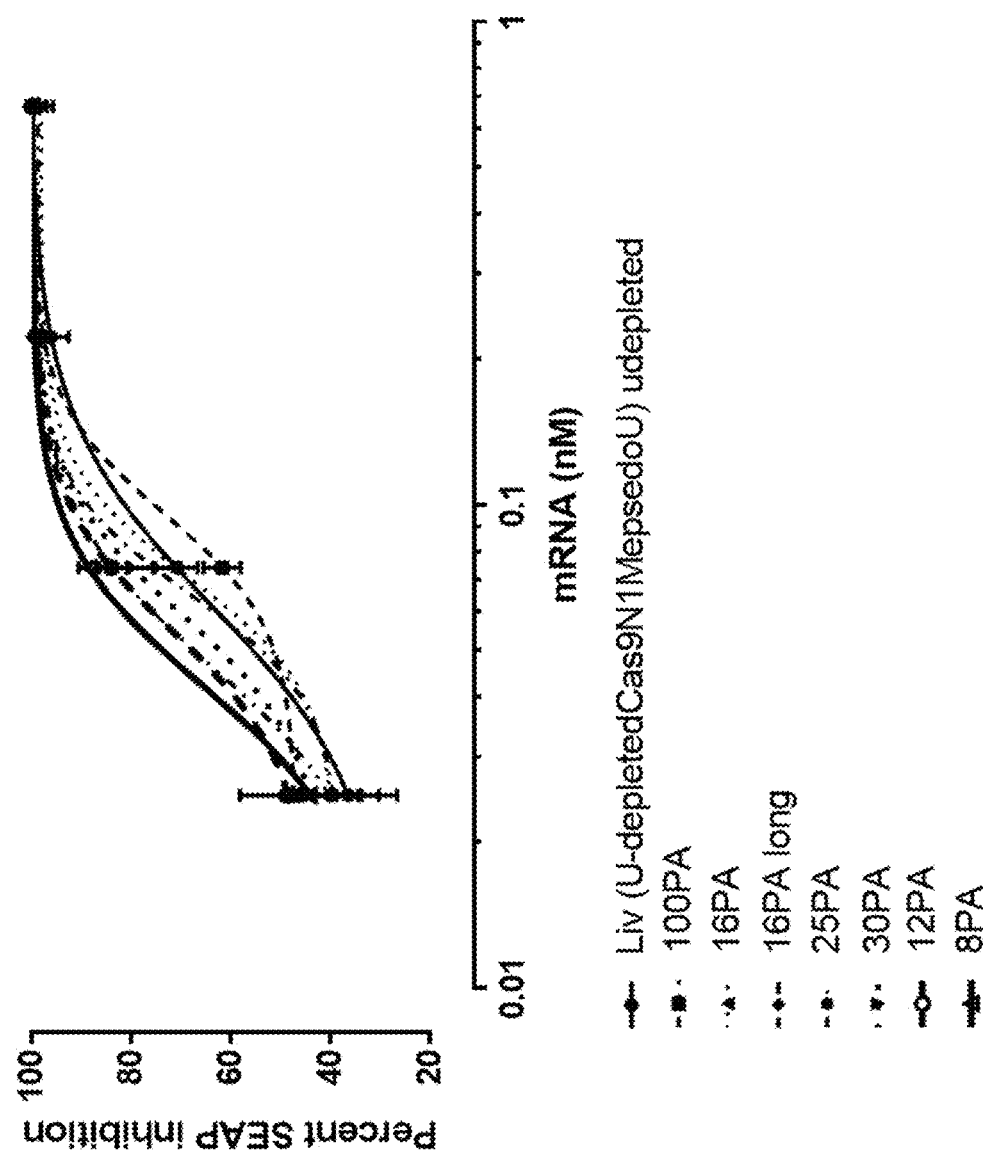
FIG. 7 shows percent SEAP inhibition measured in a Cas9 mRNA assay using Cas9 mRNA with a poly-A tails containing only adenosines or Cas9 mRNA with a poly-A tails comprising non-adenine nucleotides and single guide RNA targeting SEAP (SEQ ID NO: 8) with a 48-hour incubation.

FIG. 7 shows titration of Cas9 mRNA with adenosine-only poly-A [100PA] or the poly-A of SEQ ID NO: 2, SEQ ID NO: 3, SEQ ID NO: 4, SEQ ID NO: 5, SEQ ID NO: 10, or SEQ ID NO: 11 in the HEK-Blue cell assay at concentrations from 0.02-6 nM, and 1 µM single guide RNA targeting SEAP (SEQ ID NO: 8). Specifically, FIG. 7 shows percent SEAP inhibition for the constructs after a 48-hour incubation, and EC50 values are provided in Table 3, below. All constructs are active.

TABLE 3

EC50 values for SEAP inhibition

| PolyA | Cas9 mRNA Construct | EC50 | Standard Error |
| --- | --- | --- | --- |
| 98 consecutive adenosines | Liv (U- depleted Cas9 N1Me pseudo U) | 0.0627 | 0.0118 |
| 97 consecutive adenosines | 100 PA | 0.0956 | 0.0041 |
| SEQ ID NO: 4 | 16 PA | 0.0692 | 0.0087 |
| SEQ ID NO: 5 | 16 PA long | 0.0705 | 2.237 |
| SEQ ID NO: 3 | 25 PA | 0.0500 | 0.0213 |
| SEQ ID NO: 2 | 30 PA | 0.0591 | 0.0086 |

TABLE 3-continued

EC50 values for SEAP inhibition

| PolyA | Cas9 mRNA Construct | EC50 | Standard Error |
| --- | --- | --- | --- |
| SEQ ID NO: 10 | 12 PA | 0.0549 | 0.0296 |
| SEQ ID NO: 11 | 8 PA | 0.04233 | 0.0295 |

Example 4—Cloning of Long PolyA with Interrupting Sequences

A 300 nucleotide long polyA tail, SEQ ID NO:18 [300pa], was designed comprising twelve interrupting sequences from Table 4 (below) and 13 repeats of 12 consecutive adenosines. Anchor Sequences of SEQ ID NOT: 18 were designed to minimize hybridization and self-annealing between trinucleotide interrupting sequences within the ~300 nt the poly-A tail. Table 4 below provides interrupting sequences that minimize annealing between interrupting sequences, and include the anchors used in this experiment.

To clone SEQ ID NO: 18, each of sequences PolyA-1 (SEQ ID NO: 12), PolyA-2 (SEQ ID NO: 13), PolyA-3 (SEQ ID NO: 14), and PolyA-4 (SEQ ID NO: 15) are created in the pUC57 mini vector (Genscript). The pA1-2 plasmid is created by amplifying SEQ ID NO:12 with Bcl11a primers, digesting the PCR product with restriction enzymes XhoI and AclI and ligating the restriction fragment into the pA2 plasmid comprising SEQ ID NO: 13 digested with XhoI and BstBI. The pA3-4 plasmid is created in the same manner amplifying SEQ ID NO: 14 and ligating it into the same restriction sites on plasmid pA4. The pA1-4 plasmid (comprising SEQ ID NO:18) is assembled by amplifying the SEQ ID NO: 17 sequence from pA3-4, digesting the PCR fragment with BbsI and XbaI restriction enzymes and cloning the restriction fragment into the polyA 1-2 (SEQ ID NO: 16) construct digested with BbsI and XbaI restriction enzymes. The inserts into pA1-2 and pA3-4 are assessed by Sanger sequencing from both directions using [pUC-M seq2 forward primer and pUC-M seq reverse primer] as primers (SEQ ID Nos: 20 and 21).

The resulting SEQ ID NO: 18 (300PA) polyA sequence is excised by digesting pA1-4 with XhoI and XbaI for cloning into the same sites in a protein encoding vector. All steps are carried out under standard conditions.

TABLE 4

| | | |
| --- | --- | --- |
| CGG | CGT | CGC |
| CTG | CTT | CTC |
| CAG | CAT | CAC |
| CCC | CCG | CCT |
| | | |
| GGG | GGT | GGC |
| GCG | GCT | GCC |
| GAG | GAT | GAC |
| GTG | GTT | GTC |
| | | |
| TGG | TGT | TGC |
| TTG | TTT | TTC |
| TAG | TAT | TAC |
| TCG | TTC | TCC |

I claim:

1. A DNA comprising nucleotides encoding a poly-adenylated (poly-A) tail located 3' to nucleotides encoding a protein of interest, wherein the poly-A tail comprises:
   a. three or more homopolymer sequences of at least 8 consecutive adenine (A) nucleotides; and
   b. an interrupting sequence comprising:
      i. one non-adenine nucleotide; or
      ii. a consecutive stretch of 2-10 non-adenine nucleotides, between each homopolymer sequence.

2. The DNA of claim 1, wherein one or more of the three or more homopolymer sequences comprises at least 10, 15, 20, 25, 30, 35, or 40 consecutive adenine nucleotides.

3. The DNA of claim 1, wherein the interrupting sequence prevents the loss of one or more adenine nucleotide during DNA replication as compared to the loss that occurs in a DNA comprising a 3' tail of a similar or same length that contains only adenine nucleotides.

4. The DNA of claim 1, wherein the interrupting sequence is positioned to interrupt the consecutive adenine nucleotides so that a poly(A) binding protein can bind to a stretch of consecutive adenine nucleotides.

5. The DNA of claim 1, wherein the poly-A tail comprises at least 50 total adenine nucleotides.

6. The DNA of claim 1, wherein the poly-A tail comprises 40-1000, 40-900, 40-800, 40-700, 40-600, 40-500, 40-400, 40-300, 40-200, or 40-100 total adenine nucleotides.

7. The DNA of claim 1, wherein the poly-A tail comprises 95-100 total adenine nucleotides.

8. The DNA of claim 1, wherein the interrupting sequence is located after at least 8-50 consecutive adenine nucleotides.

9. The DNA of claim 1, wherein the interrupting sequence is a trinucleotide, dinucleotide or mononucleotide interrupting sequence.

10. The DNA of claim 1, wherein the interrupting sequence is positioned every 8-50 consecutive adenine nucleotides.

11. The DNA of claim 1, wherein the poly-A tail comprises one non-adenine nucleotide or 2, 3, 4, or 5 consecutive non-adenine nucleotides every 12, 16, 25, 30, or 39 consecutive adenine nucleotides.

12. The DNA of claim 1, wherein the non-adenine nucleotide is chosen from guanine, cytosine, and thymine.

13. The DNA of claim 12, comprising more than one non-adenine nucleotide selected from:
   a. guanine and thymine nucleotides;
   b. guanine and cytosine nucleotides;
   c. thymine and cytosine nucleotides; and
   d. guanine, thymine and cytosine nucleotides.

14. The DNA of claim 1, wherein the non-adenine nucleotide consists of one non-adenine nucleotide selected from guanine, cytosine, and thymine;
   wherein the non-adenine nucleotides comprise two non-adenine nucleotides selected from one or more of guanine, cytosine, and thymine; or
   wherein the non-adenine nucleotides comprise three non-adenine nucleotides selected from one or more of guanine, cytosine, and thymine.

15. The DNA of claim 1, wherein the adenine nucleotides are adenosine monophosphate.

16. The DNA of claim 1, wherein the protein is a therapeutic protein.

17. The DNA of claim 16, wherein the protein is a cytokine, chemokine, a growth factor, an RNA-guided nuclease, class 2 CRISPR-associated Cas endonuclease, chimeric Cas protein, Cas9, or modified Cas9.

18. A mRNA encoded by the DNA of claim 1.

19. The DNA of claim 1, wherein the DNA is within a vector.

20. A host cell comprising the DNA of claim 1.

21. The DNA of claim 19, wherein the interrupting sequence prevents loss of nucleotides encoding the poly-A tail within the vector during growth of the host cell as compared to the loss that occurs in a DNA comprising nucleotides encoding a poly-A tail of a similar or same length that contains only adenine nucleotides.

22. A method of producing mRNA from the DNA vector of claim 19, comprising:
   a. linearizing the vector downstream of the poly-A tail;
   b. denaturing the linearized vector; and
   c. contacting the denaturized DNA with an RNA polymerase in the presence of guanine, cytosine, uracil, and adenine nucleotides.

* * * * *

SEQUENCE LISTING

<160> NUMBER OF SEQ ID NOS: 31

<210> SEQ ID NO 1
<211> LENGTH: 108
<212> TYPE: DNA
<213> ORGANISM: Artificial Sequence
<220> FEATURE:
<223> OTHER INFORMATION: Synthetic: mRNA sequence of an exemplary poly-A
      tail comprising non-adenine nucleotides with 30, 30, and 39
      consecutive adenosines and ending with non-adenine nucleotides

<400> SEQUENCE: 1
aaaaaaaaaa aaaaaaaaaa aaaaaaaaaa gcgaaaaaaa aaaaaaaaaa aaaaaaaaaa      60
aaaccgaaaa aaaaaaaaaa aaaaaaaaaa aaaaaaaaaa aaaaaccc                  108

<210> SEQ ID NO 2
<211> LENGTH: 104
<212> TYPE: DNA
<213> ORGANISM: Artificial Sequence
<220> FEATURE:
<223> OTHER INFORMATION: Synthetic: 30PA - sequence of an exemplary
      poly-A tail comprising non-adenine nucleotides with 30, 30, and 39
      consecutive adenosines

<400> SEQUENCE: 2
aaaaaaaaaa aaaaaaaaaa aaaaaaaaaa gcgaaaaaaa aaaaaaaaaa aaaaaaaaaa      60
aaaccgaaaa aaaaaaaaaa aaaaaaaaaa aaaaaaaaaa aaaa                      104

<210> SEQ ID NO 3
<211> LENGTH: 109
<212> TYPE: DNA
<213> ORGANISM: Artificial Sequence
<220> FEATURE:
<223> OTHER INFORMATION: Synthetic: 25PA - sequence of an exemplary
      poly-A tail comprising non-adenine nucleotides with four sets of
      25 consecutive adenosines

<400> SEQUENCE: 3
aaaaaaaaaa aaaaaaaaaa aaaaagcgaa aaaaaaaaaa aaaaaaaaaa aaaccgaaaa      60
aaaaaaaaaa aaaaaaaaaa agtgaaaaaa aaaaaaaaaa aaaaaaaaa                 109

<210> SEQ ID NO 4
<211> LENGTH: 101
<212> TYPE: DNA
<213> ORGANISM: Artificial Sequence
<220> FEATURE:
<223> OTHER INFORMATION: Synthetic: 16PA - sequence of an exemplary
      poly-A tail comprising non-adenine nucleotides with six sets of 16
      consecutive adenosines

<400> SEQUENCE: 4
aaaaaaaaaa aaaaagaaa aaaaaaaaaa aaacaaaaaa aaaaaaaaaa taaaaaaaa       60 aaaaaaataa aaaaaaaaaa aaacaaaaa aaaaaaaaaa a                          101

<210> SEQ ID NO 5
<211> LENGTH: 165
<212> TYPE: DNA
<213> ORGANISM: Artificial Sequence
<220> FEATURE:
<223> OTHER INFORMATION: Synthetic: 16PA long - sequence of an exemplary
      poly-A tail comprising non-adenine nucleotides with six sets of 16
      consecutive adenosines and 63 consecutive adenosines

<400> SEQUENCE: 5
aaaaaaaaaa aaaaagaaa aaaaaaaaaa aaacaaaaaa aaaaaaaaaa taaaaaaaa       60

| | |
|---|---|
| aaaaaaataa aaaaaaaaaa aaaacaaaaa aaaaaaaaaa acaaaaaaaa aaaaaaaaaa | 120 |
| aaaaaaaaaa aaaaaaaaaa aaaaaaaaaa aaaaaaaaaa aaaaa | 165 |

<210> SEQ ID NO 6
<211> LENGTH: 4523
<212> TYPE: DNA
<213> ORGANISM: Artificial Sequence
<220> FEATURE:
<223> OTHER INFORMATION: Synthetic: Cas9 mRNA with a poly-A tail
      consisting of 97 adenosines

<400> SEQUENCE: 6

| | |
|---|---|
| taatacgact cactataggg tcccgcagtc ggcgtccagc ggctctgctt gttcgtgtgt | 60 |
| gtgtcgttgc aggccttatt cggatccatg gataagaagt actcaatcgg gctggatatc | 120 |
| ggaactaatt ccgtgggttg ggcagtgatc acggatgaat acaaagtgcc gtccaagaag | 180 |
| ttcaaggtcc tggggaacac cgatagacac agcatcaaga aaaatctcat cggagccctg | 240 |
| ctgtttgact ccggcgaaac cgcagaagcg acccggctca acgtaccgc gaggcgacgc | 300 |
| tacacccggc ggaagaatcg catctgctat ctgcaagaga tcttttcgaa cgaaatggca | 360 |
| aaggtcgacg acagcttctt ccaccgcctg gaagaatctt cctggtgga ggaggacaag | 420 |
| aagcatgaac ggcatcctat ctttggaaac atcgtcgacg aagtggcgta ccacgaaaag | 480 |
| tacccgacca tctaccatct gcggaagaag ttggttgact caactgacaa ggccgacctc | 540 |
| agattgatct acttggccct cgcccatatg atcaaattcc gcggacactt cctgatcgaa | 600 |
| ggcgatctga accctgataa ctccgacgtg gataagcttt tcattcaact ggtgcagacc | 660 |
| tacaaccaac tgttcgaaga aaacccaatc aatgctagcg gcgtcgatgc caaggccatc | 720 |
| ctgtccgccc ggctgtcgaa gtcgcggcgc tcgaaaaacc tgatcgcaca gctgccggga | 780 |
| gagaaaaaga acggactttt cggcaacttg atcgctctct cactgggact cactcccaat | 840 |
| ttcaagtcca ttttgacct ggccgaggac gcgaagctgc aactctcaaa ggacacctac | 900 |
| gacgacgact ggacaatttt gctggcacaa attggcgatc agtacgcgga tctgttcctt | 960 |
| gccgctaaga acctttcgga cgcaatcttg ctgtccgata tcctgcgcgt gaacaccgaa | 1020 |
| ataaccaaag cgccgcttag cgcctcgatg attaagcggt acgacgagca tcaccaggat | 1080 |
| ctcacgctgc tcaaagcgct cgtgagacag caactgcctg aaaagtacaa ggagatcttc | 1140 |
| ttcgaccagt ccaagaatgg gtacgcaggg tacatcgatg gaggcgctag ccaggaagag | 1200 |
| ttctataagt tcatcaagcc aatcctggaa aagatggacg gaaccgaaga actgctggtc | 1260 |
| aagctgaaca gggaggatct gctccggaaa cagagaacct ttgacaacgg atccattccc | 1320 |
| caccagatcc atctgggtga gctgcacgcc atcttgcggc gccaggagga cttttacccca | 1380 |
| ttcctcaagg acaaccggga aaagatcgag aaaattctga cgttccgcat cccgtattac | 1440 |
| gtgggcccac tggcgcgcgg caattcgcgc ttcgcgtgga tgactagaaa atcgagggaa | 1500 |
| accatcactc cttggaattt cgaggaagtt gtggataagg gagcttcggc acaaagcttc | 1560 |
| atcgaacgaa tgaccaactt cgacaagaat ctcccaaacg agaaggtgct tcctaagcac | 1620 |
| agcctccttt acgaatactt cactgtctac aacgaactga ctaaagtgaa atacgttact | 1680 |
| gaaggaatga ggaagccggc cttctgtcc ggagaacaga gaaagcaat tgtcgatctg | 1740 |
| ctgttcaaga ccaaccgcaa ggtgaccgtc aagcagctta agaggacta cttcaagaag | 1800 |
| atcgagtgtt tcgactcagt ggaaatcagc ggggtggagg acagattcaa cgcttcgctg | 1860 |
| ggaacctatc atgatctcct gaagatcatc aaggacaagg acttccttga caacgaggag | 1920 |

```
aacgaggaca tcctggaaga tatcgtcctg accttgaccc ttttcgagga tcgcgagatg    1980
atcgaggaga ggcttaagac ctacgctcat ctcttcgacg ataaggtcat gaaacaactc    2040
aagcgccgcc ggtacactgg ttggggccgc ctctcccgca agctgatcaa cggtattcgc    2100
gataaacaga gcggtaaaac tatcctggat ttcctcaaat cggatggctt cgctaatcgt    2160
aacttcatgc aattgatcca cgacgacagc ctgacctttg aggaggacat ccaaaaagca    2220
caagtgtccg gacagggaga ctcactccat gaacacatcg gaatctggc cggttcgccg    2280 gcgattaaga agggaattct gcaaactgtg aaggtggtcg acgagctggt gaaggtcatg    2340
ggacggcaca accggagaa tatcgtgatt gaaatggccc gagaaaacca gactacccag    2400
aagggccaga aaaactcccg cgaaaggatg aagcggatcg aagaaggaat caaggagctg    2460
ggcagccaga tcctgaaaga gcacccggtg aaaacacgc agctgcagaa cgagaagctc    2520
tacctgtact atttgcaaaa tggacgggac atgtacgtgg accaagagct ggacatcaat    2580
cggttgtctg attacgacgt ggaccacatc gttccacagt cctttctgaa ggatgactcg    2640
atcgataaca aggtgttgac tcgcagcgac aagaacagag ggaagtcaga taatgtgcca    2700
tcggaggagg tcgtgaagaa gatgaagaat tactggcggc agctcctgaa tgcgaagctg    2760
attacccaga gaaagtttga caatctcact aaagccgagc gcggcggact ctcagagctg    2820
gataaggctg gattcatcaa acggcagctg gtcgagactc ggcagattac caagcacgtg    2880
gcgcagatct tggactcccg catgaacact aaatacgacg agaacgataa gctcatccgg    2940
gaagtgaagg tgattaccct gaaaagcaaa cttgtgtcgg actttcggaa ggactttcag    3000
ttttacaaag tgagagaaat caacaactac catcacgcgc atgacgcata cctcaacgct    3060
gtggtcggta ccgcccctgat caaaaagtac cctaaacttg aatcggagtt tgtgtacgga    3120
gactacaagg tctacgacgt gaggaagatg atagccaagt ccgaacagga aatcgggaaa    3180
gcaactgcga aatacttctt ttactcaaac atcatgaact ttttcaagac tgaaattacg    3240
ctggccaatg gagaaatcag gaagaggcca ctgatcgaaa ctaacggaga aacgggcgaa    3300
atcgtgtggg acaagggcag ggacttcgca actgttcgca aagtgctctc tatgccgcaa    3360
gtcaatattg tgaagaaaac cgaagtgcaa accggcggat tttcaaagga atcgatcctc    3420
ccaaagagaa atagcgacaa gctcattgca cgcaagaaag actgggaccc gaagaagtac    3480
ggaggattcg attcgccgac tgtcgcatac tccgtcctcg tggtggccaa ggtggagaag    3540
ggaaagagca aaagctcaa atccgtcaaa gagctgctgg ggattaccat catggaacga    3600
tcctcgttcg agaagaaccc gattgatttc ctcgaggcga agggttacaa ggaggtgaag    3660
aaggatctga tcatcaaact ccccaagtac tcactgttcg aactggaaaa tggtcggaag    3720
cgcatgctgg cttcggccgg agaactccaa aaaggaaatg agctgccctt gcctagcaag    3780
tacgtcaact tcctctatct tgcttcgcac tacgaaaaac tcaaagggtc accggaagat    3840
aacgaacaga agcagctttt cgtggagcag cacaagcatt atctggatga aatcatcgaa    3900
caaatctccg agttttcaaa gcgcgtgatc ctcgccgacg ccaacctcga caaagtcctg    3960
tcggcctaca ataagcatag agataagccg atcagagaac aggccgagaa cattatccac    4020
ttgttcaccc tgactaacct gggagcccca gccgccttca gtacttcga tactactatc    4080 gatcgcaaaa gatacacgtc caccaaggaa gttctggacg cgaccctgat ccaccaaagc    4140
atcactggac tctacgaaac taggatcgat ctgtcgcagc tgggtggcga tggcggtgga    4200
tctccgaaaa agaagagaaa ggtgtaatga gctagccatc acatttaaaa gcatctcagc    4260
```

```
ctaccatgag aataagagaa agaaaatgaa gatcaatagc ttattcatct cttttctttt    4320
ttcgttggtg taaagccaac accctgtcta aaaaacataa atttctttaa tcattttgcc    4380
tcttttctct gtgcttcaat taataaaaaa tggaaagaac ctcgagaaaa aaaaaaaaaa    4440
aaaaaaaaaa aaaaaaaaaa aaaaaaaaaa aaaaaaaaaa aaaaaaaaaa aaaaaaaaaa    4500
aaaaaaaaaa aaaaaaaaaa aaa                                           4523
```

<210> SEQ ID NO 7
<211> LENGTH: 4581
<212> TYPE: DNA
<213> ORGANISM: Artificial Sequence
<220> FEATURE:
<223> OTHER INFORMATION: Synthetic: T7 promoter and Cas9 mRNA with a
      poly-A tail comprising SEQ ID NO: 1

<400> SEQUENCE: 7

```
taatacgact cactataggg tcccgcagtc ggcgtccagc ggctctgctt gttcgtgtgt      60
gtgtcgttgc aggccttatt cggatctgcc accatggata agaagtactc gatcgggctg     120
gatatcggaa ctaattccgt gggttgggca gtgatcacgg atgaatacaa agtgccgtcc     180
aagaagttca aggtcctggg gaacaccgat agacacagca tcaagaagaa tctcatcgga     240
gccctgctgt ttgactccgg cgaaaccgca gaagcgaccc ggctcaaacg taccgcgagg     300
cgacgctaca cccggcggaa gaatcgcatc tgctatctgc aagaaatctt ttcgaacgaa     360
atggcaaagg tggacgacag cttcttccac cgcctggaag aatctttcct ggtggaggag     420
gacaagaagc atgaacggca tcctatcttt ggaaacatcg tggacgaagt ggcgtaccac     480
gaaaagtacc cgaccatcta ccatctgcgg aagaagttgg ttgactcaac tgacaaggcc     540
gacctcagat tgatctactt ggccctcgcc catatgatca aattccgcgg acacttcctg     600
atcgaaggcg atctgaaccc tgataactcc gacgtggata agctgttcat tcaactggtg     660
cagacctaca accaactgtt cgaagaaaac ccaatcaatg ccagcggcgt cgatgccaag     720
gccatcctgt ccgcccggct gtcgaagtcg cggcgcctcg aaaacctgat cgcacagctg     780
ccgggagaga agaagaacgg acttttcggc aacttgatcg ctctctcact gggactcact     840
cccaatttca gtccaatttt gaccctggcc gaggacgcga agctgcaact ctcaaaggac     900
acctacgacg acgacttgga caatttgctg gcacaaattg gcgatcagta cgcggatctg     960
ttccttgccg ctaagaacct ttcggacgca atcttgctgt ccgatatcct gcgcgtgaac    1020
accgaaataa ccaaagcgcc gcttagcgcc tcgatgatta agcggtacga cgagcatcac    1080
caggatctca cgctgctcaa agcgctcgtg agacagcaac tgcctgaaaa gtacaaggag    1140
attttcttcg accagtccaa gaatgggtac gcagggtaca tcgatggagg cgccagccag    1200
gaagagttct ataagttcat caagccaatc ctggaaaaga tggacggaac cgaagaactg    1260
ctggtcaagc tgaacaggga ggatctgctc cgcaaacaga gaaccctttga caacggaagc    1320 attccacacc agatccatct gggtgagctg cacgccatct gcggcgcca ggaggacttt    1380 tacccattcc tcaaggacaa ccgggaaaag atcgagaaaa ttctgacgtt ccgcatcccg    1440
tattacgtgg gcccactggc gcgcggcaat tcgcgcttcg cgtggatgac tagaaaatca    1500
gaggaaacca tcactccttg gaatttcgag gaagttgtgg ataagggagc ttcggcacaa    1560
tccttcatcg aacgaatgac caacttcgac aagaatctcc caaacgagaa ggtgcttcct    1620
aagcacagcc tctttacga atacttcact gtctacaacg aactgactaa agtgaaatac    1680
gttactgaag gaatgaggaa gccggccttt ctgagcggag aacagaagaa agcgattgtc    1740
```

```
gatctgctgt tcaagaccaa ccgcaaggtg accgtcaagc agcttaaaga ggactacttc      1800
aagaagatcg agtgtttcga ctcagtggaa atcagcggag tggaggacag attcaacgct      1860
tcgctgggaa cctatcatga tctcctgaag atcatcaagg acaaggactt ccttgacaac      1920
gaggagaacg aggacatcct ggaagatatc gtcctgacct tgacccttt tcgaggatcgc      1980 gagatgatcg aggagaggct aagacctac gctcatctct tcgacgataa ggtcatgaaa      2040
caactcaagc gccgccggta cactggttgg ggccgcctct cccgcaagct gatcaacggt      2100
attcgcgata acagagcgg taaaactatc ctggatttcc tcaaatcgga tggcttcgct      2160
aatcgtaact tcatgcagtt gatccacgac gacagcctga cctttaagga ggacatccag      2220
aaagcacaag tgagcggaca gggagactca ctccatgaac acatcgcgaa tctggccggt      2280
tcgccggcga ttaagaaggg aatcctgcaa actgtgaagg tggtggacga gctggtgaag      2340
gtcatgggac ggcacaaacc ggagaatatc gtgattgaaa tggcccgaga aaaccagact      2400
acccagaagg gccagaagaa ctcccgcgaa aggatgaagc ggatcgaaga aggaatcaag      2460
gagctgggca gccagatcct gaaagagcac ccggtggaaa acacgcagct gcagaacgag      2520
aagctctacc tgtactattt gcaaaatgga cgggacatgt acgtggacca agagctggac      2580
atcaatcggt tgtctgatta cgacgtggac cacatcgttc acagtccttt ctgaaggat      2640 gactccatcg ataacaaggt gttgactcgc agcgacaaga acagagggaa gtcagataat      2700
gtgccatcgg aggaggtcgt gaagaagatg aagaattact ggcggcagct cctgaatgcg      2760
aagctgatta cccagagaaa gtttgacaat ctcactaaag ccgagcgcgg cggactctca      2820
gagctggata aggctggatt catcaaacgg cagctggtcg agactcggca gattaccaag      2880
cacgtggcgc agatcctgga ctcccgcatg aacactaaat acgacgagaa cgataagctc      2940
atccgggaag tgaaggtgat taccctgaaa agcaaacttg tgtcggactt tcggaaggac      3000
tttcagtttt acaaagtgag agaaatcaac aactaccatc acgcgcatga cgcatacctc      3060
aacgctgtgg tcgcaccgc cctgatcaag aagtaccta aacttgaatc ggagtttgtg      3120
tacggagact acaaggtcta cgacgtgagg aagatgatag ccaagtccga acaggaaatc      3180
gggaaagcaa ctgcgaaata cttcttttac tcaaacatca tgaacttctt caagactgaa      3240
attacgctgg ccaatggaga aatcaggaag aggccactga tcgaaactaa cggagaaacg      3300
ggcgaaatcg tgtgggacaa gggcagggac ttcgcaactg ttcgcaaagt gctctctatg      3360
ccgcaagtca atattgtgaa gaaaaccgaa gtgcaaaccg gcggattttc aaaggaatcg      3420
atcctcccaa agagaaatag cgacaagctc attgcacgca agaaagactg ggacccgaag      3480
aagtacggag gattcgattc gccgactgtc gcatactccg tcctcgtggt ggccaaggtg      3540
gagaagggaa agagcaagaa gctcaaatcc gtcaaagagc tgctggggat taccatcatg      3600
gaacgatcct cgttcgagaa gaacccgatt gatttcctgg aggcgaaggg ttacaaggag      3660
gtgaagaagg atctgatcat caaactgccc aagtactcac tgttcgaact ggaaaatggt      3720
cggaagcgca tgctggcttc ggccggagaa ctccagaaag gaaatgagct ggccttgcct      3780
agcaagtacg tcaacttcct ctatcttgct tcgcactacg agaaactcaa agggtcaccg      3840
gaagataacg aacagaagca gcttttcgtg gagcagcaca gcattatct ggatgaaatc      3900 atcgaacaaa tctccgagtt ttcaaagcgc gtgatcctcg ccgacgccaa cctcgacaaa      3960
gtcctgtcgg cctacaataa gcatagagat aagccgatca gagaacaggc cgagaacatt      4020
atccacttgt tcacccctgac taacctggga gctccagccg ccttcaagta cttcgatact      4080
actatcgacc gcaaaagata cacgtccacc aaggaagttc tggacgcgac cctgatccac      4140
```

```
caaagcatca ctggactcta cgaaactagg atcgatctgt cgcagctggg tggcgatggt    4200
ggcggtggat cctacccata cgacgtgcct gactacgcct ccggaggtgg tggccccaag    4260
aagaaacgga aggtgtgata gctagccatc acatttaaaa gcatctcagc ctaccatgag    4320
aataagagaa agaaaatgaa gatcaatagc ttattcatct cttttctttt ttcgttggtg    4380
taaagccaac accctgtcta aaaacataa atttctttaa tcattttgcc tcttttctct     4440
gtgcttcaat taataaaaaa tggaaagaac ctcgagaaaa aaaaaaaaaa aaaaaaaaa     4500 aaaaaagcga aaaaaaaaa aaaaaaaaa aaaaaaaac cgaaaaaaaa aaaaaaaaa       4560 aaaaaaaaaa aaaaaaaaa a                                              4581

<210> SEQ ID NO 8
<211> LENGTH: 100
<212> TYPE: RNA
<213> ORGANISM: Artificial Sequence
<220> FEATURE:
<223> OTHER INFORMATION: Synthetic: Single guide RNA targeting SEAP
<220> FEATURE:
<221> NAME/KEY: modified_base
<222> LOCATION: (1)..(3)
<223> OTHER INFORMATION: Each nucleotide modified with 2'-O-Me and is
      linked to the next nucleotide with a Phosphorothioate (PS) linkage
      or bond
<220> FEATURE:
<221> NAME/KEY: modified_base
<222> LOCATION: (29)..(39)
<223> OTHER INFORMATION: 2'-O-Me
<220> FEATURE:
<221> NAME/KEY: modified_base
<222> LOCATION: (68)..(96)
<223> OTHER INFORMATION: 2'-O-Me
<220> FEATURE:
<221> NAME/KEY: modified_base
<222> LOCATION: (97)..(99)
<223> OTHER INFORMATION: Each nucleotide modified with 2'-O-Me and is
      linked to the next nucleotide with a Phosphorothioate (PS) linkage
      or bond
<220> FEATURE:
<221> NAME/KEY: modified_base
<222> LOCATION: (100)..(100)
<223> OTHER INFORMATION: 2'-O-Me

<400> SEQUENCE: 8
cucccugaug gagaugacag guuuuagagc uagaaauagc aaguuaaaau aaggcuaguc    60
cguuaucaac uugaaaaagu ggcaccgagu cggugcuuuu                         100

<210> SEQ ID NO 9
<211> LENGTH: 100
<212> TYPE: RNA
<213> ORGANISM: Artificial Sequence
<220> FEATURE:
<223> OTHER INFORMATION: Synthetic: Single guide RNA targeting mouse TTR
<220> FEATURE:
<221> NAME/KEY: modified_base
<222> LOCATION: (1)..(3)
<223> OTHER INFORMATION: Each nucleotide modified with 2'-O-Me and is
      linked to the next nucleotide with a Phosphorothioate (PS) linkage
      or bond
<220> FEATURE:
<221> NAME/KEY: modified_base
<222> LOCATION: (29)..(39)
<223> OTHER INFORMATION: 2'-O-Me
<220> FEATURE:
<221> NAME/KEY: modified_base
<222> LOCATION: (68)..(96)
<223> OTHER INFORMATION: 2'-O-Me
<220> FEATURE:
<221> NAME/KEY: modified_base
<222> LOCATION: (97)..(99)
```

```
<223> OTHER INFORMATION: Each nucleotide modified with 2'-O-Me and is
      linked to the next nucleotide with a Phosphorothioate (PS) linkage
      or bond
<220> FEATURE:
<221> NAME/KEY: modified_base
<222> LOCATION: (100)..(100)
<223> OTHER INFORMATION: 2'-O-Me

<400> SEQUENCE: 9
uuacagccac gucuacagca guuuuagagc uagaaauagc aaguuaaaau aaggcuaguc    60
cguuaucaac uugaaaaagu ggcaccgagu cggugcuuuu                         100

<210> SEQ ID NO 10
<211> LENGTH: 116
<212> TYPE: DNA
<213> ORGANISM: Artificial Sequence
<220> FEATURE:
<223> OTHER INFORMATION: Synthetic: 12PA - mRNA sequence of an exemplary
      poly-A tail comprising non-adenine nucleotides with nine sets of
      12 consecutive adenosines and mononucleotide interrupting
      sequences

<400> SEQUENCE: 10
aaaaaaaaaa aataaaaaaa aaaataaaaa aaaaaaaaca aaaaaaaaaa ataaaaaaaa    60
aaaacaaaaa aaaaaaagaa aaaaaaaaaa caaaaaaaaa aaataaaaaa aaaaaa        116

<210> SEQ ID NO 11
<211> LENGTH: 115
<212> TYPE: DNA
<213> ORGANISM: Artificial Sequence
<220> FEATURE:
<223> OTHER INFORMATION: Synthetic: 8PA - mRNA sequence of an exemplary
      poly-A tail comprising non-adenine nucleotides with twelve sets of
      8 consecutive adenosines and mononucleotide interrupting sequences

<400> SEQUENCE: 11
aaaaaaaata aaaaaaataa aaaaaacaaa aaaaaaaaaa aaagaaaaaa aataaaaaaa    60
acaaaaaaaa caaaaaaaat aaaaaaaaga aaaaaaacaa aaaaaataaa aaaaa         115

<210> SEQ ID NO 12
<211> LENGTH: 159
<212> TYPE: DNA
<213> ORGANISM: Artificial Sequence
<220> FEATURE:
<223> OTHER INFORMATION: Synthetic: PolyA-1, Bcl11a primer annealing
      sites flanking sequence comprising five interrupting sequences
      separating six repeats of 12 consecutive adenosines

<400> SEQUENCE: 12
tcttccttca gtctgtaaac ctcagctcga gaaaaaaaaa aaatggaaaa aaaaaaaacg    60
gaaaaaaaaa aaaggtaaaa aaaaaaaata taaaaaaaaa aaacataaaa aaaaaaaacg    120
ttcatatcgg ttctagacca cacttcttac tgaggtccc                          159

<210> SEQ ID NO 13
<211> LENGTH: 188
<212> TYPE: DNA
<213> ORGANISM: Artificial Sequence
<220> FEATURE:
<223> OTHER INFORMATION: Synthetic: PolyA-2, Bcl11a primer annealing
      sites flanking sequence comprising five interrupting sequences
      separating six sets of 12 consecutive adenosines

<400> SEQUENCE: 13
tcttccttca gtctgtaaac ctcagaattc atctagctcg agaaaaaatt cgaaaaaaaa    60
```

```
aaaacgtaaa aaaaaaaaac tcaaaaaaaa aaaagataaa aaaaaaaaac ctaaaaaaaa      120
aaaatgtaaa aaaaaaaaag ggaaagtctt ccatatcggt tctagaccac acttcttact      180
gaggtccc                                                                188

<210> SEQ ID NO 14
<211> LENGTH: 170
<212> TYPE: DNA
<213> ORGANISM: Artificial Sequence
<220> FEATURE:
<223> OTHER INFORMATION: Synthetic: PolyA-3, Bcl11a primer annealing
      sites flanking sequence comprising five interrupting sequences
      separating six sets of 12 consecutive adenosines

<400> SEQUENCE: 14
tcttccttca gtctgtaaac ctcagctcga ggaagacaag ggaaaaaaaa aaaacgcaaa       60
aaaaaaaaac acaaaaaaaa aaaatgcaaa aaaaaaaaat cgaaaaaaaa aaaatctaaa      120
aaaaaaaaac gttcatatcg gttctagacc acacttctta ctgaggtccc                 170

<210> SEQ ID NO 15
<211> LENGTH: 171
<212> TYPE: DNA
<213> ORGANISM: Artificial Sequence
<220> FEATURE:
<223> OTHER INFORMATION: Synthetic: PolyA-4, Blc11a primer annealing
      sites flanking sequence comprising six interrupting sequences
      separating seven sets of 12 consecutive adenosines

<400> SEQUENCE: 15
tcttccttca gtctgtaaac ctcagctcga gaaaaaattc gaaaaaaaaa aaacccaaaa       60
aaaaaaaaga caaaaaaaaa aaatagaaaa aaaaaaaagt taaaaaaaaa aaactgaaaa      120
aaaaaaaatt taaaaaaaaa aaatctagac cacacttctt actgaggtcc c               171

<210> SEQ ID NO 16
<211> LENGTH: 267
<212> TYPE: DNA
<213> ORGANISM: Artificial Sequence
<220> FEATURE:
<223> OTHER INFORMATION: Synthetic: PolyA 1-2, Blc11a primer annealing
      sites flanking sequence comprising 11 interrupting sequences
      separating 12 sets of 12 consecutive adenosines

<400> SEQUENCE: 16
tcttccttca gtctgtaaac ctcagaattc atctagctcg agaaaaaaaa aaaatggaaa       60
aaaaaaaaac ggaaaaaaaa aaaaggtaaa aaaaaaaaat ataaaaaaaa aaaacataaa      120
aaaaaaaaac gaaaaaaaaa aaacgtaaaa aaaaaaaact caaaaaaaaa aaagataaaa      180
aaaaaaaacc taaaaaaaaa aaatgtaaaa aaaaaaaagg gaaagtcttc catatcggtt      240
ctagaccaca cttcttactg aggtccc                                          267

<210> SEQ ID NO 17
<211> LENGTH: 261
<212> TYPE: DNA
<213> ORGANISM: Artificial Sequence
<220> FEATURE:
<223> OTHER INFORMATION: Synthetic: PolyA 3-4, Blc11a primer annealing
      sites flanking sequence comprising 12 interrupting sequences
      separating 13 sets of 12 consecutive adenosines

<400> SEQUENCE: 17
tcttccttca gtctgtaaac ctcagctcga ggaagacaag ggaaaaaaaa aaaacgcaaa       60
aaaaaaaaac acaaaaaaaa aaaatgcaaa aaaaaaaaat cgaaaaaaaa aaaatctaaa      120
```

```
aaaaaaaaac gaaaaaaaaa aaacccaaaa aaaaaaaaga caaaaaaaaa aaatagaaaa      180
aaaaaaaagt taaaaaaaaa aaactgaaaa aaaaaaaatt taaaaaaaaa aaatctagac      240
cacacttctt actgaggtcc c                                                261
```

<210> SEQ ID NO 18
<211> LENGTH: 370
<212> TYPE: DNA
<213> ORGANISM: Artificial Sequence
<220> FEATURE:
<223> OTHER INFORMATION: Synthetic: 300pa, mRNA sequence of an exemplary
      poly-A tail comprising 24 interrupting sequences separating 13
      repeats of 12 consecutive adenosines

<400> SEQUENCE: 18

```
aaaaaaaaaa aatggaaaaa aaaaaaacgg aaaaaaaaaa aaggtaaaaa aaaaaaatat      60
aaaaaaaaaa aacataaaaa aaaaaaacga aaaaaaaaaa acgtaaaaaa aaaaaactca     120
aaaaaaaaaa agataaaaaa aaaaaaccta aaaaaaaaaa atgtaaaaaa aaaaaaggga     180
aaaaaaaaaa acgcaaaaaa aaaaaacaca aaaaaaaaaa atgcaaaaaa aaaaaatcga     240
aaaaaaaaaa atctaaaaaa aaaaaacgaa aaaaaaaaaa cccaaaaaaa aaaaagacaa     300
aaaaaaaaaa tagaaaaaaa aaaagttaa aaaaaaaaaa ctgaaaaaaa aaaaatttaa      360
aaaaaaaaaa                                                           370
```

<210> SEQ ID NO 19
<211> LENGTH: 97
<212> TYPE: DNA
<213> ORGANISM: Artificial Sequence
<220> FEATURE:
<223> OTHER INFORMATION: Synthetic: 100PA - sequence of an exemplary
      poly-A tail comprising 97 adenine nucleotide homopolymer

<400> SEQUENCE: 19

```
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaa                              97
```

<210> SEQ ID NO 20
<211> LENGTH: 20
<212> TYPE: DNA
<213> ORGANISM: Artificial Sequence
<220> FEATURE:
<223> OTHER INFORMATION: Synthetic: pUC-M seq2 forward primer

<400> SEQUENCE: 20

```
gggttattgt ctcatgagcg                                                  20
```

<210> SEQ ID NO 21
<211> LENGTH: 20
<212> TYPE: DNA
<213> ORGANISM: Artificial Sequence
<220> FEATURE:
<223> OTHER INFORMATION: Synthetic: pUC-M seq reverse primer

<400> SEQUENCE: 21

```
ttttgtgatg ctcgtcaggg                                                  20
```

<210> SEQ ID NO 22
<211> LENGTH: 25
<212> TYPE: DNA
<213> ORGANISM: Artificial Sequence
<220> FEATURE:
<223> OTHER INFORMATION: Synthetic: RN-Bcl11a for

```
<400> SEQUENCE: 22
tcttccttca gtctgtaaac ctcag                                              25

<210> SEQ ID NO 23
<211> LENGTH: 22
<212> TYPE: DNA
<213> ORGANISM: Artificial Sequence
<220> FEATURE:
<223> OTHER INFORMATION: Synthetic: RN-Bcl11a rev

<400> SEQUENCE: 23
gggacctcag taagaagtgt gg                                                 22

<210> SEQ ID NO 24
<211> LENGTH: 4506
<212> TYPE: DNA
<213> ORGANISM: Artificial Sequence
<220> FEATURE:
<223> OTHER INFORMATION: Synthetic: Liv-Udepleted: Cas9 mRNA with a
      poly-A tail consisting of 98 consecutive adenosines

<400> SEQUENCE: 24
tcccgcagtc ggcgtccagc ggctctgctt gttcgtgtgt gtgtcgttgc aggccttatt        60
cggatccgcc accatggaca agaagtacag catcggactg acatcggaa caaacagcgt        120 cggatgggca gtcatcacag acgaatacaa ggtcccgagc aagaagttca ggtcctggg        180 aaacacagac agacacagca tcaagaagaa cctgatcgga gcactgctgt tcgacagcgg       240
agaaacagca gaagcaacaa gactgaagag aacagcaaga agaagataca aagaagaaa       300 gaacagaatc tgctacctgc aggaaatctt cagcaacgaa atggcaaagg tcgacgacag       360
cttcttccac agactggaag aaagcttcct ggtcgaagaa gacaagaagc acgaaagaca       420
cccgatcttc ggaaacatcg tcgacgaagt cgcataccac gaaaagtacc cgacaatcta       480
ccacctgaga aagaagctgg tcgacagcac agacaaggca gacctgagac tgatctacct       540
ggcactggca cacatgatca gttcagagg acacttcctg atcgaggag acctgaaccc        600 ggacaacagc gacgtcgaca gctgttcat ccagctggtc cagacataca accagctgtt       660
cgaagaaaac ccgatcaacg caagcggagt cgacgcaaag gcaatcctga gcgcaagact       720
gagcaagagc agaagactgg aaaacctgat cgcacagctg ccgggagaaa agaagaacgg       780
actgttcgga aacctgatcg cactgagcct gggactgaca ccgaacttca gagcaacttt       840
cgacctggca gaagacgcaa agctgcagct gagcaaggac acatacgacg acgacctgga       900
caacctgctg gcacagatcg agaccagta cgcagacctg ttcctggcag caaagaacct       960
gagcgacgca atcctgctga gcgacatcct gagagtcaac acagaaatca aaaggcacc      1020 gctgagcgca agcatgatca gagatacga cgaacaccac caggacctga cactgctgaa      1080
ggcactggtc agacagcagc tgccggaaaa gtacaaggaa atcttcttcg accagagcaa      1140
gaacggatac gcaggataca tcgacggagg agcaagccga gaagaattct acaagttcat      1200
caagccgatc ctggaaaaga tggacggaac agaagaactg ctggtcaagc tgaacagaga      1260
agacctgctg agaaagcaga gaacattcga caacggaagc atcccgcacc agatccacct      1320
gggagaactg cacgcaatcc tgagaagaca ggaagactte tacccgttcc tgaaggacaa      1380
cagagaaaag atcgaaaaga tcctgacatt cagaatcccg tactacgtcg gaccgctggc      1440
aagaggaaac agcagattcg catggatgac aagaaagagc gaagaaacaa tcacaccgtg      1500
gaacttcgaa gaagtcgtcg acaagggagc aagcgcacag agcttcatcg aaagaatgac      1560
```

```
aaacttcgac aagaacctgc cgaacgaaaa ggtcctgccg aagcacagcc tgctgtacga    1620
atacttcaca gtctacaacg aactgacaaa ggtcaagtac gtcacagaag gaatgagaaa    1680
gccggcattc ctgagcggag aacagaagaa ggcaatcgtc gacctgctgt tcaagacaaa    1740
cagaaaggtc acagtcaagc agctgaagga agactacttc aagaagatcg aatgcttcga    1800
cagcgtcgaa atcagcggag tcgaagacag attcaacgca agcctgggaa cataccacga    1860
cctgctgaag atcatcaagg acaaggactt cctggacaac gaagaaaacg aagacatcct    1920
ggaagacatc gtcctgacac tgacactgtt cgaagacaga gaaatgatcg aagaaagact    1980
gaagacatac gcacacctgt tcgacgacaa ggtcatgaag cagctgaaga agaagaagata    2040
cacaggatgg ggaagactga gcagaaagct gatcaacgga atcagagaca agcagagcgg    2100
aaagacaatc ctggacttcc tgaagagcga cggattcgca aacagaaact tcatgcagct    2160
gatccacgac gacagcctga cattcaagga agacatccag aaggcacagg tcagcggaca    2220
gggagacagc ctgcacgaac acatcgcaaa cctggcagga agcccggcaa tcaagaaggg    2280
aatcctgcag acagtcaagg tcgtcgacga actggtcaag gtcatgggaa gacacaagcc    2340
ggaaaacatc gtcatcgaaa tggcaagaga aaaccagaca cacagaaagg gacagaagaa    2400
cagcagagaa agaatgaaga gaatcgaaga aggaatcaag gaactgggaa gccagatcct    2460
gaaggaacac ccggtcgaaa acacacagct gcagaacgaa aagctgtacc tgtactacct    2520
gcagaacgga agagacatgt acgtcgacca ggaactggac atcaacagac tgagcgacta    2580
cgacgtcgac cacatcgtcc cgcagagctt cctgaaggac gacagcatcg acaacaaggt    2640
cctgacaaga agcgacaaga acagaggaaa gagcgacaac gtcccgagcg aagaagtcgt    2700
caagaagatg aagaactact ggagacagct gctgaacgca agctgatca cacagagaaa    2760
gttcgacaac ctgacaaagg cagagagagg aggactgagc gaactggaca aggcaggatt    2820
catcaagaga cagctggtcg aaacaagaca gatcacaaag cacgtcgcac agatcctgga    2880
cagcagaatg aacacaaagt acgacgaaaa cgacaagctg atcagagaag tcaaggtcat    2940
cacactgaag agcaagctgg tcagcgactt cagaaaggac ttccagttct acaaggtcag    3000
agaaatcaac aactaccacc acgcacacga cgcatacctg aacgcagtcg tcggaacagc    3060
actgatcaag aagtacccga agctggaaag cgaattcgtc tacggagact acaaggtcta    3120
cgacgtcaga aagatgatcg caaagagcga acaggaaatc ggaaaggcaa cagcaaagta    3180
cttcttctac agcaacatca tgaacttctt caagacagaa atcacactgg caaacggaga    3240
aatcagaaag agaccgctga tcgaaacaaa cggagaaaca ggagaaatcg tctgggacaa    3300
gggaagagac ttcgcaacag tcagaaaggt cctgagcatg ccgcaggtca catcgtcaa    3360
gaagacagaa gtccagacag gaggattcag caaggaaagc atcctgccga agagaaacag    3420
cgacaagctg atcgcaagaa agaaggactg ggacccgaag aagtacggag gattcgacag    3480
cccgacagtc gcatacagcg tcctggtcgt cgcaaaggtc gaaaagggaa agagcaagaa    3540
gctgaagagc gtcaaggaac tgctgggaat cacaatcatg gaaagaagca gcttcgaaaa    3600
gaacccgatc gacttcctgg aagcaaaggg atacaaggaa gtcaagaagg acctgatcat    3660
caagctgccg aagtacagcc tgttcgaact ggaaaacgga agaaagagaa tgctggcaag    3720
cgcaggagaa ctgcagaagg gaaacgaact ggcactgccg agcaagtacg tcaacttcct    3780
gtacctggca agccactacg aaaagctgaa gggaagcccg gaagacaacg aacagaagca    3840
gctgttcgtc gaacagcaca gcactacct ggacgaaatc atcgaacaga tcagcgaatt    3900
```

-continued

```
cagcaagaga gtcatcctgg cagacgcaaa cctggacaag gtcctgagcg catacaacaa    3960
gcacagagac aagccgatca gagaacaggc agaaaacatc atccacctgt tcacactgac    4020
aaacctggga gcaccggcag cattcaagta cttcgacaca caatcgaca gaaagagata    4080 cacaagcaca aaggaagtcc tggacgcaac actgatccac cagagcatca caggactgta    4140
cgaaacaaga atcgacctga gccagctggg aggagacgga ggaggaagcc cgaagaagaa    4200
gagaaaggtc tagctagcca tcacatttaa aagcatctca gcctaccatg agaataagag    4260
aaagaaaatg aagatcaata gcttattcat ctcttttttct tttcgttgg tgtaaagcca    4320 acaccctgtc taaaaaacat aaatttcttt aatcattttg cctcttttct ctgtgcttca    4380
attaataaaa aatggaaaga acctcgagaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaa                                                               4506
```

<210> SEQ ID NO 25
<211> LENGTH: 4512
<212> TYPE: DNA
<213> ORGANISM: Artificial Sequence
<220> FEATURE:
<223> OTHER INFORMATION: Synthetic: Cas9 mRNA with a poly-A tail
      comprising SEQ ID NO: 3

<400> SEQUENCE: 25

```
tcccgcagtc ggcgtccagc ggctctgctt gttcgtgtgt gtgtcgttgc aggccttatt      60
cggatccgcc accatggaca agaagtacag catcggactg acatcggaa caaacagcgt     120 cggatgggca gtcatcacag acgaatacaa ggtcccgagc aagaagttca aggtcctggg     180
aaacacagac agacacagca tcaagaagaa cctgatcgga gcactgctgt tcgacagcgg     240
agaaacagca gaagcaacaa gactgaagag aacagcaaga agaagataca aagaagaaa     300 gaacagaatc tgctacctgc aggaaatctt cagcaacgaa atggcaaagg tcgacgacag     360
cttcttccac agactggaag aaagcttcct ggtcgaagaa gacaagaagc acgaaagaca     420
cccgatcttc ggaaacatcg tcgacgaagt cgcataccac gaaaagtacc cgacaatcta     480
ccacctgaga aagaagctgg tcgacagcac agacaaggca gacctgagac tgatctacct     540
ggcactggca cacatgatca gttcagagg acacttcctg atcgaaggag acctgaaccc     600
ggacaacagc gacgtcgaca gctgttcat ccagctggtc cagacataca accagctgtt     660
cgaagaaaac ccgatcaacg caagcggagt cgacgcaaag gcaatcctga gcgcaagact     720
gagcaagagc agaagactgg aaaacctgat cgcacagctg ccgggagaaa agaagaacgg     780
actgttcgga aacctgatcg cactgagcct gggactgaca ccgaacttca agagcaactt     840
cgacctggca gaagacgcaa agctgcagct gagcaaggac acatacgacg acgacctgga     900
caacctgctg gcacagatcg agaccagta cgcagacctg ttcctggcag caaagaacct     960
gagcgacgca atcctgctga gcgacatcct gagagtcaac acagaaatca caaaggcacc    1020
gctgagcgca agcatgatca gagatacga cgaacaccac caggacctga cactgctgaa    1080
ggcactggtc agacagcagc tgccggaaaa gtacaaggaa atcttcttcg accagagcaa    1140
gaacggatac gcaggataca tcgacggagg agcaagccaa gaagaattct acaagttcat    1200
caagccgatc ctggaaaaga tggacggaac agaagaactg ctggtcaagc tgaacagaga    1260
agacctgctg agaaagcaga gaacattcga caacggaagc atcccgcacc agatccacct    1320
gggagaactg cacgcaatcc tgagaagaca ggaagacttc tacccgttcc tgaaggacaa    1380
```

```
cagagaaaag atcgaaaaga tcctgacatt cagaatcccg tactacgtcg gaccgctggc    1440
aagaggaaac agcagattcg catggatgac aagaaagagc gaagaaacaa tcacaccgtg    1500
gaacttcgaa gaagtcgtcg acaagggagc aagcgcacag agcttcatcg aaagaatgac    1560
aaacttcgac aagaacctgc cgaacgaaaa ggtcctgccg aagcacagcc tgctgtacga    1620
atacttcaca gtctacaacg aactgacaaa ggtcaagtac gtcacagaag aatgagaaa    1680 gccggcattc ctgagcggag aacagaagaa ggcaatcgtc gacctgctgt tcaagacaaa    1740
cagaaaggtc acagtcaagc agctgaagga agactacttc aagaagatcg aatgcttcga    1800
cagcgtcgaa atcagcggag tcgaagacag attcaacgca agcctgggaa cataccacga    1860
cctgctgaag atcatcaagg acaaggactt cctggacaac gaagaaaacg aagacatcct    1920
ggaagacatc gtcctgacac tgacactgtt cgaagacaga gaaatgatcg aagaaagact    1980
gaagacatac gcacacctgt tcgacgacaa ggtcatgaag cagctgaaga gaagaagata    2040
cacaggatgg ggaagactga gcagaaagct gatcaacgga atcagagaca agcagagcgg    2100
aaagacaatc ctggacttcc tgaagagcga cggattcgca aacagaaact tcatgcagct    2160
gatccacgac gacagcctga cattcaagga agacatccag aaggcacagg tcagcggaca    2220
gggagacagc ctgcacgaac acatcgcaaa cctggcagga agcccggcaa tcaagaaggg    2280
aatcctgcag acagtcaagg tcgtcgacga actggtcaag gtcatgggaa gacacaagcc    2340
ggaaaacatc gtcatcgaaa tggcaagaga aaaccagaca cacagaaggg acagaagaa    2400 cagcagagaa agaatgaaga gaatcgaaga aggaatcaag gaactgggaa gccagatcct    2460
gaaggaacac ccgtcgaaa acacacagct gcagaacgaa aagctgtacc tgtactacct    2520
gcagaacgga agagacatgt acgtcgacca ggaactggac atcaacagac tgagcgacta    2580
cgacgtcgac cacatcgtcc cgcagagctt cctgaaggac gacagcatcg acaacaaggt    2640
cctgacaaga agcgacaaga acagaggaaa gagcgacaac gtcccgagcg aagaagtcgt    2700
caagaagatg aagaactact ggagacagct gctgaacgca aagctgatca cacagagaaa    2760
gttcgacaac ctgacaaagg cagagagagg aggactgagc gaactggaca aggcaggatt    2820
catcaagaga cagctggtcg aaacaagaca gatcacaaag cacgtcgcac agatcctgga    2880
cagcagaatg aacacaaagt acgacgaaaa cgacaagctg atcagagaag tcaaggtcat    2940
cacactgaag agcaagctgg tcagcgactt cagaaaggac ttccagttct acaaggtcag    3000
agaaatcaac aactaccacc acgcacacga cgcatacctg aacgcagtcg tcggaacagc    3060
actgatcaag aagtacccga agctggaaag cgaattcgtc tacggagact acaaggtcta    3120
cgacgtcaga aagatgatcg caaagagcga acaggaaatc ggaaaggcaa cagcaaagta    3180
cttcttctac agcaacatca tgaacttctt caagacagaa atcacactgg caaacgaga    3240 aatcagaaag agaccgctga tcgaaacaaa cggagaaaca ggagaaatcg tctgggacaa    3300
gggaagagac ttcgcaacag tcagaaaggt cctgagcatg ccgcaggtca acatcgtcaa    3360
gaagacagaa gtccagacag gaggattcag caaggaaagc atcctgccga agagaaacag    3420
cgacaagctg atcgcaagaa agaaggactg ggacccgaag aagtacggag gattcgacag    3480
cccgacagtc gcatacagcg tcctggtcgt cgcaaaggtc gaaaagggaa agagcaagaa    3540
gctgaagagc gtcaaggaac tgctgggaat cacaatcatg gaaagaagca gcttcgaaaa    3600
gaacccgatc gacttcctgg aagcaaaggg atacaaggaa gtcaagaagg acctgatcat    3660
caagctgccg aagtacagcc tgttcgaact ggaaaacgaa gaaagagaa tgctggcaag    3720 cgcaggagaa ctgcagaagg gaaacgaact ggcactgccg agcaagtacg tcaacttcct    3780
```

```
gtacctggca agccactacg aaaagctgaa gggaagcccg aagacaacg aacagaagca      3840 gctgttcgtc aacagcaca agcactacct ggacgaaatc atcgaacaga tcagcgaatt      3900
cagcaagaga gtcatcctgg cagacgcaaa cctggacaag gtcctgagcg catacaacaa      3960
gcacagagac aagccgatca gagaacaggc agaaaacatc atccacctgt tcacactgac      4020
aaacctggga gcaccggcag cattcaagta cttcgacaca acaatcgaca gaaagagata      4080
cacaagcaca aaggaagtcc tggacgcaac actgatccac cagagcatca caggactgta      4140
cgaaacaaga atcgacctga ccagctgggg aggagacgga ggaggaagcc gaagaagaa      4200 gagaaaggtc tagctagcca tcacatttaa aagcatctca gcctaccatg agaataagag      4260
aaagaaaatg aagatcaata gcttattcat ctcttttct ttttcgttgg tgtaaagcca      4320
acaccctgtc taaaaaacat aaatttcttt aatcattttg cctcttttct ctgtgcttca      4380
attaataaaa aatggaaaga accaaaaaaa aaaaaaaaaa aaaaaaagc gaaaaaaaaa      4440 aaaaaaaaaa aaaaaaccga aaaaaaaaaa aaaaaaaaaa aaaagtgaaa aaaaaaaaaa      4500
aaaaaaaaaa aa                                                          4512

<210> SEQ ID NO 26
<211> LENGTH: 4504
<212> TYPE: DNA
<213> ORGANISM: Artificial Sequence
<220> FEATURE:
<223> OTHER INFORMATION: Synthetic: Cas9 mRNA with a poly-A tail
      comprising SEQ ID NO: 4

<400> SEQUENCE: 26
tcccgcagtc ggcgtccagc ggctctgctt gttcgtgtgt gtgtcgttgc aggccttatt        60
cggatccgcc accatggaca agaagtacag catcggactg gacatcggaa caaacagcgt       120
cggatgggca gtcatcacag acgaatacaa ggtcccgagc aagaagttca aggtcctggg       180
aaacacagac agacacagca tcaagaagaa cctgatcgga gcactgctgt tcgacagcgg       240
agaaacagca gaagcaacaa gactgaagag aacagcaaga agaagataca agaagagaaa       300
gaacagaatc tgctacctgc aggaaatctt cagcaacgaa atggcaaagg tcgacgacag       360
cttcttccac agactggaag aaagcttcct ggtcgaagaa gacaagaagc acgaaagaca       420
cccgatcttc ggaaacatcg tcgacgaagt cgcataccac gaaaagtacc cgacaatcta       480
ccacctgaga aagaagctgg tcgacagcac agacaaggca gacctgagac tgatctacct       540
ggcactggca cacatgatca gttcagagg acacttcctg atcgaaggag acctgaaccc       600
ggacaacagc gacgtcgaca gctgttcat ccagctggtc cagacataca accagctgtt       660
cgaagaaaac ccgatcaacg caagcggagt cgacgcaaag gcaatcctga gcgcaagact       720
gagcaagagc agaagactgg aaaacctgat cgcacagctg ccgggagaaa agaagaacgg       780
actgttcgga aacctgatcg cactgagcct gggactgaca ccgaacttca agagcaactt       840
cgacctggca gaagacgcaa agctgcagct gagcaaggac acatacgacg acgacctgga       900
caacctgctg gcacagatcg agaccagta cgcagacctg ttcctggcag caaagaacct       960
gagcgacgca atcctgctga gcgacatcct gagagtcaac acagaaatca caaaggcacc      1020
gctgagcgca agcatgatca gagatacga cgaacaccac caggacctga cactgctgaa      1080
ggcactggtc agacagcagc tgccggaaaa gtacaaggaa atcttcttcg accagagcaa      1140
gaacggatac gcaggataca tcgacggagg agcaagccag gaagaattct acaagttcat      1200
caagccgatc ctggaaaaga tggacggaac agaagaactg ctggtcaagc tgaacagaga      1260
```

```
agacctgctg agaaagcaga gaacattcga caacggaagc atcccgcacc agatccacct    1320
gggagaactg cacgcaatcc tgagaagaca ggaagacttc tacccgttcc tgaaggacaa    1380
cagagaaaag atcgaaaaga tcctgacatt cagaatcccg tactacgtcg gaccgctggc    1440
aagaggaaac agcagattcg catggatgac aagaaagagc gaagaaacaa tcacaccgtg    1500
gaacttcgaa gaagtcgtcg acaagggagc aagcgcacag agcttcatcg aaagaatgac    1560
aaacttcgac aagaacctgc cgaacgaaaa ggtcctgccg aagcacagcc tgctgtacga    1620
atacttcaca gtctacaacg aactgacaaa ggtcaagtac gtcacagaag aatgagaaa    1680 gccggcattc ctgagcggag aacagaagaa ggcaatcgtc gacctgctgt tcaagacaaa    1740
cagaaaggtc acagtcaagc agctgaagga agactacttc aagaagatcg aatgcttcga    1800
cagcgtcgaa atcagcggag tcgaagacag attcaacgca agcctgggaa cataccacga    1860
cctgctgaag atcatcaagg acaaggactt cctggacaac gaagaaaacg aagacatcct    1920
ggaagacatc gtcctgacac tgacactgtt cgaagacaga gaaatgatcg aagaaagact    1980
gaagacatac gcacacctgt cgacgacaa ggtcatgaag cagctgaaga aagaagata    2040 cacaggatgg ggaagactga gcagaaagct gatcaacgga atcagagaca agcagagcgg    2100
aaagacaatc ctggacttcc tgaagagcga cggattcgca aacagaaact tcatgcagct    2160
gatccacgac gacagcctga cattcaagga agacatccag aaggcacagg tcagcggaca    2220
gggagacagc ctgcacgaac acatcgcaaa cctggcagga agcccggcaa tcaagaaggg    2280
aatcctgcag acagtcaagg tcgtcgacga actggtcaag gtcatgggaa gacacaagcc    2340
ggaaaacatc gtcatcgaaa tggcaagaga aaaccagaca acacagaagg gacagaagaa    2400
cagcagagaa agaatgaaga gaatcgaaga aggaatcaag gaactgggaa gccagatcct    2460
gaaggaacac ccggtcgaaa cacacagct gcagaacgaa aagctgtacc tgtactacct    2520
gcagaacgga agagacatgt acgtcgacca ggaactggac atcaacagac tgagcgacta    2580
cgacgtcgac cacatcgtcc cgcagagctt cctgaaggac gacagcatcg acaacaaggt    2640
cctgacaaga agcgacaaga acagaggaaa gagcgacaac gtcccgagcg aagaagtcgt    2700
caagaagatg aagaactact ggagacagct gctgaacgca aagctgatca cacagagaaa    2760
gttcgacaac ctgacaaagg cagagagagg aggactgagc gaactggaca aggcaggatt    2820
catcaagaga cagctggtcg aaacaagaca gatcacaaag cacgtcgcac agatcctgga    2880
cagcagaatg aacacaaagt acgacgaaaa cgacaagctg atcagagaag tcaaggtcat    2940
cacactgaag agcaagctgg tcagcgactt cagaaaggac ttccagttct acaaggtcag    3000
agaaatcaac aactaccacc acgcacacga cgcatacctg aacgcagtcg tcggaacagc    3060
actgatcaag aagtacccga agctggaaag cgaattcgtc tacggagact acaaggtcta    3120
cgacgtcaga aagatgatcg caaagagcga acaggaaatc ggaaaggcaa cagcaaagta    3180
cttcttctac agcaacatca tgaacttctt caagacagaa atcacactgg caaacgagaa    3240
aatcagaaag agaccgctga tcgaaacaaa cggagaaaca ggagaaatcg tctgggacaa    3300
gggaagagac ttcgcaacag tcagaaaggt cctgagcatg ccgcaggtca acatcgtcaa    3360
gaagacagaa gtccagacag gaggattcag caaggaaagc atcctgccga agagaaacag    3420
cgacaagctg atcgcaagaa agaaggactg ggacccgaag aagtacggag gattcgacag    3480
cccgacagtc gcatacagcg tcctggtcgt cgcaaaggtc gaaagggaa agagcaagaa    3540 gctgaagagc gtcaaggaac tgctgggaat cacaatcatg gaagaagca gcttcgaaaa    3600
```

| | |
|---|---|
| gaacccgatc gacttcctgg aagcaaaggg atacaaggaa gtcaagaagg acctgatcat | 3660 |
| caagctgccg aagtacagcc tgttcgaact ggaaaacgga agaaagagaa tgctggcaag | 3720 |
| cgcaggagaa ctgcagaagg gaaacgaact ggcactgccg agcaagtacg tcaacttcct | 3780 |
| gtacctggca agccactacg aaaagctgaa gggaagcccg gaagacaacg aacagaagca | 3840 |
| gctgttcgtc gaacagcaca agcactacct ggacgaaatc atcgaacaga tcagcgaatt | 3900 |
| cagcaagaga gtcatcctgg cagacgcaaa cctggacaag gtcctgagcg catacaacaa | 3960 |
| gcacagagac aagccgatca gagaacaggc agaaaacatc atccacctgt tcacactgac | 4020 |
| aaacctggga gcaccggcag cattcaagta cttcgacaca caatcgaca gaaagagata | 4080 |
| cacaagcaca aaggaagtcc tggacgcaac actgatccac cagagcatca caggactgta | 4140 |
| cgaaacaaga atcgacctga gccagctggg aggagacgga ggaggaagcc cgaagaagaa | 4200 |
| gagaaaggtc tagctagcca tcacatttaa aagcatctca gcctaccatg agaataagag | 4260 |
| aaagaaaatg aagatcaata gcttattcat ctcttttct ttttcgttgg tgtaaagcca | 4320 |
| acaccctgtc taaaaaacat aaatttcttt aatcattttg cctcttttct ctgtgcttca | 4380 |
| attaataaaa aatggaaaga accaaaaaaa aaaaaaaag aaaaaaaaaa aaaaacaaa | 4440 |
| aaaaaaaaa aaataaaaaa aaaaaaaaaa taaaaaaaaa aaaaaacaa aaaaaaaaa | 4500 |
| aaaa | 4504 |

<210> SEQ ID NO 27
<211> LENGTH: 4568
<212> TYPE: DNA
<213> ORGANISM: Artificial Sequence
<220> FEATURE:
<223> OTHER INFORMATION: Synthetic: Cas9 mRNA with a poly-A tail
    comprising SEQ ID NO: 5

<400> SEQUENCE: 27

| | |
|---|---|
| tcccgcagtc ggcgtccagc ggctctgctt gttcgtgtgt gtgtcgttgc aggccttatt | 60 |
| cggatccgcc accatggaca agaagtacag catcggactg gacatcggaa caaacagcgt | 120 |
| cggatgggca gtcatcacag acgaatacaa ggtcccgagc aagaagttca aggtcctggg | 180 |
| aaacacagac agacacagca tcaagaagaa cctgatcgga gcactgctgt tcgacagcgg | 240 |
| agaaacagca gaagcaacaa gactgaagag aacagcaaga agaagataca aagaagaaa | 300 |
| gaacagaatc tgctacctgc aggaaatctt cagcaacgaa atggcaaagg tcgacgacag | 360 |
| cttcttccac agactggaag aaagcttcct ggtcgaagaa gacaagaagc acgaaagaca | 420 |
| cccgatcttc ggaaacatcg tcgacgaagt cgcataccac gaaaagtacc cgacaatcta | 480 |
| ccacctgaga aagaagctgg tcgacagcac agacaaggca gacctgagac tgatctacct | 540 |
| ggcactggca cacatgatca gttcagagg acacttcctg atcgaaggag acctgaaccc | 600 |
| ggacaacagc gacgtcgaca gctgttcat ccagctggtc cagacataca accagctgtt | 660 |
| cgaagaaaac ccgatcaacg caagcggagt cgacgcaaag gcaatcctga gcgcaagact | 720 |
| gagcaagagc agaagactgg aaaacctgat cgcacagctg ccgggagaaa agaagaacgg | 780 |
| actgttcgga aacctgatcg cactgagcct gggactgaca ccgaacttca agagcaactt | 840 |
| cgacctggca gaagacgcaa agctgcagct gagcaaggac acatacgacg acgacctgga | 900 |
| caacctgctg gcacagatcg agaccagta cgcagacctg ttcctggcag caagaacct | 960 |
| gagcgacgca atcctgctga gcgacatcct gagagtcaac acagaaatca caaaggcacc | 1020 |
| gctgagcgca agcatgatca gagatacga cgaacaccac caggacctga cactgctgaa | 1080 |

```
ggcactggtc agacagcagc tgccggaaaa gtacaaggaa atcttcttcg accagagcaa    1140
gaacggatac gcaggataca tcgacggagg agcaagccag gaagaattct acaagttcat    1200
caagccgatc ctggaaaaga tggacggaac agaagaactg ctggtcaagc tgaacagaga    1260
agacctgctg agaaagcaga gaacattcga acacggaagc atcccgcacc agatccacct    1320
gggagaactg cacgcaatcc tgagaagaca ggaagacttc tacccgttcc tgaaggacaa    1380
cagagaaaag atcgaaaaga tcctgacatt cagaatcccg tactacgtcg gaccgctggc    1440
aagaggaaac agcagattcg catggatgac aagaaagagc gaagaaacaa tcacaccgtg    1500
gaacttcgaa gaagtcgtcg acaagggagc aagcgcacag agcttcatcg aaagaatgac    1560
aaacttcgac aagaacctgc cgaacgaaaa ggtcctgccg aagcacagcc tgctgtacga    1620
atacttcaca gtctacaacg aactgacaaa ggtcaagtac gtcacagaag gaatgagaaa    1680
gccggcattc ctgagcggag aacagaagaa ggcaatcgtc gacctgctgt tcaagacaaa    1740
cagaaaggtc acagtcaagc agctgaagga agactacttc aagaagatcg aatgcttcga    1800
cagcgtcgaa atcagcggag tcgaagacag attcaacgca agcctgggaa cataccacga    1860
cctgctgaag atcatcaagg acaaggactt cctggacaac gaagaaaacg aagacatcct    1920
ggaagacatc gtcctgacac tgacactgtt cgaagacaga gaaatgatcg aagaaagact    1980
gaagacatac gcacacctgt tcgacgacaa ggtcatgaag cagctgaaga agaagaata    2040 cacaggatgg ggaagactga gcagaaagct gatcaacgga atcagagaca gcagagcgg    2100 aaagacaatc ctggacttcc tgaagagcga cggattcgca aacagaaact tcatgcagct    2160
gatccacgac gacagcctga cattcaagga agacatccag aaggcacagg tcagcggaca    2220
gggagacagc ctgcacgaac acatcgcaaa cctggcagga agcccggcaa tcaagaaggg    2280
aatcctgcag acagtcaagg tcgtcgacga actggtcaag gtcatgggaa gacacaagcc    2340
ggaaaacatc gtcatcgaaa tggcaagaga aaaccagaca acacagaagg gacagaagaa    2400
cagcagagaa agaatgaaga gaatcgaaga aggaatcaag gaactgggaa gccagatcct    2460
gaaggaacac ccggtcgaaa acacacagct gcagaacgaa aagctgtacc tgtactacct    2520
gcagaacgga agagacatgt acgtcgacca ggaactggac atcaacagac tgagcgacta    2580
cgacgtcgac cacatcgtcc cgcagagctt cctgaaggac gacagcatcg acaacaaggt    2640
cctgacaaga agcgacaaga acagaggaaa gagcgacaac gtcccgagcg aagaagtcgt    2700
caagaagatg aagaactact ggagacagct gctgaacgca aagctgatca cacagagaaa    2760
gttcgacaac ctgacaaagg cagagagagg aggactgagc gaactggaca aggcaggatt    2820
catcaagaga cagctggtcg aaacaagaca gatcacaaag cacgtcgcac agatcctgga    2880
cagcagaatg aacacaaagt acgacgaaaa cgacaagctg atcagagaag tcaaggtcat    2940
cacactgaag agcaagctgg tcagcgactt cagaaaggac ttccagttct acaaggtcag    3000
agaaatcaac aactaccacc acgcacacga cgcatacctg aacgcagtcg tcggaacagc    3060
actgatcaag aagtacccga agctggaaag cgaattcgtc tacggagact acaaggtcta    3120
cgacgtcaga aagatgatcg caaagagcga acaggaaatc ggaaaggcaa cagcaaagta    3180
cttcttctac agcaacatca tgaacttctt caagacagaa atcacactgg caaacggaga    3240
aatcagaaag agaccgctga tcgaaacaaa cggagaaaca ggagaaatcg tctgggacaa    3300
gggaagagac ttcgcaacag tcagaaaggt cctgagcatg ccgcaggtca acatcgtcaa    3360
gaagacagaa gtccagacag gaggattcag caaggaaagc atcctgccga agagaaacag    3420
cgacaagctg atcgcaagaa agaaggactg ggacccgaag aagtacggag gattcgacag    3480
```

```
cccgacagtc gcatacagcg tcctggtcgt cgcaaaggtc gaaaagggaa agagcaagaa    3540
gctgaagagc gtcaaggaac tgctgggaat cacaatcatg gaaagaagca gcttcgaaaa    3600
gaacccgatc gacttcctgg aagcaaaggg atacaaggaa gtcaagaagg acctgatcat    3660
caagctgccg aagtacagcc tgttcgaact ggaaaacgga agaaagagaa tgctggcaag    3720
cgcaggagaa ctgcagaagg gaaacgaact ggcactgccg agcaagtacg tcaacttcct    3780
gtacctggca agccactacg aaaagctgaa gggaagcccg aagacaacg aacagaagca    3840 gctgttcgtc gaacagcaca agcactacct ggacgaaatc atcgaacaga tcagcgaatt    3900
cagcaagaga gtcatcctgg cagacgcaaa cctggacaag gtcctgagcg catacaacaa    3960
gcacagagac aagccgatca gagaacaggc agaaaacatc atccacctgt tcacactgac    4020
aaacctggga gcaccggcag cattcaagta cttcgacaca caatcgaca gaaagagata    4080 cacaagcaca aggaagtcc tggacgcaac actgatccac cagagcatca caggactgta    4140
cgaaacaaga atcgacctga gccagctggg aggagacgga ggaggaagcc cgaagaagaa    4200
gagaaaggtc tagctagcca tcacatttaa agcatctca gcctaccatg agaataagag    4260
aaagaaaatg aagatcaata gcttattcat ctctttttct ttttcgttgg tgtaaagcca    4320
acaccctgtc taaaaaacat aaatttcttt aatcattttg cctctttttct ctgtgcttca    4380 attaataaaa aatggaaaga accaaaaaaa aaaaaaaaag aaaaaaaaaa aaaaacaaa    4440 aaaaaaaaaa aaataaaaaa aaaaaaaaaa taaaaaaaaa aaaaaaacaa aaaaaaaaaa    4500 aaacaaaaa aaaaaaaaaa aaaaaaaaaa aaaaaaaaaa aaaaaaaaaa aaaaaaaaaa    4560
aaaaaaaa                                                              4568

<210> SEQ ID NO 28
<211> LENGTH: 4519
<212> TYPE: DNA
<213> ORGANISM: Artificial Sequence
<220> FEATURE:
<223> OTHER INFORMATION: Synthetic: Cas9 mRNA with a poly-A tail
      comprising SEQ ID NO: 10

<400> SEQUENCE: 28
tcccgcagtc ggcgtccagc ggctctgctt gttcgtgtgt gtgtcgttgc aggccttatt      60
cggatccgcc accatggaca agaagtacag catcggactg acatcggaa caaacagcgt     120 cggatgggca gtcatcacag acgaatacaa ggtcccgagc aagaagttca aggtcctggg     180
aaacacagac agacacagca tcaagaagaa cctgatcgga gcactgctgt tcgacagcgg     240
agaaacagca gaagcaacaa gactgaagag aacagcaaga gaagataca caagaagaaa     300 gaacagaatc tgctacctgc aggaaatctt cagcaacgaa atggcaaagg tcgacgacag     360
cttcttccac agactggaag aaagcttcct ggtcgaagaa gacaagaagc acgaaagaca     420
cccgatcttc ggaaacatcg tcgacgaagt cgcataccac gaaaagtacc cgacaatcta     480
ccacctgaga aagaagctgg tcgacagcac agacaaggca gacctgagac tgatctacct     540
ggcactggca cacatgatca gttcagagg acacttcctg atcgaaggag acctgaaccc     600
ggacaacagc gacgtcgaca gctgttcat ccagctggtc cagacataca accagctgtt     660
cgaagaaaac ccgatcaacg caagcggagt cgacgcaaag gcaatcctga gcgcaagact     720
gagcaagagc agaagactgg aaaacctgat cgcacagctg ccgggagaaa agaagaacgg     780
actgttcgga aacctgatcg cactgagcct gggactgaca ccgaacttca gagcaacttc     840
cgacctggca gaagacgcaa agctgcagct gagcaaggac acatacgacg acgacctgga     900
```

```
caacctgctg gcacagatcg gagaccagta cgcagacctg ttcctggcag caaagaacct    960
gagcgacgca atcctgctga gcgacatcct gagagtcaac acagaaatca caaaggcacc   1020
gctgagcgca agcatgatca agagatacga cgaacaccac caggacctga cactgctgaa   1080
ggcactggtc agacagcagc tgccggaaaa gtacaaggaa atcttcttcg accagagcaa   1140
gaacggatac gcaggataca tcgacggagg agcaagccag gaagaattct acaagttcat   1200
caagccgatc ctggaaaaga tggacggaac agaagaactg ctggtcaagc tgaacagaga   1260
agacctgctg agaaagcaga gaacattcga caacggaagc atcccgcacc agatccacct   1320
gggagaactg cacgcaatcc tgagaagaca ggaagacttc tacccgttcc tgaaggacaa   1380
cagagaaaag atcgaaaaga tcctgacatt cagaatcccg tactacgtcg accgctggc    1440
aagaggaaac agcagattcg catggatgac aagaaagagc gaagaaacaa tcacaccgtg   1500
gaacttcgaa gaagtcgtcg acaagggagc aagcgcacag agcttcatcg aaagaatgac   1560
aaacttcgac aagaacctgc cgaacgaaaa ggtcctgccg aagcacagcc tgctgtacga   1620
atacttcaca gtctacaacg aactgacaaa ggtcaagtac gtcacagaag aatgagaaa    1680
gccggcattc ctgagcggag aacagaagaa ggcaatcgtc gacctgctgt tcaagacaaa   1740
cagaaaggtc acagtcaagc agctgaagga agactacttc aagaagatcg aatgcttcga   1800
cagcgtcgaa atcagcggag tcgaagacag attcaacgca agcctgggaa cataccacga   1860
cctgctgaag atcatcaagg acaaggactt cctggacaac gaagaaaacg aagacatcct   1920
ggaagacatc gtcctgacac tgacactgtt cgaagacaga gaaatgatcg aagaaagact   1980
gaagacatac gcacacctgt tcgacgacaa ggtcatgaag cagctgaaga agaagaata    2040
cacaggatgg ggaagactga gcagaaagct gatcaacgga atcagagaca agcagagcgg   2100
aaagacaatc ctggacttcc tgaagagcga cggattcgca aacagaaact tcatgcagct   2160
gatccacgac gacagcctga cattcaagga agacatccag aaggcacagg tcagcggaca   2220
gggagacagc ctgcacgaac acatcgcaaa cctggcagga agcccggcaa tcaagaaggg   2280
aatcctgcag acagtcaagg tcgtcgacga actggtcaag gtcatgggaa gacacaagcc   2340
ggaaaacatc gtcatcgaaa tggcaagaga aaaccagaca acacagaagg gacagaagaa   2400
cagcagagaa agaatgaaga gaatcgaaga aggaatcaag gaactgggaa gccagatcct   2460
gaaggaacac ccggtcgaaa acacacagct gcagaacgaa aagctgtacc tgtactacct   2520
gcagaacgga agagacatgt acgtcgacca ggaactggac atcaacagac tgagcgacta   2580
cgacgtcgac cacatcgtcc cgcagagctt cctgaaggac gacagcatcg acaacaaggt   2640
cctgacaaga agcgacaaga acagaggaaa gagcgacaac gtcccgagcg aagaagtcgt   2700
caagaagatg aagaactact ggagacagct gctgaacgca agctgatca cacagagaaa   2760
gttcgacaac ctgacaaagg cagagagagg aggactgagc gaactggaca aggcaggatt   2820
catcaagaga cagctggtcg aaacaagaca gatcacaaag cacgtcgcac agatcctgga   2880
cagcagaatg aacacaaagt acgacgaaaa cgacaagctg atcagagaag tcaaggtcat   2940
cacactgaag agcaagctgg tcagcgactt cagaaaggac ttccagttct acaaggtcag   3000
agaaatcaac aactaccacc acgcacacga cgcatacctg aacgcagtcg tcggaacagc   3060
actgatcaag aagtacccga agctggaaag cgaattcgtc tacggagact acaaggtcta   3120
cgacgtcaga aagatgatcg caaagagcga acaggaaatc ggaaaggcaa cagcaaagta   3180
cttcttctac agcaacatca tgaacttctt caagacagaa atcacactgg caaacggaga   3240
```

| | |
|---|---|
| aatcagaaag agaccgctga tcgaaacaaa cggagaaaca ggagaaatcg tctgggacaa | 3300 |
| gggaagagac ttcgcaacag tcagaaaggt cctgagcatg ccgcaggtca acatcgtcaa | 3360 |
| gaagacagaa gtccagacag gaggattcag caaggaaagc atcctgccga agagaaacag | 3420 |
| cgacaagctg atcgcaagaa agaaggactg gacccgaag aagtacggag gattcgcacg | 3480 |
| cccgacagtc gcatacagcg tcctggtcgt cgcaaaggtc gaaagggaa agagcaagaa | 3540 |
| gctgaagagc gtcaaggaac tgctgggaat cacaatcatg gaaagaagca gcttcgaaaa | 3600 |
| gaacccgatc gacttcctgg aagcaaaggg atacaaggaa gtcaagaagg acctgatcat | 3660 |
| caagctgccg aagtacagcc tgttcgaact ggaaaacgga gaaagagaa tgctggcaag | 3720 |
| cgcaggagaa ctgcagaagg gaaacgaact ggcactgccg agcaagtacg tcaacttcct | 3780 |
| gtacctggca agccactacg aaaagctgaa gggaagcccg gaagacaacg aacagaagca | 3840 |
| gctgttcgtc gaacagcaca agcactacct ggacgaaatc atcgaacaga tcagcgaatt | 3900 |
| cagcaagaga gtcatcctgg cagacgcaaa cctggacaag gtcctgagcg catacaacaa | 3960 |
| gcacagagac aagccgatca gagaacaggc agaaaacatc atccacctgt tcacactgac | 4020 |
| aaacctggga gcaccggcag cattcaagta cttcgacaca caatcgaca gaaagagata | 4080 |
| cacaagcaca aaggaagtcc tggacgcaac actgatccac cagagcatca caggactgta | 4140 |
| cgaaacaaga atcgacctga gccagctggg aggagacgga ggaggaagcc gaagaagaa | 4200 |
| gagaaaggtc tagctagcca tcacatttaa aagcatctca gcctaccatg agaataagag | 4260 |
| aaagaaaatg aagatcaata gcttattcat ctctttttct ttttcgttgg tgtaaagcca | 4320 |
| acaccctgtc taaaaaacat aaatttcttt aatcattttg cctcttttct ctgtgcttca | 4380 |
| attaataaaa aatggaaaga accaaaaaaa aaaataaaa aaaaaaata aaaaaaaaa | 4440 |
| acaaaaaaaa aaaataaaa aaaaaacaa aaaaaaaaa gaaaaaaaa aaacaaaaaa | 4500 |
| aaaaaataaa aaaaaaaa | 4519 |

<210> SEQ ID NO 29
<211> LENGTH: 4518
<212> TYPE: DNA
<213> ORGANISM: Artificial Sequence
<220> FEATURE:
<223> OTHER INFORMATION: Synthetic: Cas9 mRNA with a poly-A tail
      comprising SEQ ID NO: 11

<400> SEQUENCE: 29

| | |
|---|---|
| tcccgcagtc ggcgtccagc ggctctgctt gttcgtgtgt gtgtcgttgc aggccttatt | 60 |
| cggatccgcc accatggaca agaagtacag catcggactg gacatcggaa caaacagcgt | 120 |
| cggatgggca gtcatcacag acgaatacaa ggtcccgagc aagaagttca aggtcctggg | 180 |
| aaacacagac agacacagca tcaagaagaa cctgatcgga gcactgctgt tcgacagcgg | 240 |
| agaaacagca gaagcaacaa gactgaagag aacagcaaga agaagataca caagaagaaa | 300 |
| gaacagaatc tgctacctgc aggaaatctt cagcaacgaa atggcaaagg tcgacgacag | 360 |
| cttcttccac agactggaag aaagcttcct ggtcgaagaa gacaagaagc acgaaagaca | 420 |
| cccgatcttc ggaaacatcg tcgacgaagt cgcataccac gaaaagtacc cgacaatcta | 480 |
| ccacctgaga aagaagctgg tcgacagcac agacaaggca gacctgagac tgatctacct | 540 |
| ggcactggca cacatgatca gttcagagg acacttcctg atcgaaggag acctgaaccc | 600 |
| ggacaacagc gacgtcgaca agctgttcat ccagctggtc cagacataca accagctgtt | 660 |
| cgaagaaaac ccgatcaacg caagcggagt cgacgcaaag gcaatcctga gcgcaagact | 720 |

| | |
|---|---|
| gagcaagagc agaagactgg aaaacctgat cgcacagctg ccgggagaaa agaagaacgg | 780 |
| actgttcgga aacctgatcg cactgagcct gggactgaca ccgaacttca agagcaactt | 840 |
| cgacctggca gaagacgcaa agctgcagct gagcaaggac acatacgacg acgacctgga | 900 |
| caacctgctg gcacagatcg gagaccagta cgcagacctg ttcctggcag caaagaacct | 960 |
| gagcgacgca atcctgctga gcgacatcct gagagtcaac acagaaatca caaaggcacc | 1020 |
| gctgagcgca agcatgatca agagatacga cgaacaccac caggacctga cactgctgaa | 1080 |
| ggcactggtc agacagcagc tgccggaaaa gtacaaggaa atcttcttcg accagagcaa | 1140 |
| gaacggatac gcaggataca tcgacggagg agcaagccag gaagaattct acaagttcat | 1200 |
| caagccgatc ctggaaaaga tggacggaac agaagaactg ctggtcaagc tgaacagaga | 1260 |
| agacctgctg agaaagcaga gaacattcga caacggaagc atcccgcacc agatccacct | 1320 |
| gggagaactg cacgcaatcc tgagaagaca ggaagacttc tacccgttcc tgaaggacaa | 1380 |
| cagagaaaag atcgaaagag tcctgacatt cagaatcccg tactacgtcg accgctggc | 1440 |
| aagaggaaac agcagattcg catggatgac aagaaagagc gaagaaacaa tcacaccgtg | 1500 |
| gaacttcgaa gaagtcgtcg acaagggagc aagcgcacag agcttcatcg aaagaatgac | 1560 |
| aaacttcgac aagaacctgc cgaacgaaaa ggtcctgccg aagcacagcc tgctgtacga | 1620 |
| atacttcaca gtctacaacg aactgacaaa ggtcaagtac gtcacagaag gaatgagaaa | 1680 |
| gccggcattc ctgagcggag aacagaagaa ggcaatcgtc gacctgctgt tcaagacaaa | 1740 |
| cagaaaggtc acagtcaagc agctgaagga agactacttc aagaagatcg aatgcttcga | 1800 |
| cagcgtcgaa atcagcggag tcgaagacag attcaacgca agcctgggaa cataccacga | 1860 |
| cctgctgaag atcatcaagg acaaggactt cctggacaac gaagaaaacg aagacatcct | 1920 |
| ggaagacatc gtcctgacac tgacactgtt cgaagacaga gaaatgatcg aagaaagact | 1980 |
| gaagacatac gcacacctgt tcgacgacaa ggtcatgaag cagctgaaga agaagaagata | 2040 |
| cacaggatgg ggaagactga gcagaaagct gatcaacgga atcagagaca gcagagcgg | 2100 |
| aaagacaatc ctggacttcc tgaagagcga cggattcgca aacagaaact tcatgcagct | 2160 |
| gatccacgac gacagcctga cattcaagga agacatccag aaggcacagg tcagcggaca | 2220 |
| gggagacagc ctgcacgaac acatcgcaaa cctggcagga agcccggcaa tcaagaaggg | 2280 |
| aatcctgcag acagtcaagg tcgtcgacga actggtcaag gtcatgggaa gacacaagcc | 2340 |
| ggaaaacatc gtcatcgaaa tggcaagaga aaaccagaca acacagaagg gacagaagaa | 2400 |
| cagcagagaa agaatgaaga aatcgaagaa aggaatcaag gaactgggaa gccagatcct | 2460 |
| gaaggaacac ccggtcgaaa acacacagct gcagaacgaa aagctgtacc tgtactacct | 2520 |
| gcagaacgga agagacatgt acgtcgacca ggaactggac atcaacagac tgagcgacta | 2580 |
| cgacgtcgac cacatcgtcc cgcagagctt cctgaaggac gacagcatcg acaacaaggt | 2640 |
| cctgacaaga agcgacaaga acagaggaaa gagcgacaac gtcccgagcg aagaagtcgt | 2700 |
| caagaagatg aagaactact ggagacagct gctgaacgca aagctgatca cacagagaaa | 2760 |
| gttcgacaac ctgacaaagg cagagagagg aggactgagc gaactggaca aggcaggatt | 2820 |
| catcaagaga cagctggtcg aaacaagaca gatcacaaag cacgtcgcac agatcctgga | 2880 |
| cagcagaatg aacacaaagt acgacgaaaa cgacaagctg atcagagaag tcaaggtcat | 2940 |
| cacactgaag agcaagctgg tcagcgactt cagaaaggac ttccagttct acaaggtcag | 3000 |
| agaaatcaac aactaccacc acgcacacga cgcatacctg aacgcagtcg tcggaacagc | 3060 |
| actgatcaag aagtacccga agctggaaag cgaattcgtc tacggagact acaaggtcta | 3120 |

```
cgacgtcaga aagatgatcg caaagagcga acaggaaatc ggaaaggcaa cagcaaagta    3180
cttcttctac agcaacatca tgaacttctt caagacagaa atcacactgg caaacggaga    3240
aatcagaaag agaccgctga tcgaaacaaa cggagaaaca ggagaaatcg tctgggacaa    3300
gggaagagac ttcgcaacag tcagaaaggt cctgagcatg ccgcaggtca acatcgtcaa    3360
gaagacagaa gtccagacag gaggattcag caaggaaagc atcctgccga agagaaacag    3420
cgacaagctg atcgcaagaa agaaggactg ggaccgaag aagtacggag gattcgacag    3480
cccgacagtc gcatacagcg tcctggtcgt cgcaaaggtc gaaaagggaa gagcaagaa    3540 gctgaagagc gtcaaggaac tgctgggaat cacaatcatg gaagaagca gcttcgaaaa    3600 gaacccgatc gacttcctgg aagcaaaggg atacaaggaa gtcaagaagg acctgatcat    3660
caagctgccg aagtacagcc tgttcgaact ggaaaacgga gaaaagagaa tgctggcaag    3720
cgcaggagaa ctgcagaagg gaaacgaact ggcactgccg agcaagtacg tcaacttcct    3780
gtacctggca agccactacg aaaagctgaa gggaagcccg gaagacaacg aacagaagca    3840
gctgttcgtc gaacagcaca agcactacct ggacgaaatc atcgaacaga tcagcgaatt    3900
cagcaagaga gtcatcctgg cagacgcaaa cctggacaag gtcctgagcg catacaacaa    3960
gcacagagac aagccgatca gagaacaggc agaaaacatc atccacctgt tcacactgac    4020
aaacctggga gcaccggcag cattcaagta cttcgacaca caatcgaca gaaagagata    4080 cacaagcaca aaggaagtcc tggacgcaac actgatccac cagagcatca caggactgta    4140
cgaaacaaga atcgacctga gccagctggg aggagacgga ggaggaagcc cgaagaagaa    4200
gagaaaggtc tagctagcca tcacatttaa aagcatctca gcctaccatg agaataagag    4260 aaagaaatg aagatcaata gcttattcat ctcttttct ttttcgttgg tgtaaagcca    4320
acaccctgtc taaaaacat aaatttcttt aatcattttg cctcttttct ctgtgcttca    4380
attaataaaa aatggaaaga accaaaaaaa ataaaaaaaa taaaaaaac aaaaaaaaa    4440 aaaaagaaa aaaataaaa aaacaaaaa aacaaaaaa aataaaaaaa agaaaaaaa    4500 caaaaaaat aaaaaaaa                                                 4518
```

<210> SEQ ID NO 30
<211> LENGTH: 4500
<212> TYPE: DNA
<213> ORGANISM: Artificial Sequence
<220> FEATURE:
<223> OTHER INFORMATION: Synthetic: Cas9 mRNA with a poly-A tail
      comprising SEQ ID NO: 19

<400> SEQUENCE: 30

```
tcccgcagtc ggcgtccagc ggctctgctt gttcgtgtgt gtgtcgttgc aggccttatt      60
cggatccgcc accatggaca agaagtacag catcggactg gacatcggaa caaacagcgt     120
cggatgggca gtcatcacag acgaatacaa ggtcccgagc aagaagttca ggtcctggg     180 aaacacagac agacacagca tcaagaagaa cctgatcgga gcactgctgt tcgacagcgg    240
agaaacagca gaagcaacaa gactgaagag aacagcaaga agaagataca caagaagaaa    300
gaacagaatc tgctacctgc aggaaatctt cagcaacgaa atggcaaagg tcgacgacag    360
cttcttccac agactggaag aaagcttcct ggtcgaagaa gacaagaagc acgaaagaca    420
cccgatcttc ggaaacatcg tcgacgaagt cgcataccac gaaaagtacc cgacaatcta    480
ccacctgaga aagaagctgg tcgacagcac agacaaggca gacctgagac tgatcctacct    540 ggcactggca cacatgatca gttcagagg acacttcctg atcgaaggag acctgaaccc    600
```

```
ggacaacagc gacgtcgaca agctgttcat ccagctggtc cagacataca accagctgtt    660
cgaagaaaac ccgatcaacg caagcggagt cgacgcaaag gcaatcctga gcgcaagact    720
gagcaagagc agaagactgg aaaacctgat cgcacagctg ccgggagaaa agaagaacgg    780
actgttcgga aacctgatcg cactgagcct gggactgaca ccgaacttca agagcaactt    840
cgacctggca gaagacgcaa agctgcagct gagcaaggac acatacgacg acgacctgga    900
caacctgctg gcacagatcg gagaccagta cgcagacctt ttcctggcag caaagaacct    960
gagcgacgca atcctgctga gcgacatcct gagagtcaac acagaaatca caaaggcacc   1020
gctgagcgca agcatgatca agagatacga cgaacaccac caggacctga cactgctgaa   1080
ggcactggtc agacagcagc tgccggaaaa gtacaaggaa atcttcttcg accagagcaa   1140
gaacggatac gcaggataca tcgacggagg agcaagccag gaagaattct acaagttcat   1200
caagccgatc ctggaaaaga tggacggaac agaagaactg ctggtcaagc tgaacagaga   1260
agacctgctg agaaagcaga gaacattcga caacggaagc atcccgcacc agatccacct   1320
gggagaactg cacgcaatcc tgagaagaca ggaagacttc tacccgttcc tgaaggacaa   1380
cagagaaaag atcgaaaaga tcctgacatt cagaatcccg tactacgtcg accgctggc   1440 aagaggaaac agcagattcg catggatgac aagaaagagc gaagaaacaa tcacaccgtg   1500
gaacttcgaa gaagtcgtcg acaagggagc aagcgcacag agcttcatcg aaagaatgac   1560
aaacttcgac aagaacctgc cgaacgaaaa ggtcctgccg aagcacagcc tgctgtacga   1620
atacttcaca gtctcaaacg aactgacaaa ggtcaagtac gtcacagaag gaatgagaaa   1680
gccggcattc ctgagcggag aacagaagaa ggcaatcgtc gacctgctgt tcaagacaaa   1740
cagaaaggtc acagtcaagc agctgaagga agactacttc aagaagatcg aatgcttcga   1800
cagcgtcgaa atcagcggag tcgaagacag attcaacgca agcctgggaa cataccacga   1860
cctgctgaag atcatcaagg acaaggactt cctggacaac gaagaaaacg aagacatcct   1920
ggaagacatc gtcctgacac tgacactgtt cgaagacaga gaaatgatcg aagaaagact   1980
gaagacatac gcacacctgt tcgacgacaa ggtcatgaag cagctgaaga agaagaagata   2040 cacaggatgg ggaagactga gcagaaagct gatcaacgga atcagagaca gcagagcgg   2100 aaagacaatc ctggacttcc tgaagagcga cggattcgca aacagaaact tcatgcagct   2160
gatccacgac gacagcctga cattcaagga agacatccag aaggcacagg tcagcggaca   2220
gggagacagc ctgcacgaac acatcgcaaa cctggcagga agcccggcaa tcaagaaggg   2280
aatcctgcag acagtcaagg tcgtcgacga actggtcaag gtcatgggaa gacacaagcc   2340
ggaaaacatc gtcatcgaaa tggcaagaga aaaccagaca acacagaagg gacagaagaa   2400
cagcagagaa agaatgaaga gaatcgaaga aggaatcaag gaactgggaa gccagatcct   2460
gaaggaacac ccggtcgaaa acacacagct gcagaacgaa aagctgtacc tgtactacct   2520
gcagaacgga gagacatgt acgtcgacca ggaactggac atcaacagac tgagcgacta   2580
cgacgtcgac cacatcgtcc cgcagagctt cctgaaggac gacagcatcg acaacaaggt   2640
cctgacaaga agcgacaaga acagaggaaa gagcgacaac gtcccgagcg aagaagtcgt   2700
caagaagatg aagaactact ggagacagct gctgaacgca agctgatca cacagagaaa   2760 gttcgacaac ctgacaaagg cagagagagg aggactgagc gaactggaca aggcaggatt   2820
catcaagaga cagctggtcg aaacaagaca gatcacaaag cacgtcgcac agatcctgga   2880
cagcagaatg aacacaaagt acgacgaaaa cgacaagctg atcagagaag tcaaggtcat   2940
```

| | |
|---|---|
| cacactgaag agcaagctgg tcagcgactt cagaaaggac ttccagttct acaaggtcag | 3000 |
| agaaatcaac aactaccacc acgcacacga cgcatacctg aacgcagtcg tcggaacagc | 3060 |
| actgatcaag aagtacccga agctggaaag cgaattcgtc tacggagact acaaggtcta | 3120 |
| cgacgtcaga aagatgatcg caaagagcga acaggaaatc ggaaaggcaa cagcaaagta | 3180 |
| cttcttctac agcaacatca tgaacttctt caagacagaa atcacactgg caaacggaga | 3240 |
| aatcagaaag agaccgctga tcgaaacaaa cggagaaaca ggagaaatcg tctgggacaa | 3300 |
| gggaagagac ttcgcaacag tcagaaaggt cctgagcatg ccgcaggtca acatcgtcaa | 3360 |
| gaagacagaa gtccgacaga gaggattcag caaggaaagc atcctgccga gagaaacag | 3420 |
| cgacaagctg atcgcaagaa agaaggactg ggacccgaag aagtacggag gattcgacag | 3480 |
| cccgacagtc gcatacagcg tcctggtcgt cgcaaaggtc gaaagggaa agagcaagaa | 3540 |
| gctgaagagc gtcaaggaac tgctgggaat cacaatcatg gaaagaagca gcttcgaaaa | 3600 |
| gaacccgatc gacttcctgg aagcaaaggg atacaaggaa gtcaagaagg acctgatcat | 3660 |
| caagctgccg aagtacagcc tgttcgaact ggaaaacgga gaaagagaa tgctggcaag | 3720 |
| cgcaggagaa ctgcagaagg gaaacgaact ggcactgccg agcaagtacg tcaacttcct | 3780 |
| gtacctggca agccactacg aaaagctgaa gggaagcccg gaagacaacg aacagaagca | 3840 |
| gctgttcgtc gaacagcaca agcactacct ggacgaaatc atcgaacaga tcagcgaatt | 3900 |
| cagcaagaga gtcatcctgg cagacgcaaa cctggacaag gtcctgagcg catacaacaa | 3960 |
| gcacagagac aagccgatca gagaacaggc agaaaacatc atccacctgt tcacactgac | 4020 |
| aaacctggga gcaccggcag cattcaagta cttcgacaca caatcgaca gaaagagata | 4080 |
| cacaagcaca aaggaagtcc tggacgcaac actgatccac cagagcatca caggactgta | 4140 |
| cgaaacaaga atcgacctga ccagctggg aggagacgga ggaggaagcc cgaagaagaa | 4200 |
| gagaaaggtc tagctagcca tcacatttaa aagcatctca gcctaccatg agaataagag | 4260 |
| aaagaaaatg aagatcaata gcttattcat ctctttttct ttttcgttgg tgtaaagcca | 4320 |
| acaccctgtc taaaaaacat aaatttcttt aatcattttg cctcttttct ctgtgcttca | 4380 |
| attaataaaa aatggaaaga accaaaaaaa aaaaaaaaa aaaaaaaaaa aaaaaaaaa | 4440 |
| aaaaaaaaaa aaaaaaaaa aaaaaaaaa aaaaaaaaa aaaaaaaaa aaaaaaaaa | 4500 |

<210> SEQ ID NO 31
<211> LENGTH: 4500
<212> TYPE: DNA
<213> ORGANISM: Artificial Sequence
<220> FEATURE:
<223> OTHER INFORMATION: Synthetic: Cas9 mRNA with a poly-A tail
    comprising SEQ ID NO: 2

<400> SEQUENCE: 31

| | |
|---|---|
| tcccgcagtc ggcgtccagc ggctctgctt gttcgtgtgt gtgtcgttgc aggccttatt | 60 |
| cggatccgcc accatggaca agaagtacag catcggactg gacatcggaa caaacagcgt | 120 |
| cggatgggca gtcatcacag acgaatacaa ggtcccgagc aagaagttca aggtcctggg | 180 |
| aaacacagac agacacagca tcaagaagaa cctgatcgga gcactgctgt tcgacagcgg | 240 |
| agaaacagca gaagcaacaa gactgaagag aacagcaaga gaagatacaa caagaagaaa | 300 |
| gaacagaatc tgctacctgc aggaaatctt cagcaacgaa atggcaaagg tcgacgacag | 360 |
| cttcttccac agactggaag aaagcttcct ggtcgaagaa gacaagaagc acgaaagaca | 420 |
| cccgatcttc ggaaacatcg tcgacgaagt cgcataccac gaaaagtacc cgacaatcta | 480 |

```
ccacctgaga aagaagctgg tcgacagcac agacaaggca gacctgagac tgatctacct    540
ggcactggca cacatgatca agttcagagg acacttcctg atcgaaggag acctgaaccc    600
ggacaacagc gacgtcgaca agctgttcat ccagctggtc cagacataca accagctgtt    660
cgaagaaaac ccgatcaacg caagcggagt cgacgcaaag gcaatcctga gcgcaagact    720
gagcaagagc agaagactgg aaaacctgat cgcacagctg ccgggagaaa agaagaacgg    780
actgttcgga aacctgatcg cactgagcct gggactgaca ccgaacttca gagcaacttc    840
cgacctggca gaagacgcaa agctgcagct gagcaaggac acatacgacg acgacctgga    900
caacctgctg gcacagatcg agaccagta cgcagacctg ttcctggcag caaagaacct    960
gagcgacgca atcctgctga gcgacatcct gagagtcaac acagaaatca caaaggcacc   1020
gctgagcgca agcatgatca agagatacga cgaacaccac caggacctga cactgctgaa   1080
ggcactggtc agacagcagc tgccggaaaa gtacaaggaa atcttcttcg accagagcaa   1140
gaacggatac gcaggataca tcgacggagg agcaagccag gaagaattct acaagttcat   1200
caagccgatc ctggaaaaga tggacggaac agaagaactg ctggtcaagc tgaacagaga   1260
agacctgctg agaaagcaga gaacattcga caacggaagc atcccgcacc agatccacct   1320
gggagaactg cacgcaatcc tgagaagaca ggaagacttc tacccgttcc tgaaggacaa   1380
cagagaaaag atcgaaagat cctgacatt cagaatcccg tactacgtcg accgctggc    1440
aagaggaaac agcagattcg catggatgac aagaaagagc gaagaaacaa tcacaccgtg   1500
gaacttcgaa gaagtcgtcg acaagggagc aagcgcacag agcttcatcg aaagaatgac   1560
aaacttcgac aagaacctgc cgaacgaaaa ggtcctgccg aagcacagcc tgctgtacga   1620
atacttcaca gtctacaacg aactgacaaa ggtcaagtac gtcacagaag aatgagaaa    1680
gccggcattc ctgagcggag aacagaagaa ggcaatcgtc gacctgctgt tcaagacaaa   1740
cagaaaggtc acagtcaagc agctgaagga agactacttc aagaagatcg aatgcttcga   1800
cagcgtcgaa atcagcggag tcgaagacag attcaacgca agcctgggaa cataccacga   1860
cctgctgaag atcatcaagg acaaggactt cctggacaac gaagaaaacg aagacatcct   1920
ggaagacatc gtcctgacac tgacactgtt cgaagacaga gaaatgatcg aagaaagact   1980
gaagacatac gcacacctgt cgacgacaa ggtcatgaag cagctgaaga aagaagata    2040
cacaggatgg ggaagactga gcagaaagct gatcaacgga atcagagaca agcagagcgg   2100
aaagacaatc ctggacttcc tgaagagcga cggattcgca aacagaaact tcatgcagct   2160
gatccacgac gacagcctga cattcaagga agacatccag aaggcacagg tcagcggaca   2220
gggagacagc ctgcacgaac acatcgcaaa cctggcagga agcccggcaa tcaagaaggg   2280
aatcctgcag acagtcaagg tcgtcgacga actggtcaag gtcatgggaa gacacaagcc   2340
ggaaaacatc gtcatcgaaa tggcaagaga aaaccagaca acacagaagg gacagaagaa   2400
cagcagagaa agaatgaaga gaatcgaaga aggaatcaag gaactgggaa gccagatcct   2460
gaaggaacac ccggtcgaaa acacacagct gcagaacgaa aagctgtacc tgtactacct   2520
gcagaacgga agagacatgt acgtcgacca ggaactggac atcaacagac tgagcgacta   2580
cgacgtcgac cacatcgtcc cgcagagctt cctgaaggac gacagcatcg acaacaaggt   2640
cctgacaaga agcgacaaga acagaggaaa gagcgacaac gtcccgagcg aagaagtcgt   2700
caagaagatg aagaactact ggagacagct gctgaacgca agctgatca cacagagaaa   2760
gttcgacaac ctgacaaagg cagagagagg aggactgagc gaactggaca aggcaggatt   2820
catcaagaga cagctggtcg aaacaagaca gatcacaaag cacgtcgcac agatcctgga   2880
```

```
cagcagaatg aacacaaagt acgacgaaaa cgacaagctg atcagagaag tcaaggtcat    2940
cacactgaag agcaagctgg tcagcgactt cagaaaggac ttccagttct acaaggtcag    3000
agaaatcaac aactaccacc acgcacacga cgcatacctg aacgcagtcg tcggaacagc    3060
actgatcaag aagtacccga agctggaaag cgaattcgtc tacggagact acaaggtcta    3120
cgacgtcaga aagatgatcg caaagagcga acaggaaatc ggaaaggcaa cagcaaagta    3180
cttcttctac agcaacatca tgaacttctt caagacagaa atcacactgg caaacggaga    3240
aatcagaaag agaccgctga tcgaaacaaa cggagaaaca ggagaaatcg tctgggacaa    3300
gggaagagac ttcgcaacag tcagaaaggt cctgagcatg ccgcaggtca acatcgtcaa    3360
gaagacagaa gtccagacag gaggattcag caaggaaagc atcctgccga agagaaacag    3420
cgacaagctg atcgcaagaa agaaggactg ggacccgaag aagtacggag gattcgacag    3480
cccgacagtc gcatacagcg tcctggtcgt cgcaaaggtc gaaaagggaa agagcaagaa    3540
gctgaagagc gtcaaggaac tgctgggaat cacaatcatg gaaagaagca gcttcgaaaa    3600
gaacccgatc gacttcctgg aagcaaaggg atacaaggaa gtcaagaagg acctgatcat    3660
caagctgccg aagtacagcc tgttcgaact ggaaaacgga agaaagagaa tgctggcaag    3720
cgcaggagaa ctgcagaagg gaaacgaact ggcactgccg agcaagtacg tcaacttcct    3780
gtacctggca agccactacg aaaagctgaa gggaagcccg gaagcaacg aacagaagca     3840 gctgttcgtc gaacagcaca agcactacct ggacgaaatc atcgaacaga tcagcgaatt    3900
cagcaagaga gtcatcctgg cagacgcaaa cctggacaag gtcctgagcg catacaacaa    3960
gcacagagac aagccgatca gagaacaggc agaaaacatc atccacctgt tcacactgac    4020
aaacctggga gcaccggcag cattcaagta cttcgacaca acaatcgaca gaaagagata    4080
cacaagcaca aaggaagtcc tggacgcaac actgatccac cagagcatca caggactgta    4140
cgaaacaaga atcgacctga gccagctggg aggagacgga ggaggaagcc cgaagaagaa    4200
gagaaaggtc tagctagcca tcacatttaa aagcatctca gcctaccatg agaataagag    4260
aaagaaaatg aagatcaata gcttattcat ctctttttct ttttcgttgg tgtaaagcca    4320
acaccctgtc taaaaaacat aaatttcttt aatcattttg cctctttct ctgtgcttca     4380 attaataaaa aatggaaaga accaaaaaaa aaaaaaaaa aaaaaaaaaa aaaaaaaaa      4440 aaaaaaaaa aaaaaaaaa aaaaaaaaa aaaaaaaaa aaaaaaaaa aaaaaaaaa         4500
```